(12) United States Patent
Li et al.

(10) Patent No.: US 11,485,783 B2
(45) Date of Patent: Nov. 1, 2022

(54) ANTI-GPRC5D MONOCLONAL ANTIBODIES AND USES THEREOF

(71) Applicant: LaNova Medicines Development Co., Ltd., Shanghai (CN)

(72) Inventors: Runsheng Li, Shanghai (CN); Wentao Huang, Shanghai (CN)

(73) Assignee: LANOVA MEDICINES DEVELOPMENT CO., LTD., Shanghai (CN)

( * ) Notice: Subject to any disclaimer, the term of this patent is extended or adjusted under 35 U.S.C. 154(b) by 0 days.

(21) Appl. No.: 17/685,029

(22) Filed: Mar. 2, 2022

(65) Prior Publication Data
US 2022/0220203 A1   Jul. 14, 2022

Related U.S. Application Data

(63) Continuation of application No. PCT/CN2022/070287, filed on Jan. 5, 2022.

(30) Foreign Application Priority Data

Jan. 5, 2021 (CN) .................. PCT/CN2021/070314

(51) Int. Cl.
 *C07K 16/28* (2006.01)
 *A61P 35/00* (2006.01)
 *A61K 39/00* (2006.01)

(52) U.S. Cl.
 CPC .......... *C07K 16/2809* (2013.01); *A61P 35/00* (2018.01); *A61K 2039/505* (2013.01); *C07K 2317/21* (2013.01); *C07K 2317/31* (2013.01); *C07K 2317/33* (2013.01); *C07K 2317/565* (2013.01); *C07K 2317/732* (2013.01); *C07K 2317/734* (2013.01); *C07K 2317/76* (2013.01); *C07K 2317/92* (2013.01); *C07K 2317/94* (2013.01)

(58) Field of Classification Search
 None
 See application file for complete search history.

(56) References Cited

U.S. PATENT DOCUMENTS

| 10,562,968 B2 | 2/2020 | Attar et al. |
| 2018/0037651 A1 | 2/2018 | Attar et al. |
| 2019/0367612 A1* | 12/2019 | Chaen .................... C12N 15/09 |

FOREIGN PATENT DOCUMENTS

| EP | 3581651 A1 | 12/2019 |
| WO | 2016090329 A2 | 6/2016 |
| WO | 2018017786 A2 | 1/2018 |
| WO | 2018147245 A1 | 8/2018 |
| WO | 2019154890 A1 | 8/2019 |
| WO | 2020092854 A2 | 5/2020 |
| WO | 2020148677 A1 | 7/2020 |

OTHER PUBLICATIONS

Kodama et al., "Anti-GPRC5D/CD3 Bispecific T Cell-redirecting Antibody for the Treatment of Multiple Myeloma", MCT-18-1216R1, Molecular Cancer Therapeutics, Published online on Jul. 3, 2019, 34 pages.
Pillarisetti et al., "A T-cell-redirecting Bispecific G-protein-coupled Receptor Class 5 Member D x CD3 Antibody to Treat Multiple Myeloma", Blood, Apr. 9, 2020, vol. 135, No. 15 pp. 1232-1243.
Smith et al., "GPRC5D is a Target for the Immunotherapy of Multiple Myeloma with Rationally Designed CAR T Cells", Sci. Transl. Med., 11, eaau7746, 14 pages, Mar. 27, 2019.
Chari et al., "A Phase 1, First-in-Human Study of Talquetamab, a G Protein-Coupled Receptor Family C Group 5 Member D (GPRC5D) x CD3 Bispecific Antibody, in Patients with Relapsed and/or Refractory Multiple Myeloma (RRMM)", Blood, 2020, 136, Supplement 1, pp. 40-41.
International Search Report and Written Opinion for PCT/CN2022/070287 dated Apr. 7, 2022, 16 pages.

* cited by examiner

*Primary Examiner* — Meera Natarajan
(74) *Attorney, Agent, or Firm* — Sheppard Mullin Richter & Hampton LLP

(57) ABSTRACT

Provided are antibodies or fragment thereof having binding specificity to the human GPRC5D protein. The antibodies or fragment thereof are capable of targeting cancer cells expressing GPRC5D, and thus can be used to treat the cancer, in particular hematological cancer.

24 Claims, 18 Drawing Sheets

Specification includes a Sequence Listing.

ANTI-GPRC5D MONOCLONAL ANTIBODIES AND USES THEREOF

CROSS REFERENCE TO RELATED APPLICATIONS

The present application is a continuation of International Application No. PCT/CN2022/070287, filed Jan. 5, 2022, which claims priority to PCT/CN2021/070314, filed Jan. 5, 2021, the contents of each of which is incorporated herein by reference in its entirety in the present disclosure.

SEQUENCE LISTING

The instant application contains a Sequence Listing which has been submitted in ASCII format via EFS-Web and is hereby incorporated by reference in its entirety. Said ASCII copy, created on Mar. 1, 2022, is named Sequences.txt and is 70,296 bytes in size.

BACKGROUND

G-protein-coupled receptor family C group 5 member D (GPRC5D) is member of the G protein-coupled receptor family. GPRC5D is a transmembrane protein. Overexpression of GPRC5D was observed in patients with multiple myeloma. In particular, its high expression had a significant correlation with poor outcome of the disease and treatment.

Given its specific high expression on malignant cells, it has been proposed that antibodies that are specific to GPRC5D can be useful for treating the malignancy, such as via a bispecific T-cell-redirecting antibody, or through antibody-dependent cellular cytotoxicity (ADCC).

SUMMARY

Anti-GPRC5D antibodies, including their humanized derivatives, are discovered herein that have high affinity to the human GPRC5D protein. The antibodies or fragment thereof are capable of targeting cancer cells expressing GPRC5D, and thus can be used to treat the cancer, in particular hematological cancer.

One embodiment of the present disclosure provides an antibody or antigen-binding fragment thereof having binding specificity to a human G-protein-coupled receptor family C group 5 member D (GPRC5D) protein, wherein the antibody or fragment thereof comprises a heavy chain variable region (VH) comprising heavy chain complementarity determining regions CDRH1, CDRH2, and CDRH3 and a light chain variable region (VL) comprising complementarity determining regions CDRL1, CDRL2, and CDRL3. In some embodiments, the CDRH1, CDRH2, CDRH3, CDRL1, CDRL2, and CDRL3, respectively, comprise: (a) the amino acid sequences of SEQ ID NO:29-34; (b) the amino acid sequences of SEQ ID NO:42-47; (c) the amino acid sequences of SEQ ID NO:54-59; or (d) the amino acid sequences of SEQ ID NO:68-73.

In some embodiments, the CDRH1, CDRH2, CDRH3, CDRL1, CDRL2, and CDRL3, respectively, comprise the amino acid sequences of SEQ ID NO:29-34. In some embodiments, the VH comprises an amino acid sequence selected from the group consisting of SEQ ID NO:7 and 35-37, and the VL comprises an amino acid sequence selected from the group consisting of SEQ ID NO:8 and 38-41. In some embodiments, the VH comprises the amino acid sequence of SEQ ID NO:35, and the VL comprises the amino acid sequence of SEQ ID NO:38.

In some embodiments, the CDRH1, CDRH2, CDRH3, CDRL1, CDRL2, and CDRL3, respectively, comprise the amino acid sequences of SEQ ID NO:42-47. In some embodiments, the VH comprises an amino acid sequence selected from the group consisting of SEQ ID NO:9 and 48-50, and the VL comprises an amino acid sequence selected from the group consisting of SEQ ID NO:10 and 51-53. In some embodiments, the VH comprises the amino acid sequence of SEQ ID NO:48, and the VL comprises the amino acid sequence of SEQ ID NO:51.

In some embodiments, the CDRH1, CDRH2, CDRH3, CDRL1, CDRL2, and CDRL3, respectively, comprise the amino acid sequences of SEQ ID NO:54-59. In some embodiments, the VH comprises an amino acid sequence selected from the group consisting of SEQ ID NO:61-64, and the VL comprises an amino acid sequence selected from the group consisting of SEQ ID NO:16 and 65-67. In some embodiments, the VH comprises the amino acid sequence of SEQ ID NO:61, and the VL comprises the amino acid sequence of SEQ ID NO:65. In some embodiments, the VH comprises the amino acid sequence of SEQ ID NO:63, and the VL comprises the amino acid sequence of SEQ ID NO:65.

In some embodiments, the CDRH1, CDRH2, CDRH3, CDRL1, CDRL2, and CDRL3, respectively, comprise the amino acid sequences of SEQ ID NO:68-73. In some embodiments, the VH comprises an amino acid sequence selected from the group consisting of SEQ ID NO:1 and 74-79, and the VL comprises an amino acid sequence selected from the group consisting of SEQ ID NO:2 and 80-86. In some embodiments, the VH comprises the amino acid sequence of SEQ ID NO:76, and the VL comprises the amino acid sequence of SEQ ID NO:82. In some embodiments, the VH comprises the amino acid sequence of SEQ ID NO:77, and the VL comprises the amino acid sequence of SEQ ID NO:82.

In some embodiments, the antibody or fragment thereof is humanized. In some embodiments, the antibody or fragment thereof is ADCC-competent.

Also provided, in some embodiments, the antibody or fragment thereof further comprises a cytotoxic drug conjugated to the antibody or fragment thereof.

Also provided is a bispecific antibody, comprising the antigen-binding fragment of the present disclosure, and a second antigen-binding fragment having specificity to a second target protein. In some embodiments, the second target protein is selected from the group consisting of CD3, CD16, CD19, CD28, CD64 and 4-1BB. In some embodiments, the second target protein is CD3. In some embodiments, the second target protein is 4-1BB.

Also provided is a method of treating cancer in a patient in need thereof, comprising administering to the patient the antibody or fragment thereof of the present disclosure. Also provided is a method of treating cancer in a patient in need thereof, comprising (a) treating a T cell, a natural killer (NK) cell, or a macrophage, in vitro, with the antibody or fragment thereof of the present disclosure, and (b) administering the treated cell to the patient.

In some embodiments, the cancer is a hematological cancer, such as a GPRC5D-expressing B cell cancer (e.g., multiple myeloma).

DETAILED DESCRIPTION

Definitions

Figure 1:
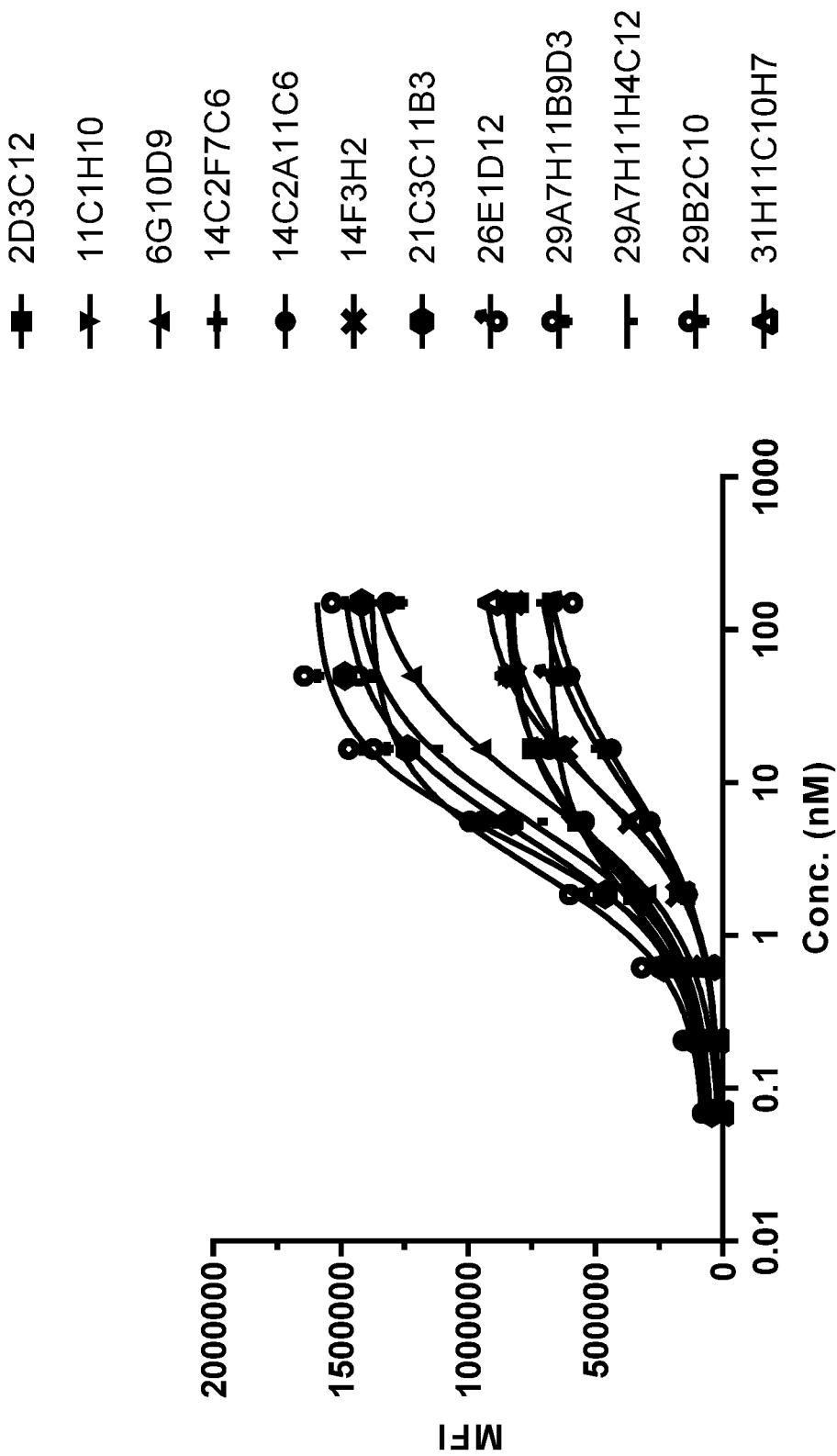
FIG. 1 shows binding of murine antibodies collected from hybridoma supernatant to GPRC5D expressed on CHO-K1 cells.
Figure 1:
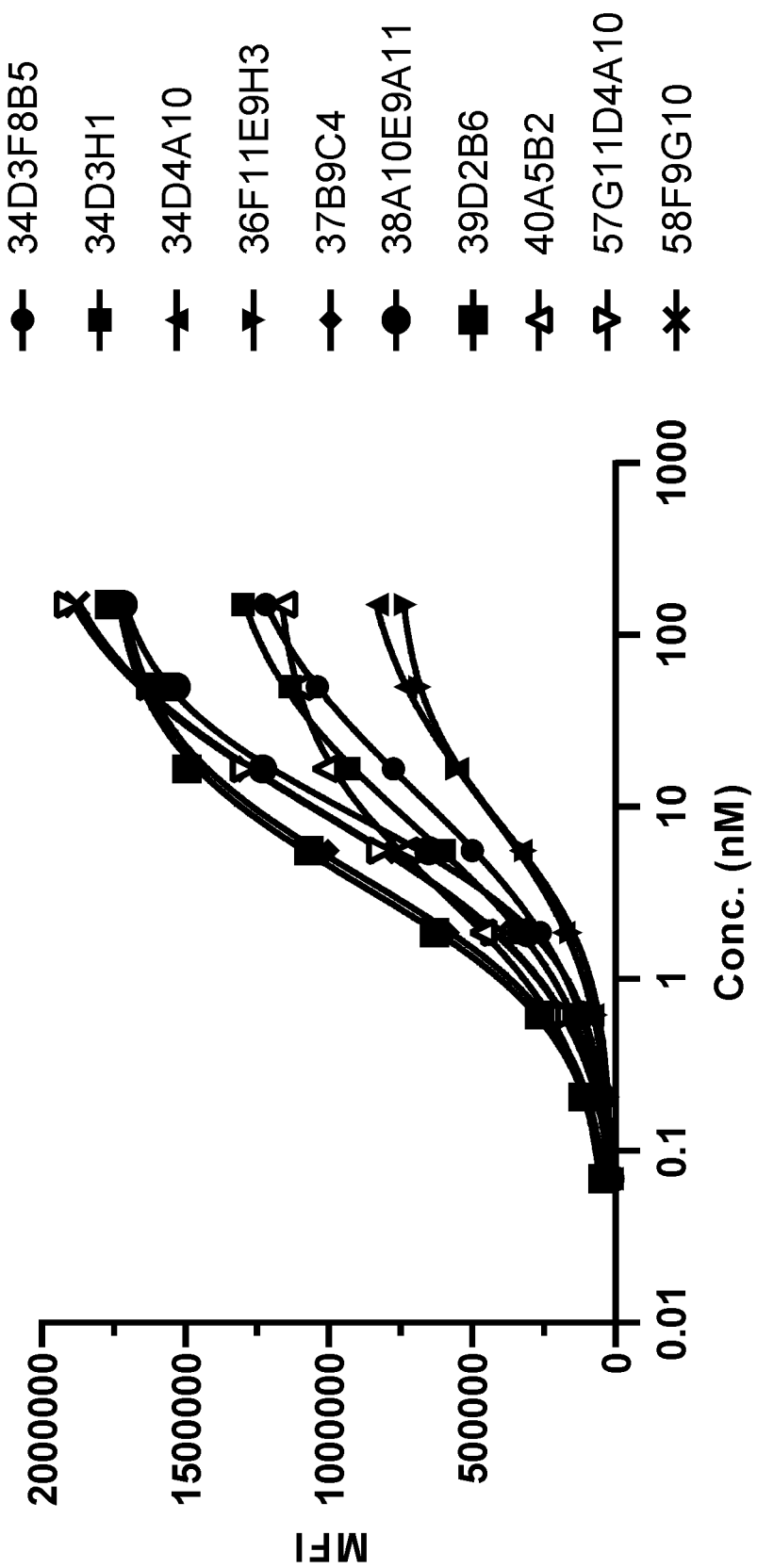

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences.

The term "an equivalent nucleic acid or polynucleotide" refers to a nucleic acid having a nucleotide sequence having a certain degree of homology, or sequence identity, with the nucleotide sequence of the nucleic acid or complement thereof. A homolog of a double stranded nucleic acid is intended to include nucleic acids having a nucleotide sequence which has a certain degree of homology with or with the complement thereof In one aspect, homologs of nucleic acids are capable of hybridizing to the nucleic acid or complement thereof. Likewise, "an equivalent polypeptide" refers to a polypeptide having a certain degree of homology, or sequence identity, with the amino acid sequence of a reference polypeptide. In some aspects, the sequence identity is at least about 70%, 75%, 80%, 85%, 90%, 95%, 98%, or 99%. In some aspects, the equivalent polypeptide or polynucleotide has one, two, three, four or five addition, deletion, substitution and their combinations thereof as compared to the reference polypeptide or polynucleotide. In some aspects, the equivalent sequence retains the activity (e.g., epitope-binding) or structure (e.g., salt-bridge) of the reference sequence.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as $F(ab')_2$, $F(ab)_2$, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

A "single-chain variable fragment" or "scFv" refers to a fusion protein of the variable regions of the heavy ($V_H$) and light chains ($V_L$) of immunoglobulins. In some aspects, the regions are connected with a short linker peptide of ten to about 25 amino acids. The linker can be rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker. ScFv molecules are known in the art and are described, e.g., in U.S. Pat. No. 5,892,019.

The term antibody encompasses various broad classes of polypeptides that can be distinguished biochemically. Those skilled in the art will appreciate that heavy chains are classified as gamma, mu, alpha, delta, or epsilon (γ, μ, α, δ, ε) with some subclasses among them (e.g., γ1- γ4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgG5, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Antibodies, antigen-binding polypeptides, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VK or VH domain, fragments produced by a Fab expression library, and anti-idiotypic (anti-Id) antibodies (including, e.g., anti-Id antibodies to LIGHT antibodies disclosed herein). Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Light chains are classified as either kappa or lambda (K, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VK) and heavy (VH) chain portions determine antigen recognition and specificity. Conversely, the constant domains of the light chain (CK) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CK domains actually comprise the carboxy-terminus of the heavy and light chain, respectively.

As indicated above, the variable region allows the antibody to selectively recognize and specifically bind epitopes on antigens. That is, the VK domain and VH domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the VH and VK chains (i.e. CDR-H1, CDR-H2, CDR-H3, CDR-L1, CDR-L2 and CDR-L3). In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., Nature 363:446-448 (1993).

In naturally occurring antibodies, the six "complementarity determining regions" or "CDRs" present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see "Sequences of Proteins of Immunological Interest," Kabat, E., et al., U.S. Department of Health and Human Services, (1983); and Chothia and Lesk, J. Mol. Biol., 196:901-917 (1987)).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., J. Mol. Biol. 196:901-917 (1987), which are incorporated herein by reference in their entireties. The CDR definitions according to Kabat and Chothia include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth in the table below as a comparison. The exact residue numbers which encompass a particular CDR will vary depending on the sequence and size of the CDR. Those skilled in the art can routinely determine which residues comprise a particular CDR given the variable region amino acid sequence of the antibody.

|  | Kabat | Chothia |
|---|---|---|
| CDR-H1 | 31-35 | 26-32 |
| CDR-H2 | 50-65 | 52-58 |
| CDR-H3 | 95-102 | 95-102 |
| CDR-L1 | 24-34 | 26-32 |
| CDR-L2 | 50-56 | 50-52 |
| CDR-L3 | 89-97 | 91-96 |

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983).

In addition to table above, the Kabat number system describes the CDR regions as follows: CDR-H1 begins at approximately amino acid 31 (i.e., approximately 9 residues after the first cysteine residue), includes approximately 5-7 amino acids, and ends at the next tryptophan residue. CDR-H2 begins at the fifteenth residue after the end of CDR-H1, includes approximately 16-19 amino acids, and ends at the next arginine or lysine residue. CDR-H3 begins at approximately the thirty third amino acid residue after the end of CDR-H2; includes 3-25 amino acids; and ends at the sequence W-G-X-G, where X is any amino acid. CDR-L1 begins at approximately residue 24 (i.e., following a cysteine residue); includes approximately 10-17 residues; and ends at the next tryptophan residue. CDR-L2 begins at approximately the sixteenth residue after the end of CDR-L1 and includes approximately 7 residues. CDR-L3 begins at approximately the thirty third residue after the end of CDR-L2 (i.e., following a cysteine residue); includes approximately 7-11 residues and ends at the sequence F or W-G-X-G, where X is any amino acid.

Antibodies disclosed herein may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, an antibody for use in the disclosure may lack at least a portion of a CH2 domain (e.g., all or part of a CH2 domain). As set forth above, it will be understood by one of ordinary skill in the art that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a CH1 domain derived from an IgG$_1$ molecule and a hinge region derived from an IgG$_3$ molecule. In another example, a heavy chain constant region can comprise a hinge region derived, in part, from an IgG$_1$ molecule and, in part, from an IgG$_3$ molecule. In another example, a heavy chain portion can comprise a chimeric hinge derived, in part, from an IgG$_1$ molecule and, in part, from an IgG$_4$ molecule.

As used herein, the term "light chain constant region" includes amino acid sequences derived from antibody light chain. Preferably, the light chain constant region comprises at least one of a constant kappa domain or constant lambda domain.

A "light chain-heavy chain pair" refers to the collection of a light chain and heavy chain that can form a dimer through a disulfide bond between the CL domain of the light chain and the CH1 domain of the heavy chain.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat et al., U.S. Dept. of Health and Human Services, "Sequences of Proteins of Immunological Interest" (1983). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al., J. Immunol 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CK regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant disclosure) is obtained from a second species. In certain embodiments the target binding region or site will be from a non-human source (e.g. mouse or primate) and the constant region is human.

As used herein, "percent humanization" is calculated by determining the number of framework amino acid differences (i.e., non-CDR difference) between the humanized domain and the germline domain, subtracting that number from the total number of amino acids, and then dividing that by the total number of amino acids and multiplying by 100.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

Anti-GPRC5D Antibodies

Using the hybridoma technology, the accompanying experimental examples showed that a number of murine antibodies were obtained. Fourteen of the murine antibodies were sequenced, and humanized antibodies were made. These humanized antibodies exhibited potent GPRC5D-binding activities, and were able to induce receptor-mediated endocytosis. In vivo testing showed that these antibodies were active in inducing ADCC and inhibiting tumor development.

Four of the murine antibodies, 34D3H1, 37B9C4, 58F9G10 and 6G10D9, went through the humanization process. Some of the humanized antibodies, including 6-H3L3, 6-H4L3 (both derived from 6G10D9), 58-H1L1, 58-H3L1 (both derived from 58F9G10), 34-H1L1 (derived from 34D3H1) and 37-H1L1 (derived from 37B9C4) further showed promise to continued clinical development.

In accordance with one embodiment of the present disclosure, therefore, provided is an antibody or antigen-binding fragment thereof having binding specificity to a human G-protein-coupled receptor family C group 5 member D (GPRC5D) protein. The antibody or fragment thereof includes a heavy chain variable region (VH) comprising heavy chain complementarity determining regions CDRH1, CDRH2, and CDRH3 and a light chain variable region (VL) comprising complementarity determining regions CDRL1, CDRL2, and CDRL3.

In some embodiments, the CDRH1, CDRH2, CDRH3, CDRL1, CDRL2, and CDRL3, respectively, include (a) the amino acid sequences of SEQ ID NO: 29-34; (b) the amino acid sequences of SEQ ID NO: 42-47; (c) the amino acid sequences of SEQ ID NO:54-59, or SEQ ID NO:54, 60, and 56-59; or (d) the amino acid sequences of SEQ ID NO:68-73.

In one embodiment, the CDRH1, CDRH2, CDRH3, CDRL1, CDRL2, and CDRL3, respectively, include the amino acid sequences of SEQ ID NO:29-34. Example sequences for the VH include SEQ ID NO:7 and 35-37 or a sequence having at least 85%, 90%, or 95% sequence identity to any of SEQ ID NO:7 and 35-37. Example sequences for the VL include SEQ ID NO:8 and 38-41 or a sequence having at least 85%, 90%, or 95% sequence identity to any of SEQ ID NO:8 and 38-41.

In one embodiment, the VH includes the amino acid sequence of SEQ ID NO:35 or a sequence having at least 85%, 90%, or 95% sequence identity to SEQ ID NO:35. In one embodiment, the VL includes the amino acid sequence of SEQ ID NO:38 or a sequence having at least 85%, 90%, or 95% sequence identity to SEQ ID NO:38.

Also provided, in some embodiments, are antibodies and antigen-binding fragments thereof that bind to the same epitope on FAPa as any one of these antibodies. Also provided, in some embodiments, are antibodies and antigen-binding fragments thereof that compete with any one of these antibodies in binding to FAPa, such as one that has a VH that includes the amino acid sequence of SEQ ID NO:35 and a VL that includes the amino acid sequence of SEQ ID NO:38.

In one embodiment, the CDRH1, CDRH2, CDRH3, CDRL1, CDRL2, and CDRL3, respectively, include the amino acid sequences of SEQ ID NO:42-47. Example sequences for the VH include SEQ ID NO: 9 and 48-50 or a sequence having at least 85%, 90%, or 95% sequence identity to any of SEQ ID NO: 9 and 48-50. Example sequences for the VL include SEQ ID NO:10 and 51-53 or a sequence having at least 85%, 90%, or 95% sequence identity to any of SEQ ID NO:10 and 51-53.

In one embodiment, the VH includes the amino acid sequence of SEQ ID NO:48 or a sequence having at least 85%, 90%, or 95% sequence identity to SEQ ID NO:48. In one embodiment, the VL includes the amino acid sequence of SEQ ID NO:51 or a sequence having at least 85%, 90%, or 95% sequence identity to SEQ ID NO:51.

Also provided, in some embodiments, are antibodies and antigen-binding fragments thereof that bind to the same epitope on FAPa as any one of these antibodies. Also provided, in some embodiments, are antibodies and antigen-binding fragments thereof that compete with any one of these antibodies in binding to FAPa, such as one that has a VH that includes the amino acid sequence of SEQ ID NO:48 and a VL that includes the amino acid sequence of SEQ ID NO:51.

In one embodiment, the CDRH1, CDRH2, CDRH3, CDRL1, CDRL2, and CDRL3, respectively, include the amino acid sequences of SEQ ID NO:54-59. Example sequences for the VH include SEQ ID NO: 61-64 or a sequence having at least 85%, 90%, or 95% sequence identity to any of SEQ ID NO: 61-64. Example sequences for the VL include SEQ ID NO: 16 and 65-67 or a sequence having at least 85%, 90%, or 95% sequence identity to any of SEQ ID NO: 16 and 65-67.

In one embodiment, the VH includes the amino acid sequence of SEQ ID NO:61 or a sequence having at least 85%, 90%, or 95% sequence identity to SEQ ID NO:61. In one embodiment, the VL includes the amino acid sequence of SEQ ID NO:65 or a sequence having at least 85%, 90%, or 95% sequence identity to SEQ ID NO:65.

Also provided, in some embodiments, are antibodies and antigen-binding fragments thereof that bind to the same epitope on FAPa as any one of these antibodies. Also provided, in some embodiments, are antibodies and antigen-binding fragments thereof that compete with any one of these antibodies in binding to FAPa, such as one that has a VH that includes the amino acid sequence of SEQ ID NO:61 and a VL that includes the amino acid sequence of SEQ ID NO:65.

In one embodiment, the VH includes the amino acid sequence of SEQ ID NO:63 or a sequence having at least 85%, 90%, or 95% sequence identity to SEQ ID NO:63. In one embodiment, the VL includes the amino acid sequence of SEQ ID NO:65 or a sequence having at least 85%, 90%, or 95% sequence identity to SEQ ID NO:65.

Also provided, in some embodiments, are antibodies and antigen-binding fragments thereof that bind to the same epitope on FAPa as any one of these antibodies. Also provided, in some embodiments, are antibodies and antigen-binding fragments thereof that compete with any one of these antibodies in binding to FAPa, such as one that has a VH that includes the amino acid sequence of SEQ ID NO:63 and a VL that includes the amino acid sequence of SEQ ID NO:65.

In one embodiment, the CDRH1, CDRH2, CDRH3, CDRL1, CDRL2, and CDRL3, respectively, include the amino acid sequences of SEQ ID NO:54, 60, and 56-59. Example sequences for the VH include SEQ ID NO:15 or a sequence having at least 85%, 90%, or 95% sequence identity to any of SEQ ID NO:15. Example sequences for the VL include SEQ ID NO: 16 and 65-67 or a sequence having at least 85%, 90%, or 95% sequence identity to any of SEQ ID NO: 16 and 65-67.

In one embodiment, the CDRH1, CDRH2, CDRH3, CDRL1, CDRL2, and CDRL3, respectively, include the amino acid sequences of SEQ ID NO: 68-73. Example sequences for the VH include SEQ ID NO: 1 and 74-79 or a sequence having at least 85%, 90%, or 95% sequence identity to any of SEQ ID NO: 1 and 74-79. Example sequences for the VL include SEQ ID NO: 2 and 80-86 or a sequence having at least 85%, 90%, or 95% sequence identity to any of SEQ ID NO: 2 and 80-86.

In one embodiment, the VH includes the amino acid sequence of SEQ ID NO:76 or a sequence having at least 85%, 90%, or 95% sequence identity to SEQ ID NO:76. In one embodiment, the VL includes the amino acid sequence of SEQ ID NO:82 or a sequence having at least 85%, 90%, or 95% sequence identity to SEQ ID NO:82.

Also provided, in some embodiments, are antibodies and antigen-binding fragments thereof that bind to the same epitope on FAPa as any one of these antibodies. Also provided, in some embodiments, are antibodies and antigen-binding fragments thereof that compete with any one of these antibodies in binding to FAPa, such as one that has a VH that includes the amino acid sequence of SEQ ID NO:76 and a VL that includes the amino acid sequence of SEQ ID NO:82.

In one embodiment, the VH includes the amino acid sequence of SEQ ID NO:77 or a sequence having at least 85%, 90%, or 95% sequence identity to SEQ ID NO:77. In one embodiment, the VL includes the amino acid sequence of SEQ ID NO:82 or a sequence having at least 85%, 90%, or 95% sequence identity to SEQ ID NO:82.

Also provided, in some embodiments, are antibodies and antigen-binding fragments thereof that bind to the same epitope on FAPa as any one of these antibodies. Also provided, in some embodiments, are antibodies and antigen-binding fragments thereof that compete with any one of these antibodies in binding to FAPa, such as one that has a VH that includes the amino acid sequence of SEQ ID NO:77 and a VL that includes the amino acid sequence of SEQ ID NO:82.

In some embodiments, the antibody or fragment thereof is ADCC-competent. Methods and materials suitable for making an antibody ADCC-competent are known in the art, such as by using the appropriate Fc fragments or decreasing/removing fucosylation.

In some embodiments, the CDRH1, CDRH2, CDRH3, CDRL1, CDRL2, and CDRL3, respectively, include (a) the amino acid sequences of SEQ ID NO:29-34; (b) the amino acid sequences of SEQ ID NO:42-47; (c) the amino acid sequences of SEQ ID NO:54-59, or SEQ ID NO:54, 60, and 56-59; or (d) the amino acid sequences of SEQ ID NO:68-73, wherein each of the recited CDR sequence includes one, two or three conservative amino acid substitution.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Non-limiting examples of conservative amino acid substitutions are provided in the table below, where a similarity score of 0 or higher indicates conservative substitution between the two amino acids.

TABLE A

Amino Acid Similarity Matrix

| | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | -8 | -7 | -6 | -2 | -6 | -5 | -7 | -7 | -4 | -5 | -3 | -3 | 2 | -6 | -4 | -5 | -2 | 0 | 0 | 17 |
| Y | 0 | -5 | -5 | -3 | -3 | -3 | -4 | -4 | -2 | -4 | 0 | -4 | -5 | -2 | -2 | -1 | -1 | 7 | 10 | |
| F | -4 | -5 | -5 | -3 | -4 | -3 | -6 | -5 | -4 | -5 | -2 | -5 | -4 | -1 | 0 | 1 | 2 | 9 | | |
| L | -6 | -4 | -3 | -3 | -2 | -2 | -4 | -3 | -3 | -2 | -3 | -3 | 2 | 4 | 2 | 6 | | | | |
| I | -2 | -3 | -2 | -1 | -1 | 0 | -2 | -2 | -2 | -2 | -2 | -2 | -2 | 4 | 2 | 5 | | | | |
| M | -5 | -3 | -2 | -2 | -1 | -1 | -3 | -2 | 0 | -1 | -2 | 0 | 0 | 2 | 6 | | | | | |
| V | -2 | -1 | -1 | -1 | 0 | 0 | -2 | -2 | -2 | -2 | -2 | -2 | -2 | 4 | | | | | | |
| R | -4 | -3 | 0 | 0 | -2 | -1 | -1 | -1 | 0 | 1 | 2 | 3 | 6 | | | | | | | |
| K | -5 | -2 | -1 | 0 | -1 | 0 | 0 | 0 | 1 | 1 | 0 | 5 | | | | | | | | |
| H | -3 | -2 | 0 | -1 | -1 | -1 | 1 | 1 | 2 | 3 | 6 | | | | | | | | | |
| Q | -5 | -1 | 0 | -1 | 0 | -1 | 2 | 2 | 1 | 4 | | | | | | | | | | |
| N | -4 | 0 | -1 | 1 | 0 | 0 | 2 | 1 | 2 | | | | | | | | | | | |
| E | -5 | 0 | -1 | 0 | 0 | 0 | 3 | 4 | | | | | | | | | | | | |
| D | -5 | 1 | -1 | 0 | 0 | 0 | 4 | | | | | | | | | | | | | |
| T | -2 | 0 | 0 | 1 | 1 | 3 | | | | | | | | | | | | | | |
| A | -2 | 1 | 1 | 1 | 2 | | | | | | | | | | | | | | | |
| S | 0 | 1 | 1 | 1 | | | | | | | | | | | | | | | | |
| P | -3 | -1 | 6 | | | | | | | | | | | | | | | | | |
| G | -3 | 5 | | | | | | | | | | | | | | | | | | |
| C | 12 | | | | | | | | | | | | | | | | | | | |

TABLE B

Conservative Amino Acid Substitutions

| For Amino Acid | Substitution With |
|---|---|
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

It will also be understood by one of ordinary skill in the art that antibodies as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 0%, 85%, 90%, 95%, 8%, or 99% identical to the starting sequence.

In some embodiments, the anti-CCR8 antibodies are modified mAbs comprising a modified heavy chain constant region, such as an afucosylated heavy chain, that binds with higher affinity to activating Fcγ receptor that mediated enhanced ADCC compared to an unmodified mAb. In some embodiments, the anti-CCR8 antibodies comprises a heavy chain which is of a human IgG1 variant that include the single or combination of L234Y, L235Q, G236W, S239D/M, F243L, H268D, D270E, R292P, S298A, Y300L, V305I, K326D, A330L/M, I332E, K334A/E, P396L that enhance ADCC function (all EU numbering).

In certain embodiments, the antibody comprises an amino acid sequence or one or more moieties not normally associated with an antibody. Exemplary modifications are described in more detail below. For example, an antibody of the disclosure may comprise a flexible linker sequence, or may be modified to add a functional moiety (e.g., PEG, a drug, a toxin, or a label).

Antibodies, variants, or derivatives thereof of the disclosure include derivatives that are modified, i.e., by the covalent attachment of any type of molecule to the antibody such that covalent attachment does not prevent the antibody from binding to the epitope. For example, but not by way of limitation, the antibodies can be modified, e.g., by glycosylation, acetylation, pegylation, phosphorylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the antibodies may contain one or more non-classical amino acids.

Antibody-Drug Conjugates

GPRC5D is overexpressed on certain malignant hematological cells, such as multiple myeloma cells. The antibodies and fragments of the instant disclosure, therefore, can be used to target those malignant cells for inhibition, inactivation of destruction. In one example, the antibody or fragment is conjugated to an agent that helps to inhibit, inactive or destruct the malignant cell. It is shown herein that the antibodies are able to induce GPRC5D-mediated endocytosis.

In some embodiments, the antibodies or fragments may be conjugated to therapeutic agents, prodrugs, peptides, proteins, enzymes, viruses, lipids, biological response modifiers, pharmaceutical agents, or PEG. In some embodiments, the conjugated agent may be short interfering RNA (siRNA) or an innate modulator, such as a STimulator of Interferon Genes (STING) agonist, or a TLR7/8 agonist.

In one embodiment, the antibodies or fragments of the disclosure are covalently attached to a drug moiety. The drug moiety may be, or may be modified to include, a group reactive with a conjugation point on the antibody. For example, a drug moiety can be attached by alkylation (e.g., at the epsilon-amino group lysines or the N-terminus of antibodies), reductive amination of oxidized carbohydrate, transesterification between hydroxyl and carboxyl groups, amidation at amino groups or carboxyl groups, and conjugation to thiols.

In some embodiments, the number of drug moieties, p, conjugated per antibody molecule ranges from an average of 1 to 8; 1 to 7, 1 to 6, 1 to 5, 1 to 4, 1 to 3, or 1 to 2. In some embodiments, p ranges from an average of 2 to 8, 2 to 7, 2 to 6, 2 to 5, 2 to 4 or 2 to 3. In other embodiments, p is an average of 1, 2, 3, 4, 5, 6, 7 or 8. In some embodiments, p ranges from an average of about 1 to about 20, about 1 to about 10, about 2 to about 10, about 2 to about 9, about 1 to about 8, about 1 to about 7, about 1 to about 6, about 1 to about 5, about 1 to about 4, about 1 to about 3, or about 1 to about 2. In some embodiments, p ranges from about 2 to about 8, about 2 to about 7, about 2 to about 6, about 2 to about 5, about 2 to about 4 or about 2 to about 3.

For example, when chemical activation of the protein results in formation of free thiol groups, the protein may be conjugated with a sulfhydryl reactive agent. In one aspect, the agent is one which is substantially specific for free thiol groups. Such agents include, for example, malemide, haloacetamides (e.g., iodo, bromo or chloro), haloesters (e.g., iodo, bromo or chloro), halomethyl ketones (e.g., iodo, bromo or chloro), benzylic halides (e.g., iodide, bromide or chloride), vinyl sulfone and pyridylthio.

The drug can be linked to the antibody or fragment by a linker. Suitable linkers include, for example, cleavable and non-cleavable linkers. A cleavable linker is typically susceptible to cleavage under intracellular conditions. Suitable cleavable linkers include, for example, a peptide linker cleavable by an intracellular protease, such as lysosomal protease or an endosomal protease. In exemplary embodiments, the linker can be a dipeptide linker, such as a valine-citrulline (val-cit), a phenylalanine-lysine (phe-lys) linker, or maleimidocapronic-valine-citruline-p-aminobenzyloxycarbonyl (mc-Val-Cit-PABA) linker. Another linker is Sulfosuccinimidyl-4-[N-maleimidomethyl]cyclohexane-1-carboxylate (smcc). Sulfo-smcc conjugation occurs via a maleimide group which reacts with sulfhydryls (thiols,—SH), while its Sulfo-NHS ester is reactive toward primary amines (as found in Lysine and the protein or peptide N-terminus). Yet another linker is maleimidocaproyl (mc). Other suitable linkers include linkers hydrolyzable at a specific pH or a pH range, such as a hydrazone linker. Additional suitable cleavable linkers include disulfide linkers. The linker may be covalently bound to the antibody to such an extent that the antibody must be degraded intracellularly in order for the drug to be released e.g. the mc linker and the like.

A linker can include a group for linkage to the antibody. For example, linker can include an amino, hydroxyl, carboxyl or sulfhydryl reactive groups (e.g., malemide, haloacetamides (e.g., iodo, bromo or chloro), haloesters (e.g., iodo, bromo or chloro), halomethyl ketones (e.g., iodo, bromo or chloro), benzylic halides (e.g., iodide, bromide or chloride), vinyl sulfone and pyridylthio).

In some embodiments, the drug moiety is a cytotoxic or cytostatic agent, an immunosuppressive agent, a radioisotope, a toxin, or the like. The conjugate can be used for inhibiting the multiplication of a tumor cell or cancer cell, causing apoptosis in a tumor or cancer cell, or for treating cancer in a patient. The conjugate can be used accordingly in a variety of settings for the treatment of animal cancers. The conjugate can be used to deliver a drug to a tumor cell or cancer cell. Without being bound by theory, in some embodiments, the conjugate binds to or associates with a cancer cell expressing GPRC5D, and the conjugate and/or drug can be taken up inside a tumor cell or cancer cell through receptor-mediated endocytosis.

Once inside the cell, one or more specific peptide sequences within the conjugate (e.g., in a linker) are hydrolytically cleaved by one or more tumor-cell or cancer-cell-associated proteases, resulting in release of the drug. The released drug is then free to migrate within the cell and induce cytotoxic or cytostatic or other activities. In some embodiments, the drug is cleaved from the antibody outside the tumor cell or cancer cell, and the drug subsequently penetrates the cell, or acts at the cell surface.

Examples of drug moieties or payloads are selected from the group consisting of DM1 (maytansine, N2'-deacetyl-N2'-(3-mercapto-1-oxopropyl)- or N2'-deacetyl-N2'-(3-mercapto-1-oxopropyl)-maytansine), mc-MMAD (6-maleimidocaproyl-monomethylauristatin-D or N-methyl-L-valyl-N-[(1S,2R)-2-methoxy-4-[(2S)-2-[(1R,2R)-1-methoxy-2-methyl-3-oxo-3-[[(1S)-2-phenyl-1-(2-thiazolyl)ethyl] amino]propyl]-1-pyr rolidinyl]-1-[(1S)-1-methylpropyl]-4-oxobutyl]-N-methyl-(9Cl)-L-valinamide), mc-MMAF (maleimidocaproyl-monomethylauristatin F or N-[6-(2,5-dihydro-2,5-dioxo-1H-pyrrol-1-yl)-1-oxohexyl]-N-methyl-L-valyl-L-valyl-(3R,4S,5S)-3-methoxy-5-methyl-4-(methylamino) heptanoyl-(αR, βR,2S)-β-methoxy-α-methyl-2-pyrrolidinepropanoyl-L-phenylalanine) and mc-Val-Cit-PABA-MMAE (6-maleimidocaproyl-ValcCit-(p-aminobenzyloxycarbonyl)-monomethylauristatin E or N-[[[4-[[N-[6-(2,5-dihydro-2,5-dioxo-1H-pyrrol-1-yl)-1-oxohexyl]-L-valyl-N5-(aminocarbonyl)-L-ornithyl]amino] phenyl]methoxy]carbonyl]-N-meth yl-L-valyl-N-[(1S,2R)-4-[(2S)-2-[(1R,2R)-3-[[(1R,2S)-2-hydroxy-1-methyl-2-phenylethyl]amino]-1-methoxy-2-methyl-3-oxopropyl]-1-pyrrolidinyl]-2-methoxy-1-[(1S)-1-methylpropyl]-4-oxobutyl]-N-methyl-L-valinamide). DM1 is a derivative of the tubulin inhibitor maytansine while MMAD, MMAE, and MMAF are auristatin derivatives. In some embodiments, the drug moiety is selected from the group consisting of mc-MMAF and mc-Val-Cit-PABA-MMAE. In some embodiments, the drug moiety is a maytansinoid or an auristatin.

The antibodies or fragments may be conjugated or fused to a therapeutic agent, which may include detectable labels such as radioactive labels, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art.

The antibodies can be detectably labeled by coupling it to a chemiluminescent compound. The presence of the chemiluminescent-tagged antigen-binding polypeptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

The antibodies can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA). Techniques for conjugating various moieties to an antibody are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery (2nd Ed.), Robinson et al., (eds.), Marcel Dekker, Inc., pp. 623-53 (1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), Academic Press pp. 303-16 (1985), and Thorpe et al., "The Preparation And Cytotoxic Properties Of Antibody-Toxin Conjugates", Immunol. Rev. (52:119-58 (1982)).

Bi-functional Molecules and Combination Therapies

GPRC5D is overexpressed on certain malignant hematological cells, such as multiple myeloma cells. The antibodies and fragments of the instant disclosure, therefore, can be used to target those malignant cells for inhibition, inactivation of destruction. In some embodiments, a bi-functional or bispecific molecule/antibody is provided that targets both the GPRC5D protein and an immune cell.

In some embodiments, the immune cell is selected from the group consisting of a T cell, a B cell, a monocyte, a macrophage, a neutrophil, a dendritic cell, a phagocyte, a natural killer cell, an eosinophil, a basophil, and a mast cell. Molecules on the immune cell which can be targeted include, for example, CD3, CD16, CD19, CD28, CD64 and 4-1BB (also known as CD137). Other examples include PD-1, CTLA-4, LAG-3 (also known as CD223), CD28, CD122, TIM3, OX-40 or OX40L, CD40 or CD40L, LIGHT, ICOS/ICOSL, GITR/GITRL, TIGIT, CD27, VISTA, B7H3, B7H4, HEVM or BTLA (also known as CD272), killer-cell immunoglobulin-like receptors (KIRs), and CD47. Specific examples of bispecificity include, without limitation, GPRC5D/CD3.

Different format of bispecific antibodies are also provided. In some embodiments, each of the anti-PD-L1 fragment and the second fragment each is independently selected from a Fab fragment, a single-chain variable fragment (scFv), or a single-domain antibody. In some embodiments, the bispecific antibody further includes a Fc fragment.

Polynucleotides Encoding the Antibodies and Methods of Preparing the Antibodies

The present disclosure also provides isolated polynucleotides or nucleic acid molecules encoding the antibodies, variants or derivatives thereof of the disclosure. The polynucleotides of the present disclosure may encode the entire heavy and light chain variable regions of the antigen-binding polypeptides, variants or derivatives thereof on the same polynucleotide molecule or on separate polynucleotide molecules. Additionally, the polynucleotides of the present disclosure may encode portions of the heavy and light chain variable regions of the antigen-binding polypeptides, variants or derivatives thereof on the same polynucleotide molecule or on separate polynucleotide molecules.

Methods of making antibodies are well known in the art and described herein. In certain embodiments, both the variable and constant regions of the antigen-binding polypeptides of the present disclosure are fully human. Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties.

Treatment Methods

As described herein, the antibodies, variants or derivatives of the present disclosure may be used in certain treatment and diagnostic methods.

The present disclosure is further directed to antibody-based therapies which involve administering the antibodies of the disclosure to a patient such as an animal, a mammal, and a human for treating one or more of the disorders or conditions described herein. Therapeutic compounds of the disclosure include, but are not limited to, antibodies of the disclosure (including variants and derivatives thereof as described herein) and nucleic acids or polynucleotides encoding antibodies of the disclosure (including variants and derivatives thereof as described herein).

The antibodies of the disclosure can also be used to treat or inhibit cancer. As provided above, GPRC5D can be overexpressed in cancer cells, in particular multiple myeloma. Inhibition of GPRC5D has been shown to be useful for treating the cancers.

Accordingly, in some embodiments, provided are methods for treating a cancer in a patient in need thereof. The method, in one embodiment, entails administering to the patient an effective amount of an antibody of the present disclosure. In some embodiments, at least one of the cancer cells in the patient over-express GPRC5D. In some embodiments, the antibody or fragment is ADCC-competent. In some embodiments, the antibody or fragment further comprises a cytotoxic agent. In some embodiments, the antibody is bispecific that further targets an immune cell, such as a cytotoxic T cell.

Cellular therapies, such as chimeric antigen receptor (CAR) T-cell (or NK cell, macrophage) therapies, are also provided in the present disclosure. A suitable cell can be used, that is put in contact with an anti-GPRC5D antibody of the present disclosure (or alternatively engineered to express an anti-GPRC5D antibody of the present disclosure). Upon such contact or engineering, the cell can then be introduced to a cancer patient in need of a treatment. The cancer patient may have a cancer of any of the types as disclosed herein. The cell (e.g., T cell) can be, for instance, a tumor-infiltrating T lymphocyte, a CD4+T cell, a CD8+T cell, a natural killer (NK) cell, a macrophage, or the combination thereof, without limitation.

In some embodiments, the cell was isolated from the cancer patient him- or her-self. In some embodiments, the cell was provided by a donor or from a cell bank. When the cell is isolated from the cancer patient, undesired immune reactions can be minimized.

Non-limiting examples of cancers include hematological cancers such as multiple myeloma. Other examples include leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), and lymphomas (e.g., Hodgkin's disease and non-Hodgkin's disease), and multiple myeloma.

A specific dosage and treatment regimen for any particular patient will depend upon a variety of factors, including the particular antibodies, variant or derivative thereof used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

Methods of administration of the antibodies, variants or include but are not limited to intradermal, intramuscular, intraperitoneal, intravenous, subcutaneous, intranasal, epidural, and oral routes. The antigen-binding polypeptides or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Thus, pharmaceutical compositions containing the antigen-binding polypeptides of the disclosure may be administered orally, rectally, parenterally, intracisternally, intravaginally, intraperitoneally, topically (as by powders, ointments, drops or transdermal patch), bucally, or as an oral or nasal spray.

The term "parenteral" as used herein refers to modes of administration which include intravenous, intramuscular, intraperitoneal, intrasternal, subcutaneous and intra-articular injection and infusion.

Administration can be systemic or local. In addition, it may be desirable to introduce the antibodies of the disclosure into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

It may be desirable to administer the antigen-binding polypeptides or compositions of the disclosure locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the disclosure, care must be taken to use materials to which the protein does not absorb.

The amount of the antibodies of the disclosure which will be effective in the treatment, inhibition and prevention of an inflammatory, immune or malignant disease, disorder or condition can be determined by standard clinical techniques. In addition, in vitro assays may optionally be employed to help identify optimal dosage ranges. The precise dose to be employed in the formulation will also depend on the route of administration, and the seriousness of the disease, disorder or condition, and should be decided according to the judgment of the practitioner and each patient's circumstances. Effective doses may be extrapolated from dose-response curves derived from in vitro or animal model test systems.

As a general proposition, the dosage administered to a patient of the antigen-binding polypeptides of the present disclosure is typically 0.1 mg/kg to 100 mg/kg of the patient's body weight, between 0.1 mg/kg and 20 mg/kg of the patient's body weight, or 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the disclosure may be reduced by enhancing uptake and tissue penetration (e.g., into the brain) of the antibodies by modifications such as, for example, lipidation.

In an additional embodiment, the compositions of the disclosure are administered in combination with cytokines. Cytokines that may be administered with the compositions of the disclosure include, but are not limited to, IL-2, IL-3, IL-4, IL-5, IL-6, IL-7, IL-10, IL-12, IL-13, IL-15, anti-CD40, CD40L, and TNF-α.

In additional embodiments, the compositions of the disclosure are administered in combination with other therapeutic or prophylactic regimens, such as, for example, radiation therapy.

Diagnostic Methods

Over-expression of GPRC5D is observed in certain tumor samples, and patients having GPRC5D-over-expressing cells are likely responsive to treatments with the anti-GPRC5D antibodies of the present disclosure. Accordingly, the antibodies of the present disclosure can also be used for diagnostic and prognostic purposes.

A sample that preferably includes a cell can be obtained from a patient, which can be a cancer patient or a patient desiring diagnosis. The cell be a cell of a tumor tissue or a tumor block, a blood sample, a urine sample or any sample from the patient. Upon optional pre-treatment of the sample, the sample can be incubated with an antibody of the present disclosure under conditions allowing the antibody to interact with a GPRC5D protein potentially present in the sample. Methods such as ELISA can be used, taking advantage of the anti-GPRC5D antibody, to detect the presence of the GPRC5D protein in the sample.

Presence of the GPRC5D protein in the sample (optionally with the amount or concentration) can be used for diagnosis of cancer, as an indication that the patient is suitable for a treatment with the antibody, or as an indication that the patient has (or has not) responded to a cancer treatment. For a prognostic method, the detection can be done at once, twice or more, at certain stages, upon initiation of a cancer treatment to indicate the progress of the treatment.

Compositions

The present disclosure also provides pharmaceutical compositions. Such compositions comprise an effective amount of an antibody, and an acceptable carrier. In some embodiments, the composition further includes a second anticancer agent (e.g., an immune checkpoint inhibitor).

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

EXAMPLES

Example 1: Generation of murine monoclonal antibodies against human GPRC5D

The human GPRC5D protein was used to immunize different strains of mice and hybridomas were generated accordingly. More than twenty hybridoma clones were collected for further analysis.

Antibodies harvested from the supernatants of the hybridomas were tested for their binding to the human GPRC5D protein expressed on CHO K1 cells was tested. CHO-K1 cells stably expressed human GPRC5D, were harvested from flasks. 100 µl of $1\times10^6$ cells/ml of cells were incubated with murine antibodies in 3-fold serial dilutions for 30 minutes on ice. After being washed with 200 µl of FACS buffer twice, cells were incubated with secondary antibody for 30 minutes on ice. Cells were washed with 200 µl of FACS buffer twice and transferred to BD Falcon 5 ml tube and analyzed by FACS. The results of the study showed that the murine antibodies can bind to human GPRC5D with high EC50 (FIG. 1). The results are shown in the table below. All of them exhibited good binding activity.

|  | Bottom | Top | LogEC50 | HillSlope | EC50 | Span |
| --- | --- | --- | --- | --- | --- | --- |
| 2D3C12 | 46110 | 835137 | 0.4535 | 1.132 | 2.841 | 789027 |
| 6G10D9 | 6870 | 1429638 | 0.9116 | 0.9535 | 8.159 | 1422768 |
| 11C1H10 | 40235 | 859162 | 0.5274 | 1.101 | 3.368 | 818927 |
| 14C2A11C6 | 5573 | 728662 | 0.9934 | 0.8801 | 9.849 | 723089 |
| 14C2F7C6 | 15616 | 751279 | 0.9634 | 0.9615 | 9.193 | 735663 |
| 14F3H2 | 20428 | 872785 | 0.8744 | 1.146 | 7.489 | 852357 |
| 21C3C11B3 | 57013 | 1508205 | 0.6538 | 1.1 | 4.506 | 1451192 |
| 26E1D12 | 52742 | 677713 | 0.2246 | 1.303 | 1.677 | 624970 |
| 29A7H11B9D3 | 71394 | 1385928 | 0.4219 | 1.259 | 2.642 | 1314534 |
| 29A7H11H4C12 | 43439 | 1461931 | 0.7377 | 1.109 | 5.466 | 1418492 |
| 29B2C10 | 68634 | 1607305 | 0.6201 | 1.305 | 4.17 | 1538671 |
| 31H11C10H7 | 16791 | 961550 | 0.9534 | 1.134 | 8.983 | 944759 |
| 34D3F8B5 | −16109 | 1407656 | 1.084 | 0.7475 | 12.12 | 1423765 |
| 34D3H1 | −13314 | 1412131 | 0.8843 | 0.8042 | 7.662 | 1425446 |
| 34D4A10 | 2737 | 921851 | 1.019 | 0.8496 | 10.44 | 919114 |
| 36F11E9H3 | 13852 | 766682 | 0.8732 | 1.087 | 7.468 | 752830 |
| 37B9C4 | 10880 | 1758861 | 0.5917 | 0.9933 | 3.906 | 1747981 |
| 38A10E9A11 | 24016 | 1785041 | 0.9472 | 1.099 | 8.854 | 1761025 |
| 39D2B6 | 7833 | 1774093 | 0.5469 | 0.98 | 3.523 | 1766260 |

-continued

|         | Bottom  | Top     | LogEC50 | HillSlope | EC50  | Span    |
|---------|---------|---------|---------|-----------|-------|---------|
| 40A5B2  | 25394   | 1196144 | 0.5108  | 0.9236    | 3.242 | 1170750 |
| 57G11D4A10 | −22363 | 2089505 | 0.9703  | 0.8141    | 9.34  | 2111868 |
| 58F9G10 | −14744  | 2052463 | 0.9635  | 0.8313    | 9.194 | 2067207 |

Fourteen hybridomas were subcloned and the VH/VL sequences were determined (see Table 1).

TABLE 1

VH/VL sequence of the lead murine antibodies

| Name | Sequence (CDRs are underlined) | SEQ ID NO: |
|------|-------------------------------|------------|
| 6G10D9 VH | QVQLQQSGAELARPGASVKMSCKASGYTFTTYTMHWVKQRPGQGLEWLGY INPSSGYTNYNQKFKDKATLTAGKSSSTAYMQLSSLTSEDSAVYYCASLR SRGYFDYWGQGTTLTVSS | 1 |
| 6G10D9 VL | DIVMTQSQTFMSTSVGDRVRITCKASQNVGTAVVWYQQKTGQSPRLLIYS ASNRYTGVPDRFTGSGSGTDFTLTISNMQSEDLADFFCQQYSSYPYTFGG GTKLEIK | 2 |
| 21C3C11B3 VH | QVQLQQSGAELVRPGTSVKVSCKASGYAFINYLIEWIKQRPGQGLEWIGM INPGSGGTNYNEKFKDKATLTADKSSSTAYMQLSSLTSDDSAVYFCARNW DVWGQGTTLTVSS | 3 |
| 21C3C11B3 VL | DVVMTQSPLSLPVSLGDQASVSCRSSQSLVHSTGNTYLHWYLQKPGQSPK LLIYKVSNRFSGVPDRFSGSGSGTDFTLKISRVEAEDLGVYFCSQSTHVP WTFGGGTKLEIK | 4 |
| 29B2C10 VH | EVQLQQSGPELVKPGASMKLSCKASGYSFTGYTMHWVKQSHGENLEWIGL INPYNGGTNYNQKFKGKATLTVDKSSSTAYMELLSLTSEDSAVYYCSRWG LRRAMDYWGQGTSVTVSS | 5 |
| 29B2C10 VL | DIVMTQSQKFMSTSVGDRVSVTCKASQNVGSNVAWYQQKPGQSPKALIYS ASYRYSGVPDRFTGNGSGTDFTLTISNVQSEDLAEYFCQQYYNSPWTFGG GTKLEIK | 6 |
| 34D3H1 VH | EVHLVESGGDLVKPGGSLKLSCAASGFTFSSYGMSWVRQTPDKRLEWVAT ISSGGSYTYYPDSVKGRFTISRDNAKNTLNLQMSSLKSEDTAMYYCARQG GDAMDYWGQGTSVTVSS | 7 |
| 34D3H1 VL | DIVLTQSPATLSVTPGDSVSLSCRASQSINNNLHWYQQKSHESPRLLIKY ASQSISGIPSRFSGSGSGTDFTLSINSVETEDFGMYFCQQSNSRLTFGAG TKLELK | 8 |
| 37B9C4 VH | EVNLEESGGGLVQPGGSMKLSCVASGFTFSDYWMNWVRQSPEKGLEWVAE IRLKSNNYATHYAESVKGRFTISRDDSKSSVYLQMNNLRAEDTGIYYCTR PLLWFRRYYAMDYWGQGTSVTVSS | 9 |
| 37B9C4 VL | DIQMTQTTSSLSASLGDRITISCSASQGISNYLNWYQQKPDGTVKLLIYY TSSLHSGVPSRFSGSGSGTDYSLTISNLEPADIATYYCQQYSKLPFTFGS GTKLEIK | 10 |
| 38A10E9A11 VH | QVQLQQSGAELARPGASVKMSCKASGYTFTTYTMHWVKQRPGQGLEWIGY INPSSGYTNYNQKFKDKATLTAGKSSSTAYMQLSSLTSEDSAVYYCASLR SRGYFDYWGRGTTLTVSS | 11 |
| 38A10E9A11 VL | DIVMTQSQKFLSTSVGDRVSITCKASQNVGTAVAWYQQKPGQSPKLLIYS ASNRYTGVPDRFTGSGSGTDFTLTISNMQSEDLAGYFCQQYSSYPYTFGG GTKLEIK | 12 |
| 40A5B2 VH | EVQLQQSGPELVKPGASVKMSCKASGYTFTRNIMHWVKQKPGQGLEWIGY INPYNAGSKYNEKFKGKATLTSDISSSTAYMELSSLTSEDSAVYYCAREE VYYRYGAWFAYWGHGTLVTVSA | 13 |
| 40A5B2 VL | DIVLTQSPASLAVSLGQRATISCRASQSVSTSSYSYMHWYQQKPGQPPKL LIKYASNLESGVPARFSGSGSGTDFTLNIHPVEEEDTATYYCQHSWEIPR TFGGGTKLEIK | 14 |
| 58F9G10 VH | EVQLQQSGPELVKTGASVKISCKASGYSFTGYYIHWVKQSHGKSLEWIGY ISCYNGATSFNQKFKGKATFTVDTSSSTAYMQFNSLTSEDSAVYYCARTE LRGPWFAYWGQGTLVTVSA | 15 |

TABLE 1-continued

VH/VL sequence of the lead murine antibodies

| Name | Sequence (CDRs are underlined) | SEQ ID NO: |
|---|---|---|
| 58F9G10 VL | QTVLTQSPAIMSASPGEKVTMTCSASSSVSYMNWYQQKSGTSPKRWIYDT<br>SKLASGVPARFSGSGSGTSYSLTISSMEAEDAATYYCQQWSNNPLTFGAG<br>TKLELK | 16 |
| 2D3C12 VH | QVQLQQSGAELVRPGTSVKVSCKASGYAFINYLIEWIKQRPGQGLEWIGM<br>INPGSGGTNYNEKFKDKATLTADKSSTAYMQLSSLTSDDSAVYFCARNW<br>DVWGQGTTLTVSS | 17 |
| 2D3C12 VL | DVVMTQSPLSLPVSLGDQASVSCRSSQSLVHSTGNTYLHWYLQKPGQSPK<br>LLIYKVSNRFSGVPDRFSGSGSGTDFTLKISRVEAEDLGVYFCSQSTHVP<br>WTFGGGTKLEIK | 18 |
| 14C2A1106 VH | QVHLQQSGAELARPGASVKMSCKASGYTFTTYTMHWVKQRPGQGLEWIGY<br>INPNSAYTNYNQKFKDKATLTADKSSTAYMQLSSLTSEDSAVYYCARRV<br>LLLRVLDFFDYWGQGTTLTVSS | 19 |
| 14C2A1106 VL | DVQITQSPSYLAASPGETITINCRASKSINKYLTWYQEKPGKTNKLLIYS<br>GSTLQSGIPSRFSGSGSGSDFTLTISSLEPEDFAMYYCQQHNEYPLTFGT<br>GTKLELK | 20 |
| 14F3H2 VH | EVQLQQSGPELVKPGASMKISCKASGYSFTGYTMNWVKQSHGKNLEWIGL<br>INPYNGGIRYNQKFKGKATLTVDKSSTAYMELLSLTSEDSAVYYCARWG<br>LRRAMDYWGQGTSVTVSS | 21 |
| 14F3H2 VL | DIVMTQSQKFMSTSVGDRVSVTCKASQNVGTNVAWYQQKPGQSPKALIYS<br>ASYRYSGVPDRFTGSGSGTDFTLTISNVQSEDLAEYFCQQYNSSPWTFGG<br>GTKLEIK | 22 |
| 26E1D12 VH | EVQLQQSGPELVKPGASMKISCKASGYSFTGYTMNWVKQSHGKNLEWIGL<br>INPYNGGTNYNQKFKGKATLAVDKSSTAYMDLLSLTSEDSAVYYCSRWG<br>LRRAMDYWGQGTSVTVSS | 23 |
| 26E1D12 VL | DIVMTQSQKFMSTSVGDRVSVTCKASQNVGSNVAWYQQKPGQSPKALIYS<br>ASYRYSGVPDRFTGSGSGTDFTLTISNVQSEDLAEYFCQQYNNSPWTFGG<br>GTKLEIK | 24 |
| 29A7H11H4C12 | VHEVQLQQSGPELVKPGASMKISCKASGYSFTGYTMHWVKQSHGENLEWIGL<br>INPYNGGTNYNQKFKGKATLTVDKSSTAYMELLSLTSEDSAVYYCSRWG<br>LRRAMDYWGQGTSVTVSS | 25 |
| 29A7H11H4C12 | VLDIVMTQSQKFMSTSIGDRVSVTCKASQNVGSNVAWYQQKPGQSPKALIYS<br>ASYRYSGVPDRFTGNGSGTDFTLTISNVQSEDLAEYFCQQYYNSPWTFGG<br>GTKLEIK | 26 |
| 34D4A10 VH | QVQLQQSGAELVRPGTSVKVSCKASGYAFISYLIEWIKQRPGQGLEWIGM<br>INPGSGGTNYNEKFKDKATLTADKSSTAYMQLSSLTSDDSAVYFCARNW<br>DVWGQGTTLTVSS | 27 |
| 34D4A10 VL | DVVMTQSPLSLPVSLGDQASVSCRSSQSLVHSTGNTYLHWYLQKPGQSPK<br>LLIYKVSNRFSGVPDRFSGSGSGTDFTLKISRVEAEDLGVYFCSQSTHVP<br>WTFGGGTKLEIK | 28 |

Example 2. Binding of Chimeric Antibodies to GPRC5D

The murine VH and VK genes were produced synthetically and then respectively cloned into vectors containing the human gamma 1 and human kappa constant domains. The purified chimeric antibodies were produced from transfected CHOs cells.

Figure 2:
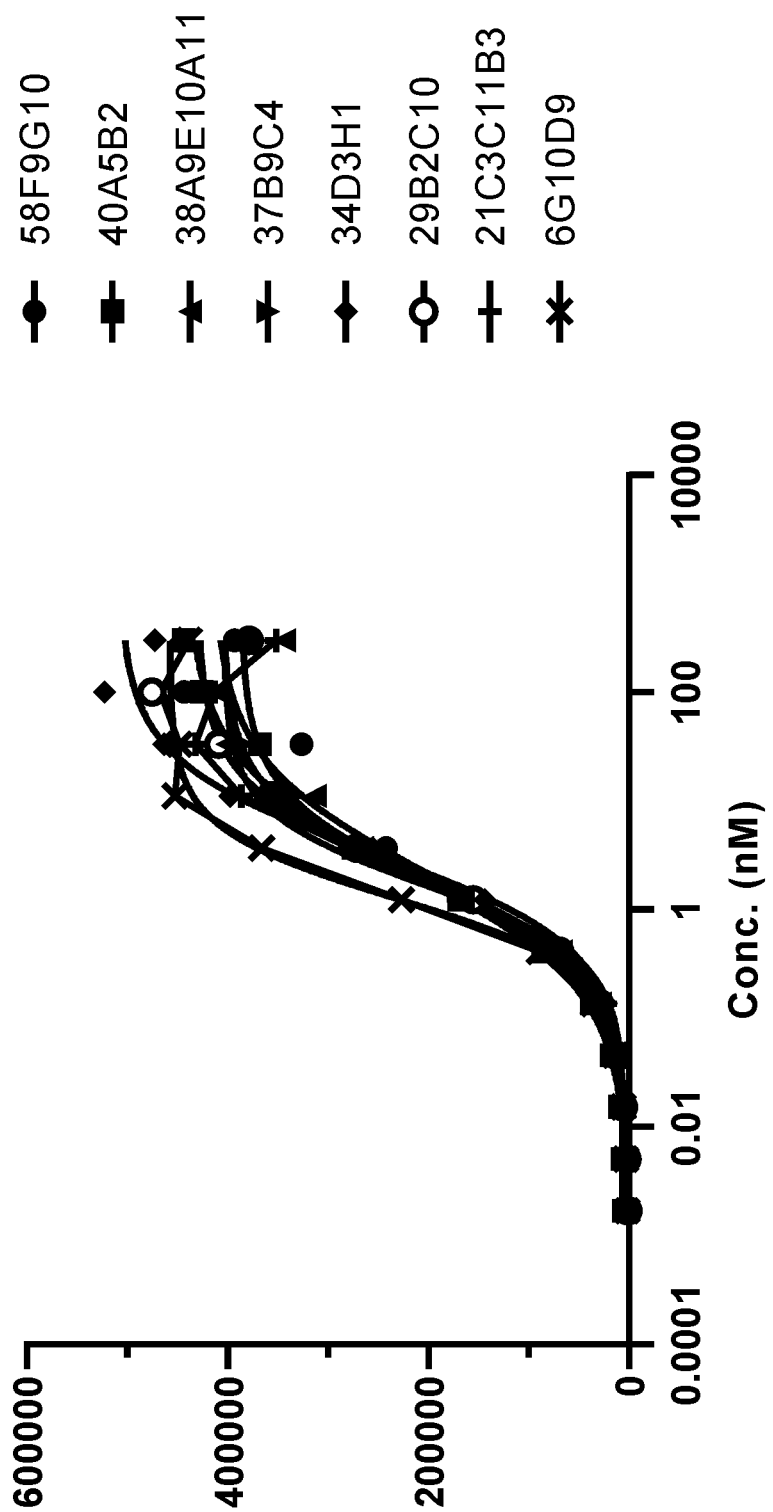
FIG. 2 shows binding of chimeric antibodies to GPRC5D expressed on CHO-K1 cells.

CHO-K1 cells stably expressed human GPRC5D, were harvested from flasks. 100 μl of 1×10⁶ cells/ml of cells were incubated with primary chimeric antibodies in 3-fold serial dilutions starting from 300 nM to 0.001 nM for 30 minutes on ice. After being washed with 200 μl of FACS buffer twice, cells were incubated with secondary antibody for 30 minutes on ice. Cells were washed with 200 μl of FACS buffer twice and transferred to BD Falcon 5 ml tube and analyzed by FACS. The results of the study showed that the chimeric antibodies can bind to human GPRC5D with high EC50 (FIG. 2).

The results are shown in the table below.

|  | Bottom | Top | LogEC50 | HillSlope | EC50 | Span |
|---|---|---|---|---|---|---|
| 58F9G10 | −521.8 | 414579 | 0.3596 | 0.8258 | 2.289 | 415101 |
| 40A5B2 | 1487 | 440269 | 0.3436 | 0.8189 | 2.206 | 438781 |
| 38A9E10A11 | 3016 | 386984 | 0.2453 | 1.037 | 1.759 | 383968 |

-continued

|  | Bottom | Top | LogEC50 | HillSlope | EC50 | Span |
|---|---|---|---|---|---|---|
| 37B9C4 | 2078 | 405062 | 0.249 | 1.045 | 1.774 | 402985 |
| 34D3H1 | 3448 | 507844 | 0.5214 | 1.012 | 3.322 | 504396 |
| 29B2C10 | 4326 | 430443 | 0.342 | 1.041 | 2.198 | 426116 |
| 21C3C11B3 | 5774 | 403938 | 0.2293 | 1.286 | 1.696 | 398164 |
| 6G10D9 | 6886 | 458124 | 0.1012 | 1.343 | 1.262 | 451238 |

Example 3. EC50 of internalization of chimeric GPRC5D antibodies on CHO-GPRC5D cells pHAb Dyes are pH sensor dyes that have very low fluorescence at pH>7 and a dramatic increase in fluorescence as the pH of the solution becomes acidic. pHAb Dyes have excitation maxima (Ex) at 532 nm and emission maxima (Em) at 560 nm. pHAb Dye-conjugated antibodies can be used for monitoring receptor-mediated antibody internalization. When an antibody-pHAb Dye conjugate binds to its receptor on the cell membrane, it exhibits minimal fluorescence. However, upon receptor-mediated internalization, antibody-pHAb Dye conjugates traffic to the endosome and lysosomal vesicles where pH is acidic, causing the pHAb Dye to fluoresce. This fluorescence can be detected using various techniques, including cell imaging, flow cytometry and fluorescent plate-based readers with appropriate filters.

Stably transfected human GPRC5D CHO cells were harvested with 0.05% Trypsin/EDTA (Gibco, 25300-054) and plated in a 96-well black plate (Thermo Scientific #165305) at the density of 10K per 90 µl per well. Plates were incubated for 20-24 h before treatment with pHAb labeled antibodies.

For internalization, pHAb conjugated chimeric GPRC5D antibodies were added to the cells at different and mixed gently for 1-2 min on a plate mixer and then incubated overnight to allow internalization (internalization can be detected in a few hours). Plates were read on a fluorescent plate reader at Ex/Em: 532 nm/560 nm on a Tecan Infinity M1000 Pro. To achieve higher sensitivity, media was replaced by PBS before reading the plate.

Figure 3:
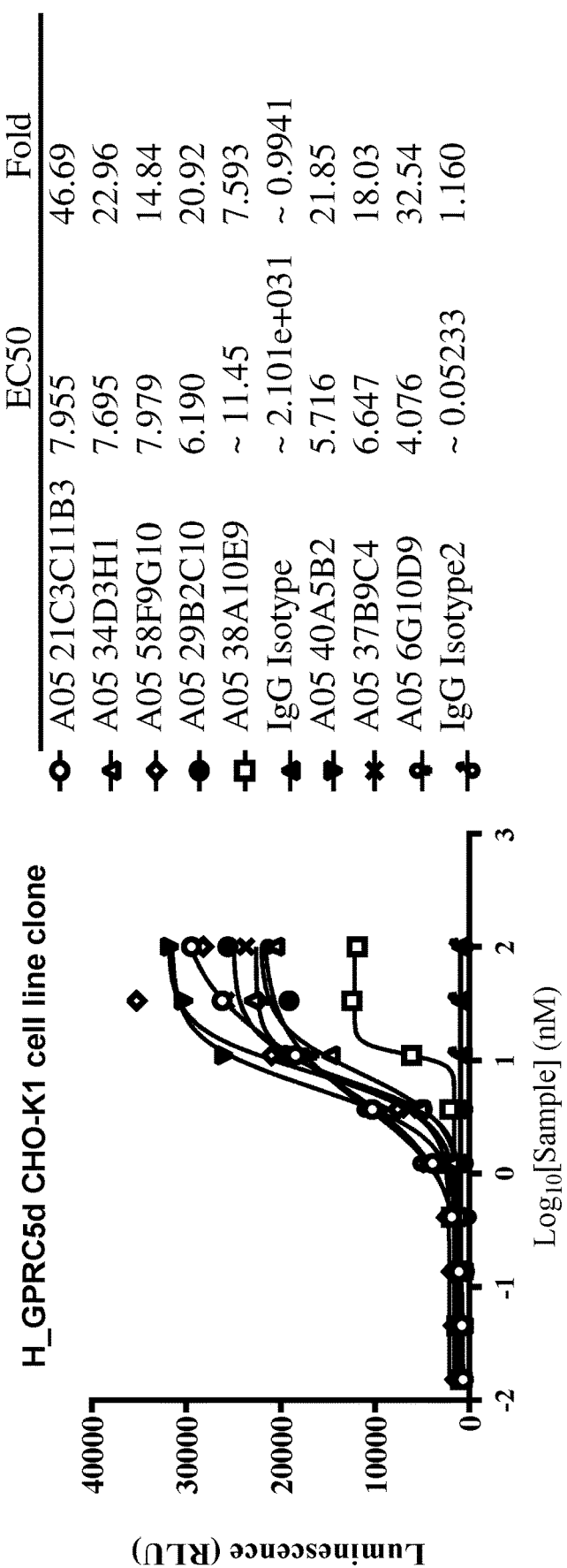
FIG. 3 shows that antibody binding induced endocytosis.

The results normalized with DAR are shown in the FIG. 3. As shown in FIG. 3, the tested chimeric antibodies have potent internalization activity.

Example 4. Testing of Antibody-Dependent Cellular Cytotoxicity (ADCC)

The ADCC Reporter Bioassay uses an alternative readout at an earlier point in ADCC MOA pathway activation: the activation of gene transcription through the NFAT (nuclear factor of activated T-cells) pathway in the effector cell. In addition, the ADCC Reporter Bioassay uses engineered Jurkat cells stably expressing the FcγRIIIa receptor, V158 (high affinity) variant, and an NFAT response element driving expression of firefly luciferase as effector cells. Antibody biological activity in ADCC MOA is quantified through the luciferase produced as a result of NFAT pathway activation; luciferase activity in the effector cell is quantified with luminescence readout. Signal is high, and assay background is low.

Figure 4:
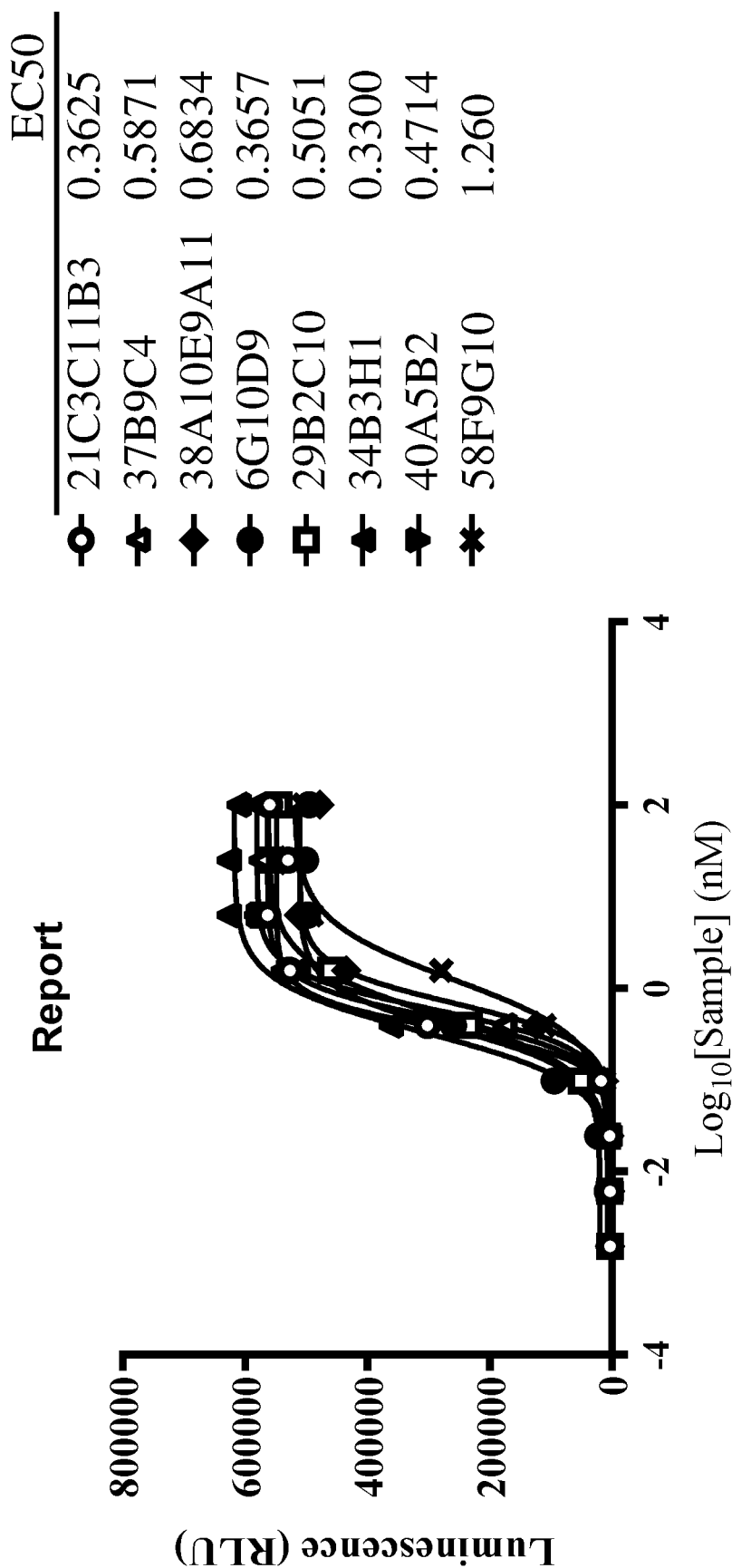
FIG. 4 shows that the antibodies were ADCC-competent.

Serial dilutions of GPRC5D chimeric monoclonal antibody were incubated for 6 hours of induction at 37° C. with engineered Jurkat effector cells (ADCC Bioassay Effector Cells), with or without ADCC Bioassay Target Cells (GPRC5D). Luciferase activity was quantified using Bio-Glo™ Reagent (in FIG. 4). All of the tested antibodies exhibited potent capability in inducing ADCC.

Example 5. Humanization of the mouse mAbs

The murine antibody variable region genes were employed to create humanized mAbs. In the first step of this process, the amino acid sequences of the VH and VL of mAb were compared against the available database of human Ig gene sequences to find the overall best-matching human germline Ig gene sequences.

The amino acid sequences of the humanized antibody are provided below.

Humanized sequences

A. 34D3H1

TABLE 2A

Humanization of 34D3H1 - VH

| Name | Sequence | SEQ ID NO: |
|---|---|---|
| 34D3H1 VH | EVHLVESGGDLVKPGGSLKLSCAASGFTFSSYGMSWVRQTPDKRLEWVAT ISSGGSYTYYPDSVKGRFTISRDNAKNTLNLQMSSLKSEDTAMYYCARQG GDAMDYWGQGTSVTVSS | 7 |
| V1 (CDR grafting) | EVQLVESGGGLVKPGGSLRLSCAASGFTFSSYGMSWVRQAPGKGLEWVST ISSGGSYTYYPDSVKGRFTISRDNAKNSLYLQMNSLRAEDTAVYYCARQG GDAMDYWGQGTLVTVSS | 35 |
| V2 (with back mutations) | EVQLVESGGGLVKPGGSLRLSCAASGFTFSSYGMSWVRQTPGKGLEWVAT ISSGGSYTYYPDSVKGRFTISRDNAKNSLYLQMSSLRAEDTAVYYCARQG GDAMDYWGQGTLVTVSS | 36 |
| V3 (with back mutations) | EVHLVESGGGLVKPGGSLRLSCAASGFTFSSYGMSWVRQTPGKRLEWVAT ISSGGSYTYYPDSVKGRFTISRDNAKNSLNLQMSSLRAEDTAVYYCARQG GDAMDYWGQGTLVTVSS | 37 |

TABLE 2B

| CDR Sequences | | |
|---|---|---|
| CDR | Sequence | SEQ ID NO: |
| CDR-H1 | SYGMS | 29 |
| CDR-H2 | TISSGGSYTYYPDSVKG | 30 |
| CDR-H3 | QGGDAMDY | 31 |

TABLE 2C

| Humanization of 34D3H1-VL | | |
|---|---|---|
| Name | Sequence | SEQ ID NO: |
| 34D3H1 VL | DIVLTQSPATLSVTPGDSVSLSCRASQSINNNLHWYQQKSHESPRLLIKY<br>ASQSISGIPSRFSGSGSGTDFTLSINSVETEDFGMYFCQQSNSRLTFGAG<br>TKLELK | 8 |
| V1 (CDR grafting) | DIQMTQSPSSLSASVGDRVTITCRASQSINNNLHWYQQKPGKAPKLLIYY<br>ASQSISGVPSRFSGSGSGTDFTLTISSLQPEDFATYYCQQSNSRLTFGGG<br>TKVEIK | 38 |
| V2 (with back mutations) | DIQMTQSPSSLSASVGDRVTITCRASQSINNNLHWYQQKPGKAPKLLIYY<br>ASQSIS<u>I</u>PSRFSGSGSGTDFTLTISS<u>V</u>QPEDFATY<u>F</u>CQQSNSRLTFGGG<br>TKVEIK | 39 |
| V3 (with back mutations) | DIQ<u>L</u>TQSPSSLSASVGDRVTITCRASQSINNNLHWYQQKPGK<u>S</u>PKLLIYY<br>ASQSIS<u>I</u>PSRFSGSGSGTDFTLTISS<u>V</u>QPEDFATY<u>F</u>CQQSNSRLTFGGG<br>TK<u>L</u>EIK | 40 |
| V4 (with back mutations) | DI<u>VL</u>TQSPSSLS<u>V</u>SVGDRVT<u>L</u>TCRASQSINNNLHWYQQKPGK<u>S</u>PKLLIYY<br>ASQSIS<u>I</u>PSRFSGSGSGTDFTLTISS<u>V</u>QPEDFATY<u>F</u>CQQSNSRLTFGGG<br>TK<u>L</u>EIK | 41 |

TABLE 2D

| CDR Sequences | | |
|---|---|---|
| CDR | Sequence | SEQ ID NO: |
| CDR-L1 | RASQSINNNLH | 32 |
| CDR-L2 | YASQSIS | 33 |
| CDR-L3 | QQSNSRLT | 34 |

TABLE 2E

| Humanized antibodies | | | | | |
|---|---|---|---|---|---|
| | VL | VL v1 | VL v2 | VL v3 | VL v4 |
| VH 34-XI | | | | | |
| VH v1 | | 34-H1L1 | 34-H1L2 | 34-H1L3 | 34-H1L4 |
| VH v2 | | 34-H2L1 | 34-H2L2 | 34-H2L3 | 34-H2L4 |
| VH v3 | | 34-H3L1 | 34-H3L2 | 34-H3L3 | 34-H3L4 |

B. 37B9C4

TABLE 3A

| Humanization of 37B9C4-VH | | |
|---|---|---|
| Name | Sequence | SEQ ID NO: |
| 37B9C4 VH | EVNLEESGGGLVQPGGSMKLSCVASGFTFSDYWMNWVRQSPEKGLEWVAE<br>IRLKSNNYATHYAESVKGRFTISRDDSKSSVYLQMNNLRAEDTGIYYCTR<br>PLLWFRRYYAMDYWGQGTSVTVSS | 9 |
| V1 (CDR grafting) | EVQLVESGGGLVQPGGSLRLSCAASGFTFSDYWMNWVRQAPGKGLEWVAE<br>IRLKSNNYATHYAESVKGRFTISRDNAKNSLYLQMNSLRAEDTAVYYCAR<br>PLLWFRRYYAMDYWGQGTLVTVSS | 48 |
| V2 (with back mutations) | EVQLVESGGGLVQPGGSLRLSCAASGFTFSDYWMNWVRQ<u>S</u>PGKGLEWVAE<br>IRLKSNNYATHYAESVKGRFTISRDNAK<u>SS</u>LYLQMNSLRAEDTAVYYC<u>TR</u><br>PLLWFRRYYAMDYWGQGTLVTVSS | 49 |
| V3 (with back mutations) | EVQLVESGGGLVQPGGSLRLSCAASGFTFSDYWMNWVRQ<u>S</u>PGKGLEWVAE<br>IRLKSNNYATHYAESVKGRFTISR<u>DSKSSV</u>YLQMNSLRAEDTAVYYC<u>TR</u><br>PLLWFRRYYAMDYWGQGTLVTVSS | 50 |

TABLE 3B

| CDR | Sequence | SEQ ID NO: |
|---|---|---|
| CDR-H1 | DYWMN | 42 |
| CDR-H2 | EIRLKSNNYATHYAESVKG | 43 |
| CDR-H3 | PLLWFRRYYAMDY | 44 |

TABLE 3C

Humanization of 37B9C4-VL

| Name | Sequence | SEQ ID NO: |
|---|---|---|
| 37B9C4 VL | DIQMTQTTSSLSASLGDRITISCSASQGISNYLNWYQQKPDGTVKLLIYY TSSLHSGVPSRFSGSGSGTDYSLTISNLEPADIATYYCQQYSKLPFTFGS GTKLEIK | 10 |
| V1 (CDR grafting) | DIQMTQSPSSLSASVGDRVTITCSASQGISNYLNWYQQKPGKAPKLLIYY TSSLHSGVPSRFSGSGSGTDFTLTISSLQPEDFATYYCQQYSKLPFTFGQ GTKLEIK | 51 |
| V2 (with back mutations) | DIQMTQSPSSLSASVGDRVTITCSASQGISNYLNWYQQKPGKTVKLLIYY TSSLHSGVPSRFSGSGSGTDYTLTISSLQPEDFATYYCQQYSKLPFTFGQ GTKLEIK | 52 |
| V3 (with back mutations) | DIQMTQSPSSLSASVGDRITITCSASQGISNYLNWYQQKPGKTVKLLIYY TSSLHSGVPSRFSGSGSGTDYTLTISSLQPEDFATYYCQQYSKLPFTFGS GTKLEIK | 53 |

TABLE 3D

CDR Sequences

| CDR | Sequence | SEQ ID NO: |
|---|---|---|
| CDR-L1 | SASQGISNYLN | 45 |
| CDR-L2 | YTSSLHS | 46 |
| CDR-L3 | QQYSKLPFT | 47 |

TABLE 3E

Humanized antibodies

|  | VL | VL v1 | VL v2 | VL v3 |
|---|---|---|---|---|
| VH | 37B9C4-XI |  |  |  |
| VH v1 |  | 37-H1L1 | 37-H1L2 | 37-H1L3 |
| VH v2 |  | 37-H2L1 | 37-H2L2 | 37-H2L3 |
| VH v3 |  | 37-H3L1 | 37-H3L2 | 37-H3L3 |

C. 58F9G10

TABLE 4A

Humanization of 58F9G10-VH

| Name | Sequence | SEQ ID NO: |
|---|---|---|
| 58F9G10 VH | EVQLQQSGPELVKTGASVKISCKASGYSFTGYYIHWVKQSHGKSLEWIGY ISCYNGATSFNQKFKGKATFTVDTSSSTAYMQFNSLTSEDSAVYYCARTE LRGPWFAYWGQGTLVTVSA | 15 |
| V1 (CDR grafting) | QVQLVQSGAEVKKPGASVKVSCKASGYSFTGYYIHWVRQAPGQGLEWMGY ISSYNAATSFNQKFKGRVTMTRDTSTSTVYMELSSLRSEDTAVYYCARTE LRGPWFAYWGQGTLVTVSS | 61 |
| V2 (with back mutations) | QVQLVQSGAEVKKPGASVKVSCKASGYSFTGYYIHWVRQAPGQGLEWIGY ISSYNAATSFNQKFKGRVTFTVDTSTSTVYMELSSLRSEDTAVYYCARTE LRGPWFAYWGQGTLVTVSS | 62 |
| V3 (with back mutations) | QVQLVQSGAEVKKPGASVKVSCKASGYSFTGYYIHWVKQAPGQGLEWIGY ISSYNAATSFNQKFKGRVTFTVDTSTSTVYMEFSSLRSEDTAVYYCARTE LRGPWFAYWGQGTLVTVSS | 63 |
| V4 (with back mutations) | QVQLVQSGAEVKKPGASVKISCKASGYSFTGYYIHWVKQAPGQGLEWIGY ISSYNAATSFNQKFKGRATFTVDTSTSTAYMEFSSLRSEDSAVYYCARTE LRGPWFAYWGQGTLVTVSS | 64 |

TABLE 4B

CDR Sequences

| CDR | Sequence | SEQ ID NO: |
| --- | --- | --- |
| CDR-H1 | GYYIH | 54 |
| CDR-H2 | YISCYNGATSFNQKFKG | 60 |
| | YISSYNAATSFNQKFKG | 55 |
| CDR-H3 | TELRGPWFAY | 56 |

TABLE 4C

Humanization of 58F9G10-VL

| Name | Sequence | SEQ ID NO: |
| --- | --- | --- |
| 58F9G10 VL | QTVLTQSPAIMSASPGEKVTMTCSASSSVSYMNWYQQKSGTSPKRWIYDTSKLASGVPARFSGSGSGTSYSLTISSMEAEDAATYYCQQWSNNPLTFGAGTKLELK | 16 |
| V1 (CDR grafting) | DIQMTQSPSSLSASVGDRVTITCSASSSVSYMNWYQQKPGKAPKLLIYDTSKLASGVPSRFSGSGSGTDFTLTISSLQPEDFATYYCQQWSNNPLTFGQGTKLEIK | 65 |
| V2 (with back mutations) | DTQMTQSPSSLSASVGDRVTITCSASSSVSYMNWYQQKPGKAPKRLIYDTSKLASGVPSRFSGSGSGTDYTLTISSLQPEDFATYYCQQWSNNPLTFGQGTKLEIK | 66 |
| V3 (with back mutations) | DTQLTQSPSSLSASVGDRVTMTCSASSSVSYMNWYQQKPGKAPKRLIYDTSKLASGVPSRFSGSGSGTDYTLTISSMQPEDFATYYCQQWSNNPLTFGQGTKLEIK | 67 |

TABLE 4D

CDR Sequences

| CDR | Sequence | SEQ ID NO: |
| --- | --- | --- |
| CDR-L1 | SASSSVSYMN | 57 |
| CDR-L2 | DTSKLAS | 58 |
| CDR-L3 | QQWSNNPLT | 59 |

TABLE 3E

Humanized antibodies

| | VL | VL v1 | VL v2 | VL V3 |
| --- | --- | --- | --- | --- |
| VH | 58F9G10-XI | | | |
| VH v1 | | 58-H1L1 | 58-H1L2 | 58-H1L3 |
| VH v2 | | 58-H2L1 | 58-H2L2 | 58-H2L3 |
| VH v3 | | 58-H3L1 | 58-H3L2 | 58-H3L3 |
| VH v4 | | 58-H4L1 | 58-H4L2 | 58-H4L3 |

D. 6G10D9

TABLE 5A

Humanization of 6G10D9-VH

| Name | Sequence | SEQ ID NO: |
| --- | --- | --- |
| 6G10D9 VH | QVQLQQSGAELARPGASVKMSCKASGYTFTTYTMHWVKQRPGQGLEWLGYINPSSGYTNYNQKFKDKATLTAGKSSSTAYMQLSSLTSEDSAVYYCASLRSRGYFDYWGQGTTLTVSS | 1 |
| V1 (CDR grafting) | QVQLVQSGAEVKKPGASVKVSCKASGYTFTTYTMHWVRQAPGQGLEWMGYINPSSGYTNYNQKFKDRVTMTRDTSTSTVYMELSSLRSEDTAVYYCSRLRSRGYFDYWGQGTLVTVSS | 74 |
| V2 (with back mutations) | QVQLVQSGAEVKKPGASVKVSCKASGYTFTTYTMHWVRQAPGQGLEWLGYINPSSGYTNYNQKFKDRVTMTADTSTSTVYMELSSLRSEDTAVYYCARLRSRGYFDYWGQGTLVTVSS | 75 |
| V3 (with back mutations) | QVQLVQSGAEVAKPGASVKVSCKASGYTFTTYTMHWVKQAPGQGLEWLGYINPSSGYTNYNQKFKDRVTMTADTSTSTVYMELSSLRSEDTAVYYCASLRSRGYFDYWGQGTLVTVSS | 76 |
| V4 (with back mutations) | QVQLVQSGAEVAKPGASVKMSCKASGYTFTTYTMHWVKQAPGQGLEWLGYINPSSGYTNYNQKFKDRVTLT ADTSTSTVYMELSSLRSEDTAVYYCASLRSRGYFDYWGQGTLLTVSS | 77 |

TABLE 5A-continued

Humanization of 6G10D9-VH

| Name | Sequence | SEQ ID NO: |
|---|---|---|
| V5 (with back mutations) | QVQLQQSGAEVAKPGASVKMSCKASGYTFTTYTMHWVKQRPGQGLEWLGY INPSSGYTNYNQKFKDRVTLTADKSTSTVYMELSSLRSEDTAVYYCASLR SRGYFDYWGQGTLL**TVSS | 78 |
| V6 (with back mutations) | QVQLQQSGAEVAKPGASVKMSCKASGYTFTTYTMHWVKQRPGQGLEWLGY INPSSGYTNYNQKFKDRATLTAGKSTSTVYMELSSLRSEDTAVYYCASLR SRGYFDYWGQGTLL**TVSS | 79 |

TABLE 5B

CDR Sequences

| CDR | Sequence | SEQ ID NO: |
|---|---|---|
| CDR-H1 | TYTMH | D01 |
| CDR-H2 | YINPSSGYTNYNQKFKD | D02 |
| CDR-H3 | LRSRGYFDY | D03 |

TABLE 5D

CDR Sequences

| CDR | Sequence | SEQ ID NO: |
|---|---|---|
| CDR-L1 | KASQNVGTAVV | 71 |
| CDR-L2 | SASNRYT | 72 |
| CDR-L3 | QQYSSYPYT | 73 |

TABLE 5C

Humanization of 6G10D9-VL

| Name | Sequence | SEQ ID NO: |
|---|---|---|
| 6G10D9 VL | DIVMTQSQTFMSTSVGDRVRITCKASQNVGTAVVWYQQKTGQSPRLLIYS ASNRYTGVPDRFTGSGSGTDFTLTISNMQSEDLADFFCQQYSSYPYTFGG GTKLEIK | 2 |
| V1 (CDR grafting) | DIQLTQSPSFLSASVGDRVTITCKASQNVGTAVVWYQQKPGKAPKLLIYS ASNRYTGVPSRFSGSGSGTEFTLTISSLQPEDFATYYCQQYSSYPYTFGQ GTKLEIK | 80 |
| V2 (with back mutations) | DIQLTQSPSFLSTSVGDRVTITCKASQNVGTAVVWYQQKPGKSPKLLIYS ASNRYTGVPSRFSGSGSGTEFTLTISSLQPEDFATFYCQQYSSYPYTFGQ GTKLEIK | 81 |
| V3 (with back mutations) | DIQMTQSPSFLSTSVGDRVTITCKASQNVGTAVVWYQQKPGKSPKLLIYS ASNRYTGVPSRFSGSGSGTEFTLTISSMQPEDFATFFCQQYSSYPYTFGQ GTKLEIK | 82 |
| V4 (with back mutations) | DIVMTQSPSFLSTSVGDRVTITCKASQNVGTAVVWYQQKPGKSPKLLIYS ASNRYTGVPDRFSGSGSGTEFTLTISSMQPEDFATFFCQQYSSYPYTFGG GTKLEIK | 83 |
| V1a (CDR grafting version a) | EIVMTQSPATLSVSPGERATLSCKASQNVGTAVVWYQQKPGQAPRLLIYS ASNRYTGIPARFSGSGSGTEFTLTISSLQSEDFAVYYCQQYSSYPYTFGQ GTKLEIK | 84 |
| V2a (with back mutations) | EIVMTQSPATLSTSPGERATLSCKASQNVGTAVVWYQQKPGQSPRLLIYS ASNRYTGIPDRFSGSGSGTEFTLTISSLQSEDFAVFFCQQYSSYPYTFGQ GTKLEIK | 85 |
| V3a (with back mutations) | EIVMTQSPATLSTSPGERVTISCKASQNVGTAVVWYQQKPGQSPRLLIYS ASNRYTGIPDRFTGSGSGTDFTLTISSMQSEDFAVFFCQQYSSYPYTFGG GTKLEIK | 86 |

TABLE 5E

| | VL | VL v1 | VL v2 | VL v3 | VL v4 | VL v1a | VL v2a | VL v3a |
|---|---|---|---|---|---|---|---|---|
| VH | 6G10D9-XI | | | | | | | |
| VH v1 | | 6-H1L1 | 6-H1L2 | 6-H1L3 | | | | |
| VH v2 | | 6-H2L1 | 6-H2L2 | 6-H2L3 | | | | |
| VH v3 | | 6-H3L1 | 6-H3L2 | 6-H3L3 | | | | |
| VH v4 | | 6-H4L1 | 6-H4L2 | 6-H4L3 | | | | |
| VH v5 | | | | | | | | |
| VH v6 | | | | | | | | |

Humanized antibodies

Example 6. Testing of Humanized Antibodies

This example tested some of the humanized antibodies for the ability to bind to GPRC5D expressed on CHO-K1 cells.

Figure 5:
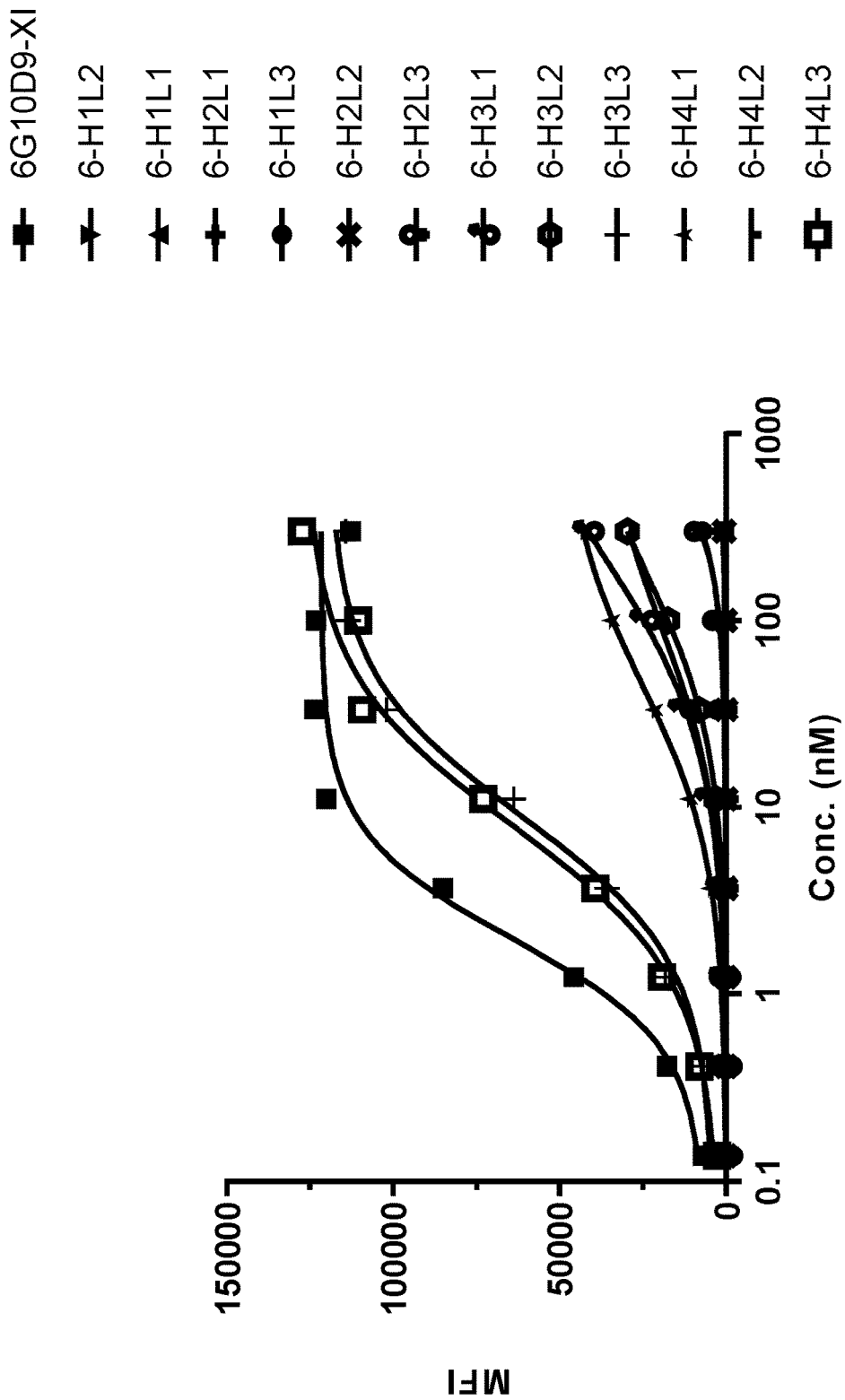
FIG. 5-8 show the affinity testing results of the humanized antibodes derived from 6G10D9, 58F9G10, 34D3H1, and 37B9C4, respectively.

Out of the tested humanized antibodies derived from 6G10D9, 6-H2L1 and 6-H3L3 outperformed others (FIG. 5, Table 6).

TABLE 6

Activities of humanized antibodies of 6G10D9 to bind GPRC5D

| | Bottom | Top | LogEC50 | HillSlope | EC50 | Span |
|---|---|---|---|---|---|---|
| 6G1009-X1 | 6858 | 121725 | 0.2992 | 1.525 | 1.991 | 114867 |
| 6-H1L1 | 192.6 | ~6397 | ~3.102 | 1.198 | ~1264 | ~6205 |
| 6-H1L2 | 191.9 | 898894 | 5.224 | 1.19 | 167639 | 898702 |
| 6-H1L3 | 226.2 | 16478302 | 5.389 | 1.156 | 244790 | 16478076 |
| 6-H2L1 | 189.1 | 661560 | 5.039 | 1.232 | 109294 | 661371 |
| 6-H2L2 | 192.5 | 1271084 | 5.37 | 1.191 | 234364 | 1270892 |
| 6-H2L3 | 215.7 | 10592380 | 5.039 | 1.23 | 109279 | 10592164 |
| 6-H3L1 | −205.1 | 74293 | 2.352 | 0.8392 | 225.1 | 74498 |
| 6-H3L2 | 68.94 | 47463 | 2.244 | 0.9532 | 175.3 | 47394 |
| 6-H3L3 | 3994 | 119304 | 0.9553 | 1.13 | 9.022 | 115310 |
| 6-H4L1 | 61.5 | 50293 | 1.654 | 0.9277 | 45.05 | 50231 |
| 6-H4L2 | 9.56 | 39449 | 1.976 | 0.911 | 94.63 | 39440 |
| 6-H4L3 | 2344 | 126413 | 0.9049 | 1.052 | 8.033 | 124069 |

Figure 6:
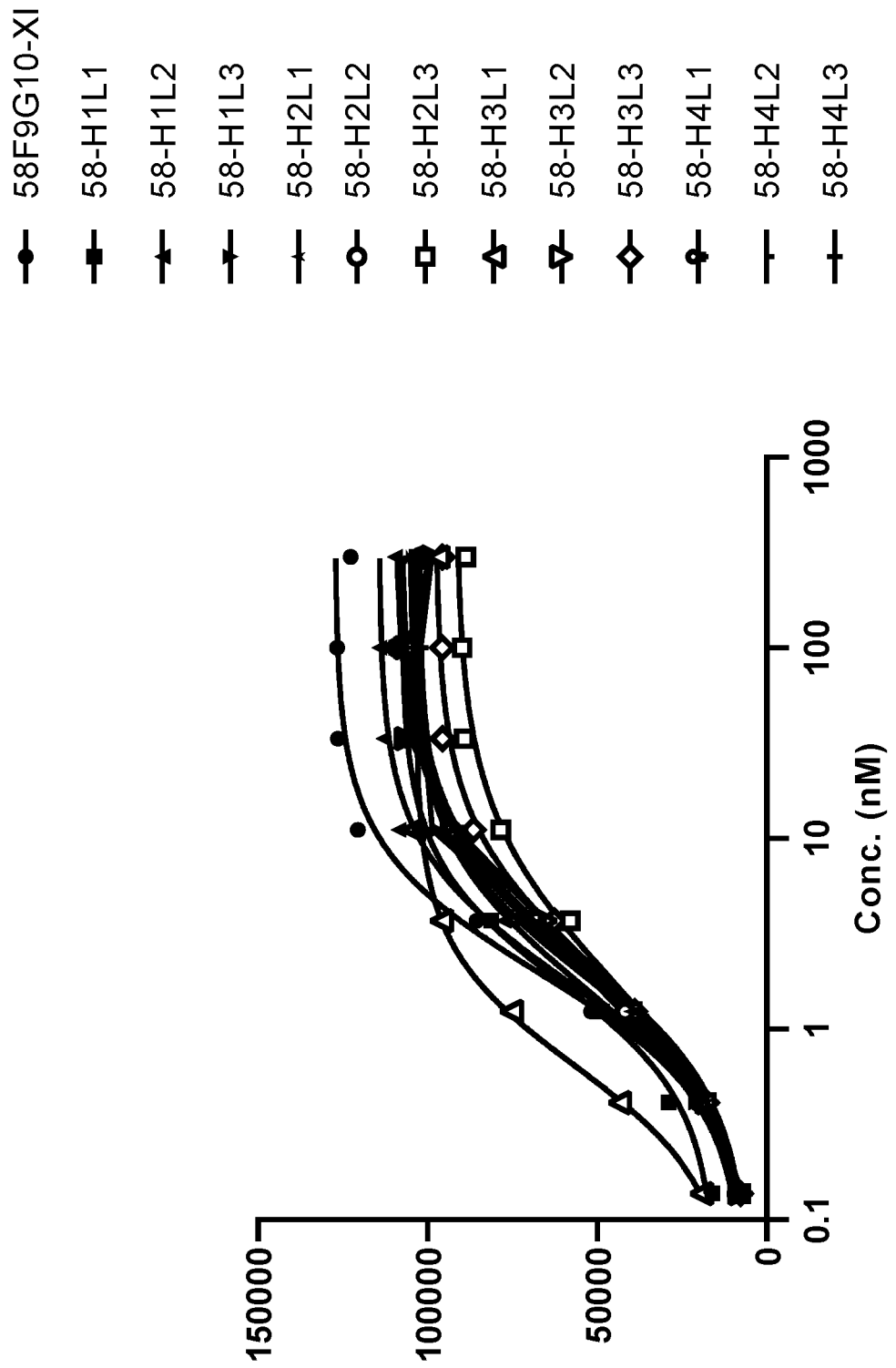

As shown in FIG. 6 and Table 7, all of the humanized versions of 58F9G10 appeared to have good performance.

TABLE 7

Activities of humanized antibodies of 58F9G10 to bind GPRC5D

| | Bottom | Top | LogEC50 | HillSlope | EC50 | Span |
|---|---|---|---|---|---|---|
| 58F9G10-XI | 6697 | 127349 | 0.2925 | 1.292 | 1.961 | 120652 |
| 58-H1L1 | 15047 | 107881 | 0.2519 | 1.342 | 1.786 | 92834 |
| 58-H1L2 | 5500 | 114432 | 0.2632 | 1.238 | 1.833 | 108932 |
| 58-H1L3 | 4227 | 105346 | 0.2308 | 1.14 | 1.701 | 101119 |
| 58-H2L1 | 3617 | 109672 | 0.3776 | 1.064 | 2.386 | 106055 |
| 58-H2L2 | 4837 | 107888 | 0.3448 | 1.091 | 2.212 | 103050 |
| 58-H2L3 | 1229 | 91713 | 0.2697 | 0.9633 | 1.861 | 90483 |
| 58-H3L1 | 9887 | 103663 | −0.1918 | 1.382 | 0.643 | 93776 |
| 58-H3L2 | 5981 | 105458 | 0.3742 | 1.195 | 2.367 | 99476 |
| 58-H3L3 | 4022 | 97718 | 0.3177 | 1.105 | 2.078 | 93695 |
| 58-H4L1 | 4993 | 104559 | 0.3655 | 1.179 | 2.32 | 99566 |
| 58-H4L2 | 4600 | 105051 | 0.3407 | 1.143 | 2.191 | 100451 |
| 58-H4L3 | 6249 | 102650 | 0.2874 | 1.27 | 1.938 | 96401 |

Figure 7:
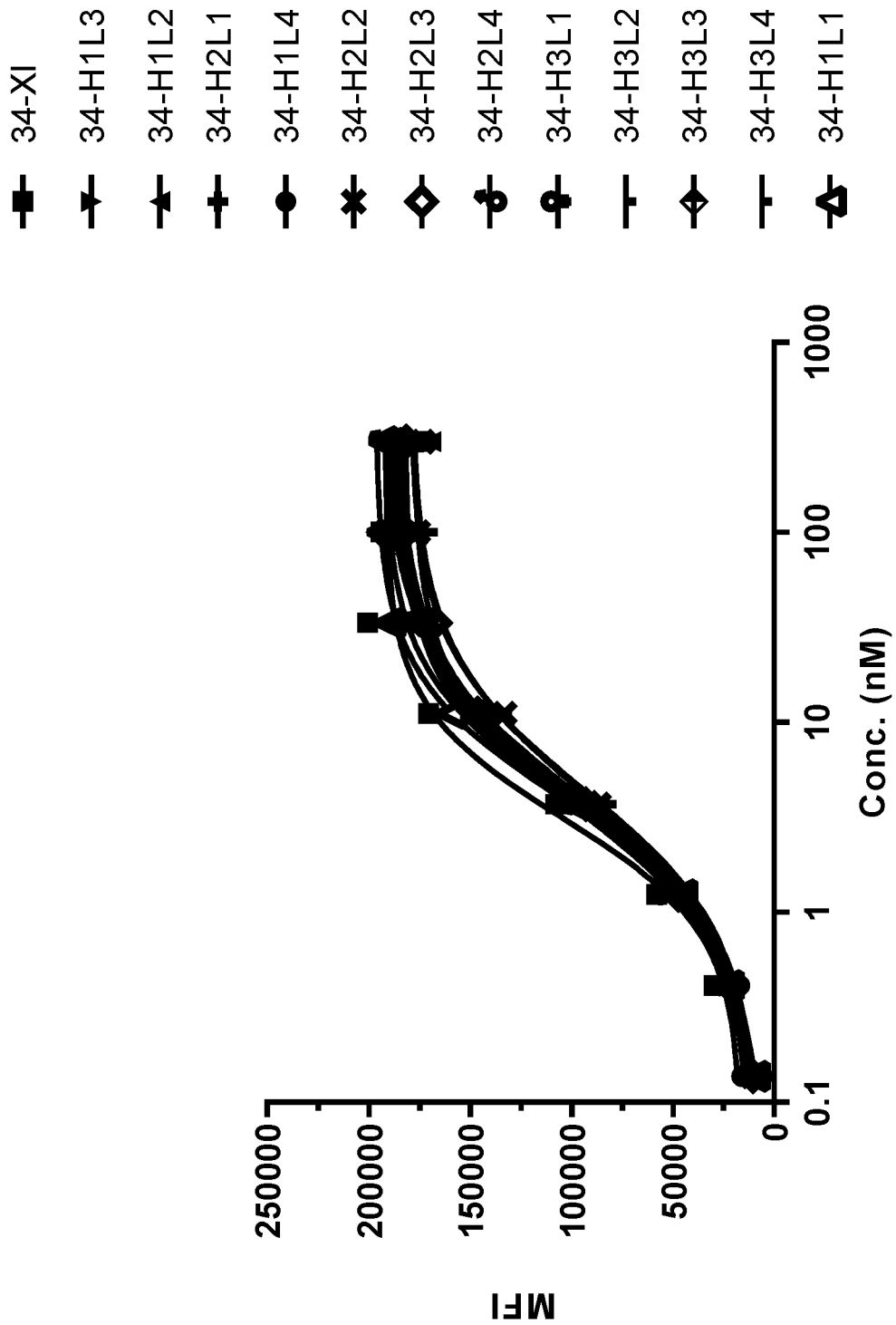

Likewise, as shown in FIG. 7 and Table 8, all of the humanized versions of 34D3H1 appeared to have good performance, comparable to the chimeric antibody.

TABLE 8

Activities of humanized antibodies of 34D3H1 to bind GPRC5D

| | Bottom | Top | LogEC50 | HillSlope | EC50 | Span |
|---|---|---|---|---|---|---|
| 34-XI | 16525 | 192054 | 0.4947 | 1.454 | 3.124 | 175530 |
| 34-H1L1 | 10921 | 196570 | 0.5908 | 1.314 | 3.898 | 185650 |

TABLE 8-continued

Activities of humanized antibodies of 34D3H1 to bind GPRC5D

| | Bottom | Top | LogEC50 | HillSlope | EC50 | Span |
|---|---|---|---|---|---|---|
| 34-H1L2 | 13856 | 182030 | 0.5836 | 1.436 | 3.834 | 168174 |
| 34-H1L3 | 10620 | 185840 | 0.5732 | 1.167 | 3.743 | 175220 |
| 34-H1L4 | 10299 | 188925 | 0.5999 | 1.195 | 3.98 | 178626 |
| 34-H2L1 | 7854 | 187153 | 0.6188 | 1.173 | 4.157 | 179298 |
| 34-H2L2 | 8736 | 178873 | 0.6254 | 1.118 | 4.221 | 170137 |
| 34-H2L3 | 7063 | 185842 | 0.5832 | 1.11 | 3.83 | 178779 |
| 34-H2L4 | 4393 | 192405 | 0.6092 | 1.041 | 4.066 | 188012 |
| 34-H3L1 | 11139 | 178248 | 0.5207 | 1.228 | 3.317 | 167109 |
| 34-H3L2 | 9036 | 179809 | 0.6464 | 1.146 | 4.43 | 170773 |
| 34-H3L3 | 9118 | 192976 | 0.6508 | 1.1 | 4.475 | 183858 |
| 34-H3L4 | 12751 | 192533 | 0.5981 | 1.263 | 3.963 | 179782 |

Figure 8:
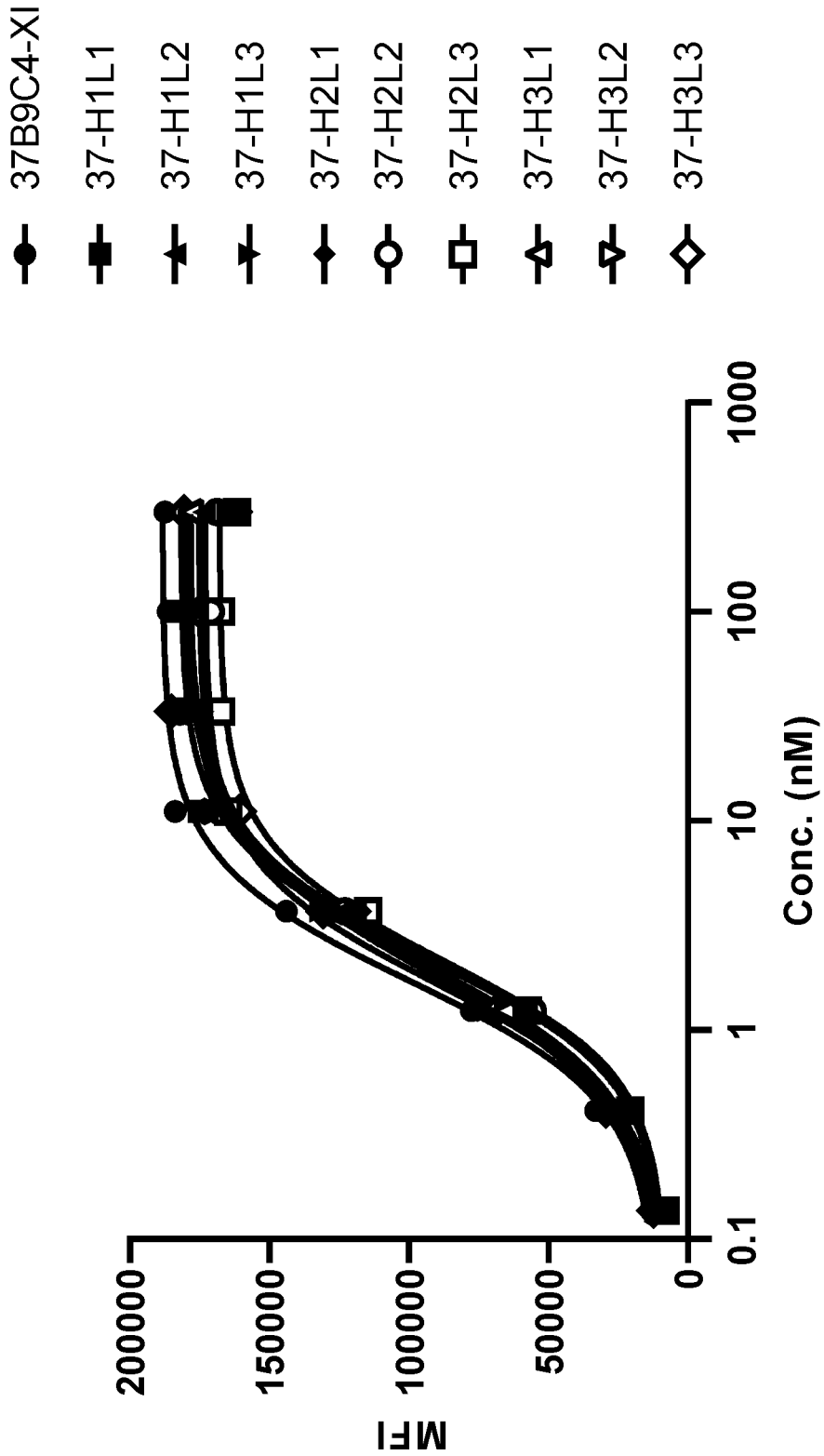

Also, as shown in FIG. 8 and Table 9, all of the humanized versions of 37B9C4 appeared to have good performance, comparable to the chimeric counterpart.

TABLE 9

Activities of humanized antibodies of 37B9C4 to bind GPRC5D

| | Bottom | Top | LogEC50 | HillSlope | EC50 | Span |
|---|---|---|---|---|---|---|
| 37B9C4-XI | 11711 | 188479 | 0.2364 | 1.502 | 1.723 | 176769 |
| 37-H1L1 | 9596 | 178413 | 0.3574 | 1.613 | 2.277 | 168817 |
| 37-H1L2 | 8848 | 181865 | 0.3502 | 1.534 | 2.24 | 173017 |

TABLE 9-continued

Activities of humanized antibodies of 37B9C4 to bind GPRC5D

|  | Bottom | Top | LogEC50 | HillSlope | EC50 | Span |
|---|---|---|---|---|---|---|
| 37-H1L3 | 10445 | 173229 | 0.2332 | 1.528 | 1.711 | 162784 |
| 37-H2L1 | 9184 | 175072 | 0.351 | 1.583 | 2.244 | 165888 |
| 37-H2L2 | 9383 | 175293 | 0.3455 | 1.656 | 2.216 | 165910 |
| 37-H3L1 | 8049 | 168032 | 0.3334 | 1.564 | 2.155 | 159982 |
| 37-H3L1 | 6372 | 179261 | 0.2921 | 1.35 | 1.96 | 172889 |
| 37-H3L2 | 9193 | 179304 | 0.3153 | 1.428 | 2.067 | 170111 |
| 37-H3L3 | 7780 | 181053 | 0.2846 | 1.305 | 1.926 | 173273 |

Based on the above data, humanized antibodies 6-H3L3, 6-H4L3, 58-H1L1, 58-H3L1, 34-H1L1 and 37-H1L1 were selected for further confirmative testing.

Example 7. Confirmative Testing of Select Humanized Antibodies

This example tested some of the humanized antibodies (6-H3L3, 6-H4L3, 58-H1L1, 58-H3L1, 34-H1L1 and 37-H1L1) for their ability to bind to the human GPRC5D protein expressed on CHO-K1 and NCI-H929 cells.

Figure 9:
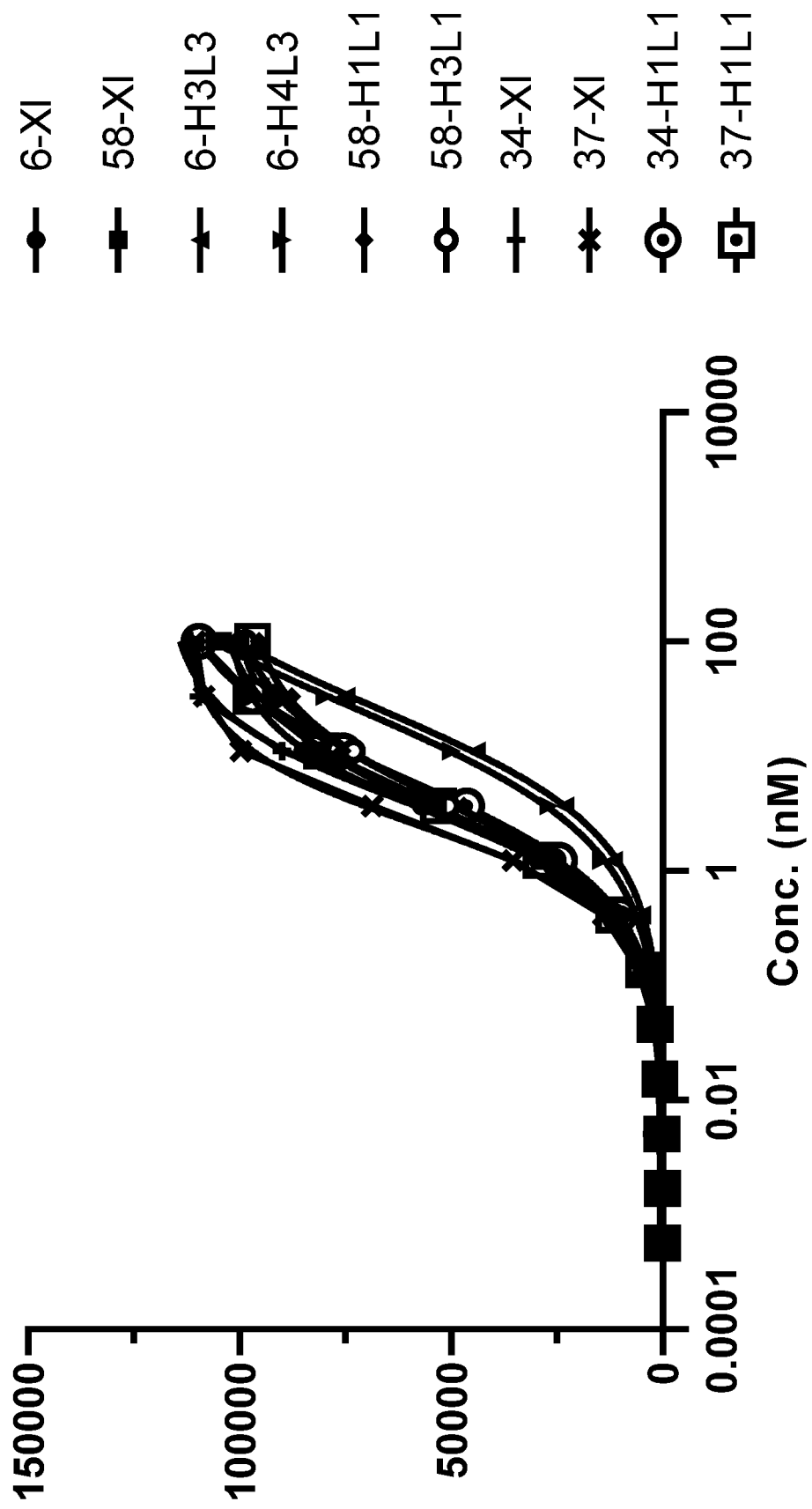
FIG. 9 confirms the binding of selected humanized antibodies to GPRC5D expressed on CHO-K1 cells.
Figure 10:
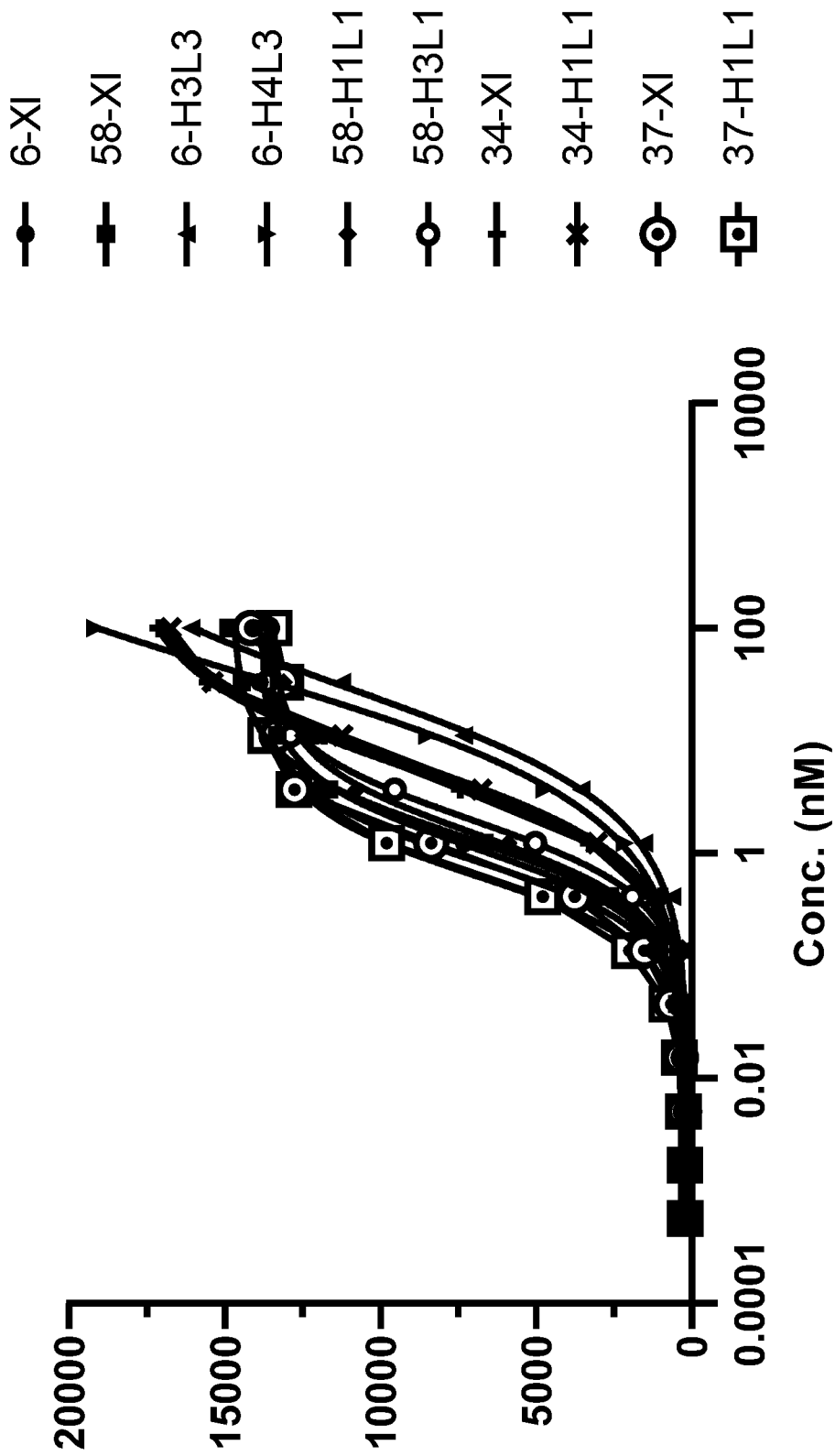
FIG. 10 confirms the binding of selected humanized antibodies to GPRC5D expressed on NCI-H929 cells.

The binding data to CHO-K1 are charted in FIG. 9 and summarized in Table 10 below.

TABLE 10

Binding to GPRC5D on CHO-K1 cells

|  | Bottom | Top | LogEC50 | HillSlope | EC50 | Span |
|---|---|---|---|---|---|---|
| 6-XI | 523.9 | 104077 | 0.4723 | 1.095 | 2.967 | 103553 |
| 58-XI | 52.25 | 107000 | 0.5562 | 0.9481 | 3.599 | 106948 |
| 6-H3L3 | 172 | 134045 | 1.412 | 0.8045 | 25.82 | 133873 |
| 6-H4L3 | 109.4 | 145833 | 1.421 | 0.7392 | 26.34 | 145724 |
| 58-H1L1 | 275.4 | 99454 | 0.579 | 0.972 | 3.793 | 99178 |
| 58-H3L1 | 75.37 | 104402 | 0.612 | 0.9135 | 4.093 | 104326 |
| 34-XI | 688.6 | 117714 | 0.5776 | 1.054 | 3.781 | 117025 |
| 37-XI | 792.6 | 113379 | 0.3877 | 1.175 | 2.442 | 112586 |
| 34-H1L1 | 170.8 | 119038 | 0.781 | 0.8745 | 6.04 | 118867 |
| 37-H1L1 | 523.2 | 102496 | 0.511 | 1.042 | 3.244 | 101973 |

TABLE 11

Binding to GPRC5D on NCI-H929 cells

|  | Bottom | Top | LogEC50 | HillSlope | EC50 | Span |
|---|---|---|---|---|---|---|
| 6-XI | 269.4 | 13785 | 0.05146 | 1.313 | 1.126 | 13515 |
| 58-XI | 261.4 | 14738 | 0.1596 | 1.269 | 1.444 | 14476 |
| 6-H3L3 | 129.8 | 21859 | 1.465 | 0.8063 | 29.18 | 21730 |
| 6-H4L3 | 80.05 | 28987 | 1.606 | 0.7142 | 40.33 | 28907 |
| 58-H1L1 | 281 | 13474 | 0.1648 | 1.319 | 1.462 | 13193 |
| 58-H3L1 | 275.5 | 13934 | 0.3 | 1.297 | 1.995 | 13658 |
| 34-XI | 181.1 | 18146 | 0.7587 | 0.9911 | 5.738 | 17965 |
| 34-H1L1 | 199.3 | 17911 | 0.8048 | 1.011 | 6.379 | 17712 |
| 37-XI | 337.6 | 13807 | −0.05621 | 1.41 | 0.8786 | 13470 |
| 37-H1L1 | 341.8 | 13534 | −0.1991 | 1.419 | 0.6323 | 13192 |

These data, therefore, confirm that these selected humanized antibodies are suitable for further clinical development.

Example 8. ADCC of Humanized Antibodies

The ADCC Reporter Bioassay uses an alternative readout at an earlier point in ADCC MOA pathway activation: the activation of gene transcription through the NFAT (nuclear factor of activated T-cells) pathway in the effector cell. In addition, the ADCC Reporter Bioassay uses engineered Jurkat cells stably expressing the FcγRIIIa receptor, V158 (high affinity) variant, and an NFAT response element driving expression of firefly luciferase as effector cells. Antibody biological activity in ADCC MOA is quantified through the luciferase produced as a result of NFAT pathway activation; luciferase activity in the effector cell is quantified with luminescence readout. Signal is high, and assay background is low.

Serial dilutions of GPRC5D hu Abs were incubated for 6 hours of induction at 37° C. with engineered Jurkat effector cells (ADCC Bioassay Effector Cells), with ADCC Bioassay Target Cells (expressing GPRC5D). Luciferase activity was quantified using Bio-Glo™ TM Reagent.

Figure 11:
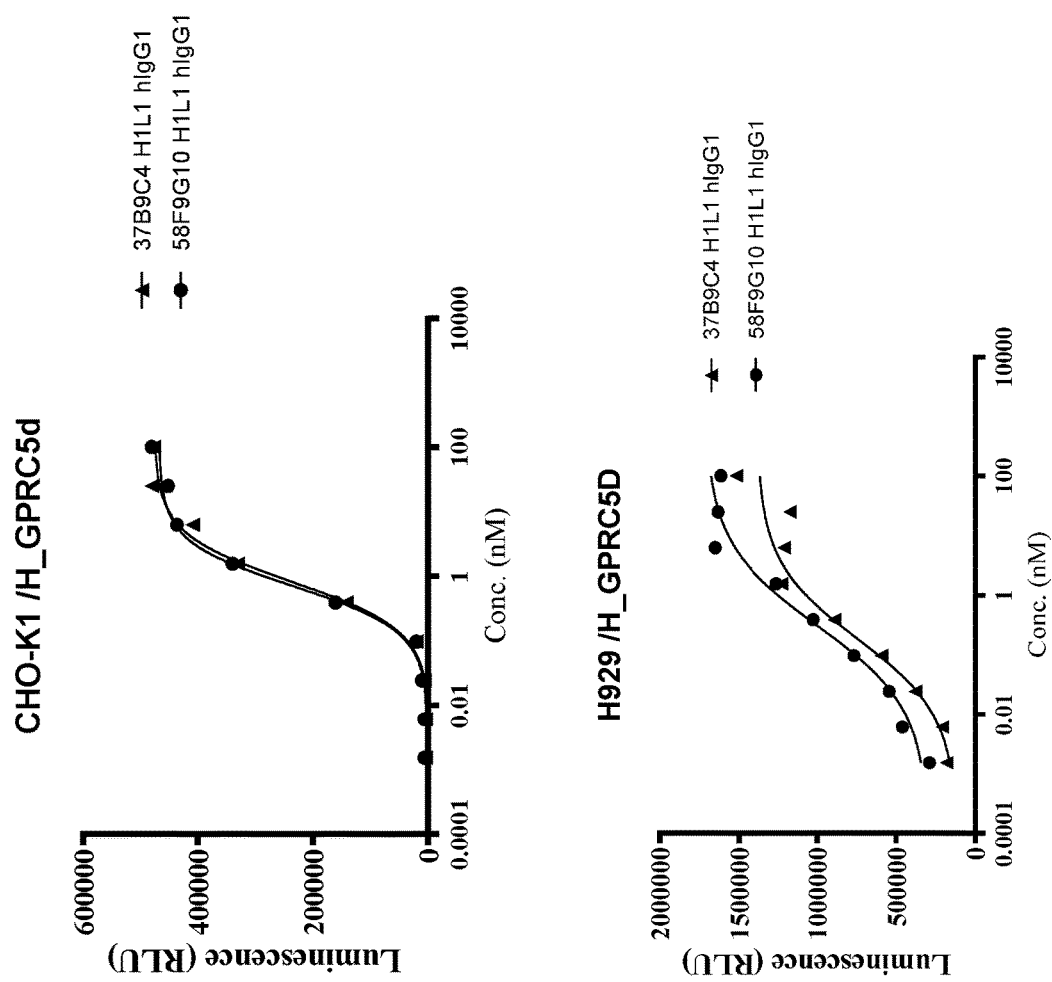
FIG. 11 shows the ADCC efficacy of tested humanized antibodies.
Figure 11:
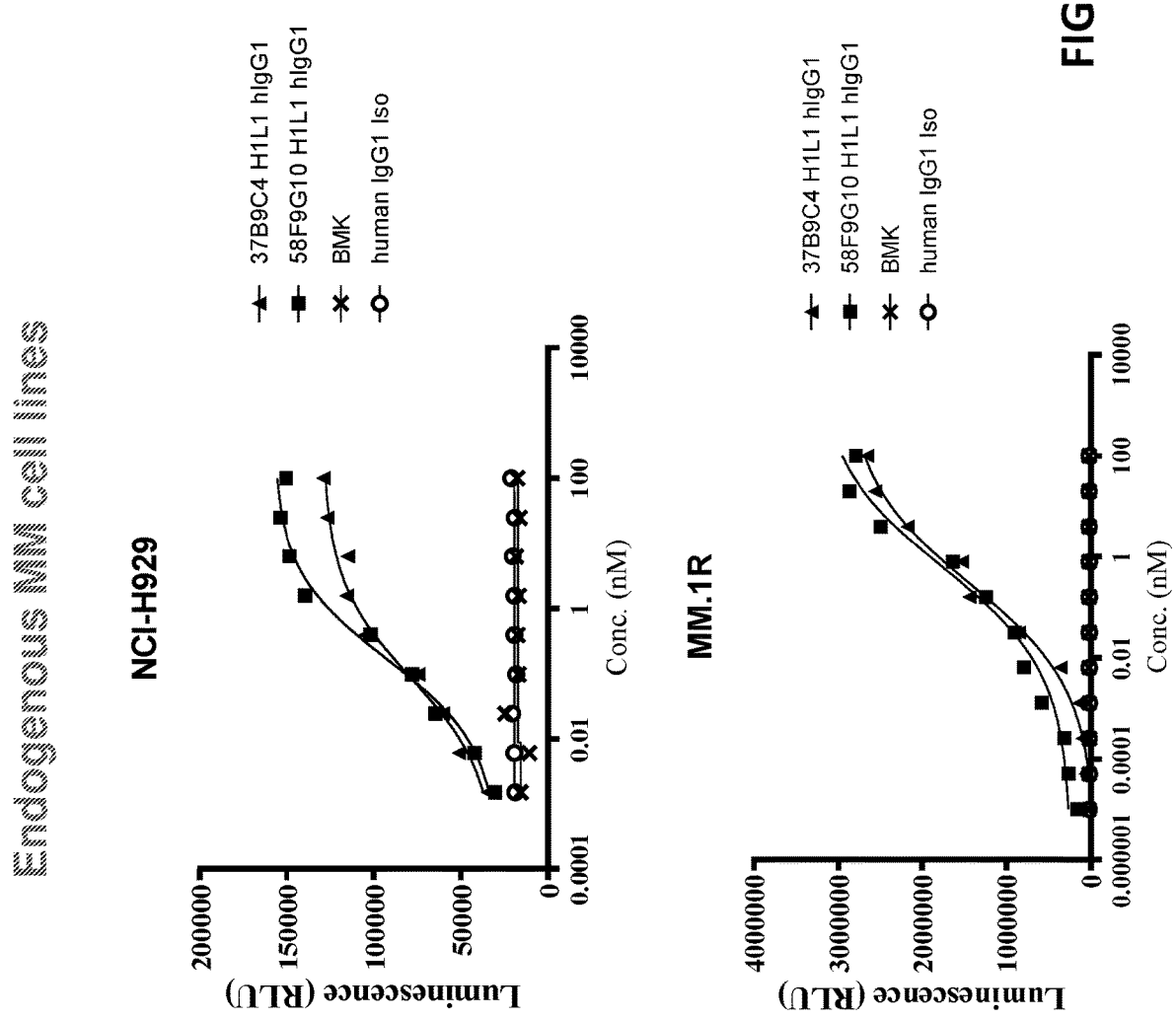

The results are presented in FIG. 11, which shows that these humanized antibodies induced strong ADCC activities on GPRC5D-overexpressing cell lines and endogenous MM (multiple myeloma) cell lines.

Example 9. Internalization of Humanized Antibodies

This example tested the humanized antibodies for their internationalization induction activities. The example used a new hydrophilic and bright pH sensor dye (pHAb dye), which is not fluorescent at neutral pH but becomes highly fluorescent at acidic pH with internalization. It can be used to detect the process of internalization. NCI-H929 and MM.1R cells endogenously expressed human GPRC5D as the target cells, the detection antibody labeled with pHAb dye was added to evaluate the internalization of GPRC5D hu antibody in vitro.

Figure 12:
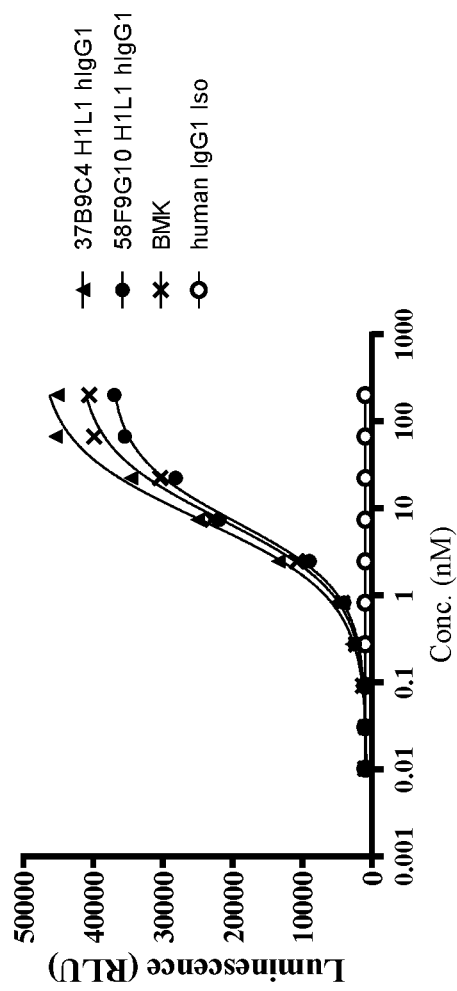
FIG. 12 shows the internalization induction activity of the tested humanized antibodies.
Figure 12:
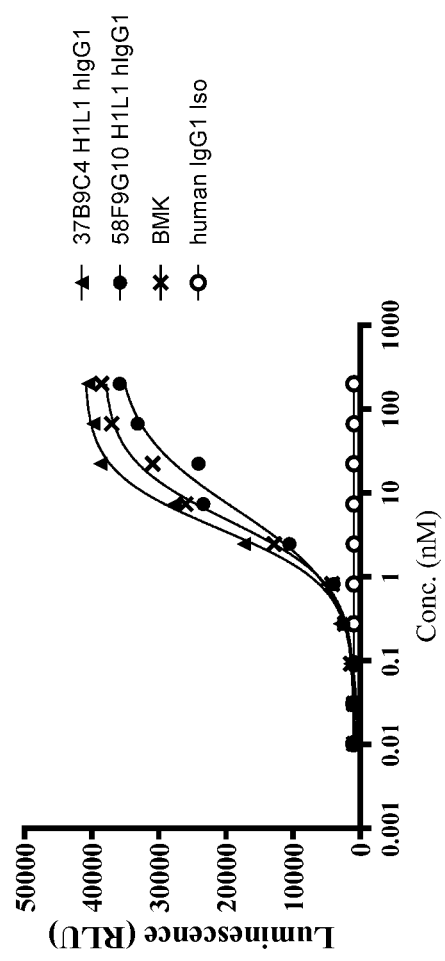
Figure 12:
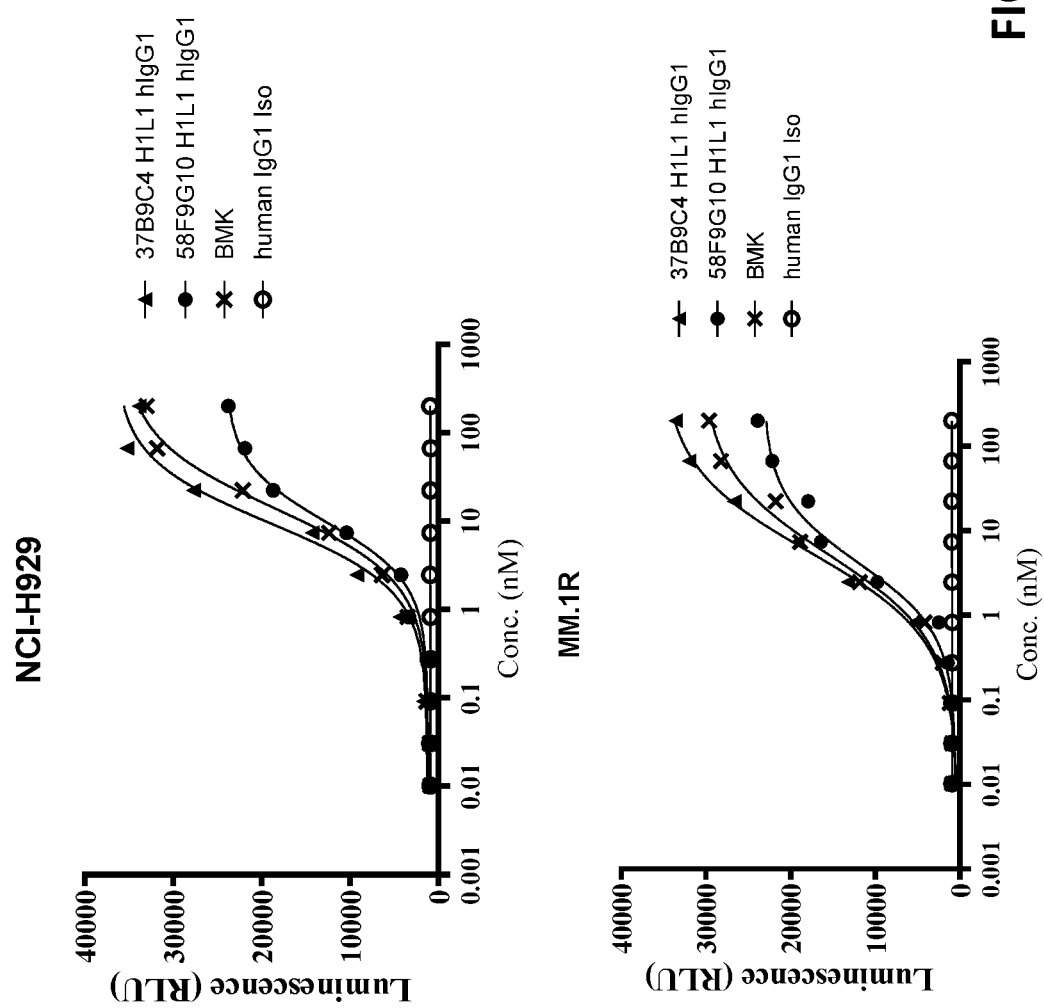

Serial dilutions of GPRC5D hu antibodies were incubated for 24 hours at 37° C. Luciferase activity was detected. The results, in FIG. 12, show that these humanized antibodies have very strong internalization activities to both GPRC5D-overexpressing cell lines and endogenous MM cell lines.

Example 10. Killing Activity of GPRC5D ADC

This example tested two antibody-drug conjugates (ADC) for their killing activities of targeted cells. These ADC included 37B9C4 and 58F9G10, respectively, conjugated to the toxic drug Monomethyl auristatin E (MMAE).

Figure 13:
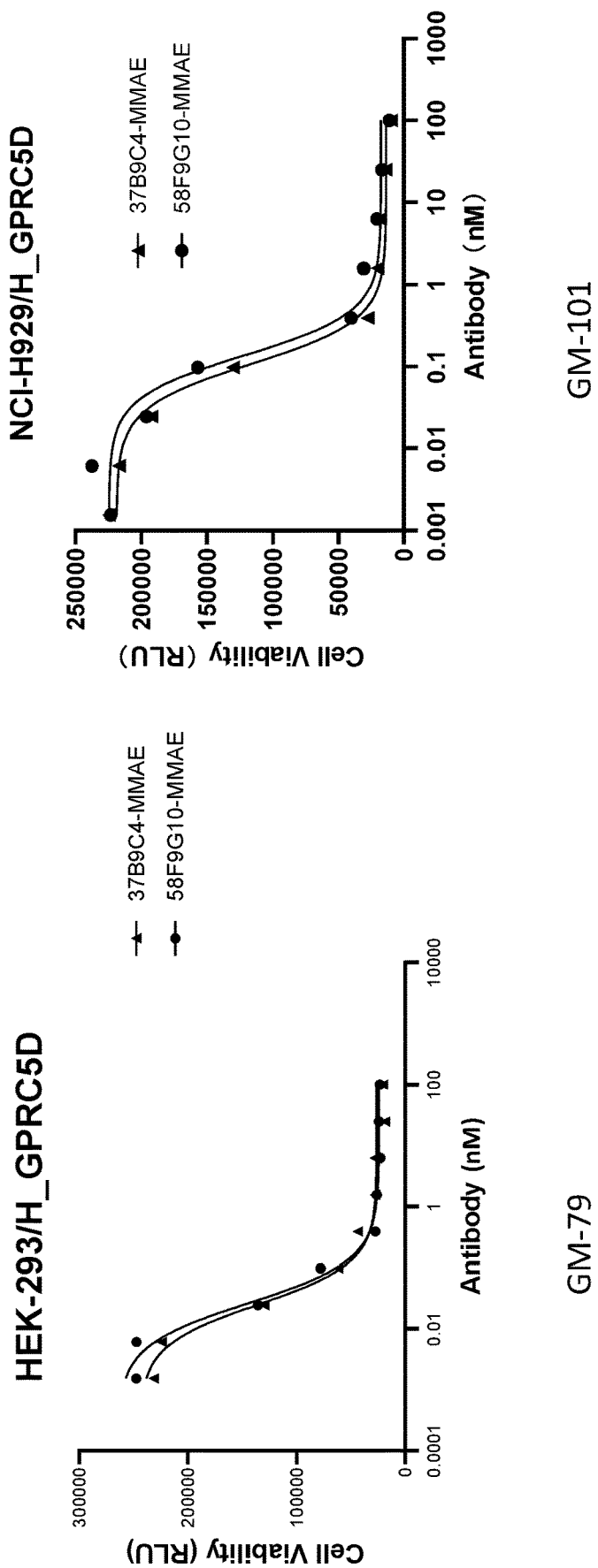
FIG. 13 shows the cell killing activities of the tested antibody-drug conjugates.
Figure 13:
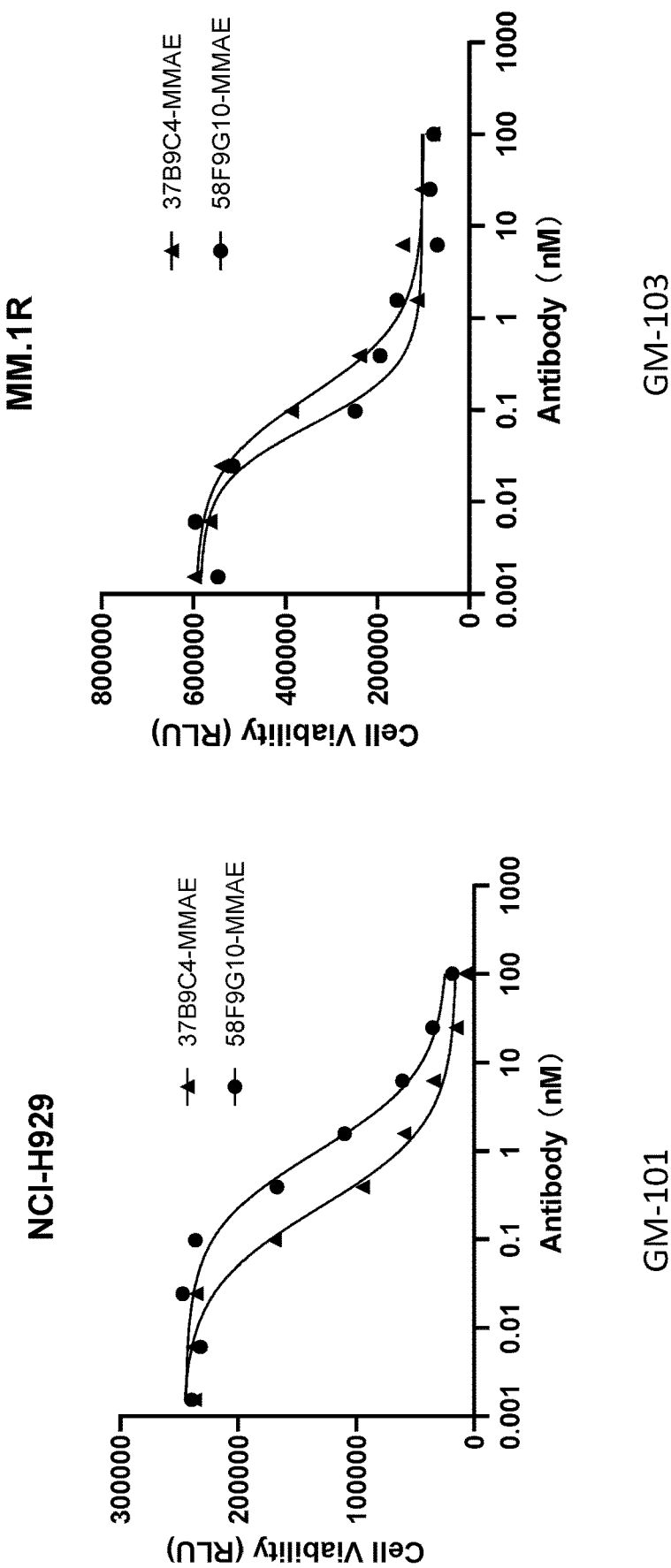

The human GPRC5D expressing HEK293 and NCI-H929 engineering cells (HEK293/H_GPRC5D and NCI-H929/H_GPRC5D), GPRC5D endogenously expressing NCI-H929 and MM.1R cells were seeded to a 96-well plate at 3000~4000 cells per well. The cells were treated with 37B9C4-MMAE and 58F9G10-MMAE at respective concentrations for 5 days. The cell viability was measured by CellTiteseeded to a 96-well plate at 3000~4000 cells per well with r-Glo reagent. The luciferase activity was detected by Envison. The results, in FIG. 13 and Table 12, show that these humanized antibodies have very strong killing activities.

TABLE 12

ADC Killing Activities

|  | Hek-293/H_GPRC5D (IC50, nM) | MM.1R (IC50, nM) | NCI-H929 (IC50, nM) | NCI-H929/GPRC5D (IC50, nM) |
|---|---|---|---|---|
| 37B9C4-MMAE | 0.025 | 0.14 | 0.23 | 0.11 |
| 58F9G10-MMAE | 0.026 | 0.07 | 0.99 | 0.14 |

Example 11. In vivo Anti-Tumor Activities

This example used a CDX animal model to test the anti-tumor activities of antibody 37B9C4 (H1L1).

In this study, 6-8 weeks female NCG mice (Jiangsu Jicui Yaokang Biotechnology Co., Ltd) were used. Each mouse was inoculated subcutaneously at the right axillary (lateral) with MM.1R tumor cell (2×106) in 0.1 ml of PBS with matrigel (V:V=1:1) for tumor development. The animals were randomly grouped when tumor volume reach around 60 mm3, then treatment started for the efficacy study. 37B9C4 at dose of 1 mg/kg, 3 mg/kg and 10 mg/kg were administrated via intravenous (i.v.) at day 0, day 7, day 14. The experiment was terminated at day 19 when the average tumor volume in vehicle group was over 2000 mm$^3$. The average tumor volume of PBS group, 37B9C4 (1 mg/kg) group, 37B9C4 (3 mg/kg) group and 37B9C4 (10 mg/kg) group were 2498.58 mm3, 1196.15 mm$^3$, 0.00 mm$^3$ (6/6 CR), and 0.00 mm$^3$ (6/6 CR) respectively. The tumor size were measured three times weekly in two dimensions using a caliper and the volume was expressed in mm$^3$ using the formula: V=0.5 a×b$^2$ where a and b were the long and short diameters of the tumor, respectively. Data points represent group (n=6) mean, error bars represent standard error of the mean (SEM).

Figure 14:
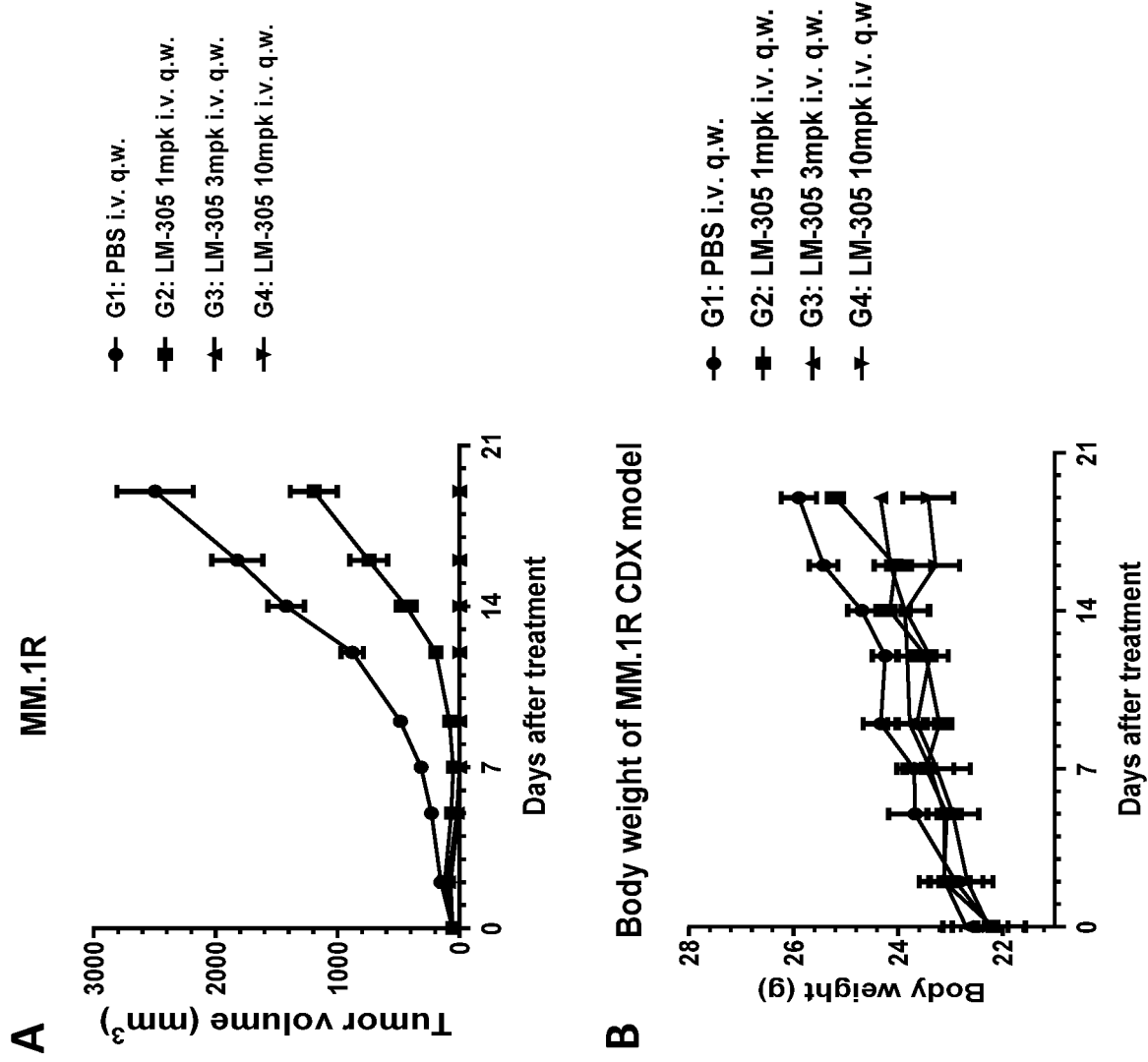
FIG. 14 shows the tumor inhibition activities of the tested antibody.

The body weight of MM.1R tumor bearing mice was monitored regularly as an indirect measure of toxicity. FIG. 14A shows the tumor growth curve of MM.1R tumor-bearing mice post administration of 37B9C4. The antibody dose-dependently inhibited the tumor growth in this tumor model, and achieved complete tumor inhibition at or above 3 mg/kg.

The detailed changes of body weight and relative change of body weight of MM.1R tumor bearing mice after administration are shown in FIG. 14B. During the administration period, all groups of mice had no significant body weight loss, and the mice in the administration group had good tolerance, demonstrating the safety of the treatment.

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

What is claimed is:

1. An antibody or antigen-binding fragment thereof having binding specificity to a human G-protein-coupled receptor family C group 5 member D (GPRC5D) protein, wherein the antibody or fragment thereof comprises a heavy chain variable region (VH) comprising heavy chain complementarity determining regions CDRH1, CDRH2, and CDRH3 and a light chain variable region (VL) comprising complementarity determining regions CDRL1, CDRL2, and CDRL3, and wherein the CDRH1, CDRH2, CDRH3, CDRL1, CDRL2, and CDRL3, respectively, comprise:
   a) the amino acid sequences of SEQ ID NO:42-47;
   b) the amino acid sequences of SEQ ID NO:29-34;
   c) the amino acid sequences of SEQ ID NO:54-59; or
   d) the amino acid sequences of SEQ ID NO:68-73.

2. The antibody or antigen-binding fragment thereof of claim 1, wherein the CDRH1, CDRH2, CDRH3, CDRL1, CDRL2, and CDRL3, respectively, comprise the amino acid sequences of SEQ ID NO:42-47.

3. The antibody or antigen-binding fragment thereof of claim 2, wherein the VH comprises an amino acid sequence selected from the group consisting of SEQ ID NO:9 and 48-50, and the VL comprises an amino acid sequence selected from the group consisting of SEQ ID NO:10 and 51-53.

4. The antibody or antigen-binding fragment thereof of claim 2, wherein the VH comprises the amino acid sequence of SEQ ID NO:48, and the VL comprises the amino acid sequence of SEQ ID NO:51.

5. The antibody or antigen-binding fragment thereof of claim 1, wherein the CDRH1, CDRH2, CDRH3, CDRL1, CDRL2, and CDRL3, respectively, comprise the amino acid sequences of SEQ ID NO:29-34.

6. The antibody or antigen-binding fragment thereof of claim 5, wherein the VH comprises an amino acid sequence selected from the group consisting of SEQ ID NO:7 and 35-37, and the VL comprises an amino acid sequence selected from the group consisting of SEQ ID NO:8 and 38-41.

7. The antibody or antigen-binding fragment thereof of claim 5, wherein the VH comprises the amino acid sequence of SEQ ID NO:35, and the VL comprises the amino acid sequence of SEQ ID NO:38.

8. The antibody or antigen-binding fragment thereof of claim 1, wherein the CDRH1, CDRH2, CDRH3, CDRL1, CDRL2, and CDRL3, respectively, comprise the amino acid sequences of SEQ ID NO:54-59.

9. The antibody or antigen-binding fragment thereof of claim 8, wherein the VH comprises an amino acid sequence selected from the group consisting of SEQ ID NO:61-64, and the VL comprises an amino acid sequence selected from the group consisting of SEQ ID NO:16 and 65-67.

10. The antibody or antigen-binding fragment thereof of claim 8, wherein the VH comprises the amino acid sequence of SEQ ID NO:61, and the VL comprises the amino acid sequence of SEQ ID NO:65.

11. The antibody or antigen-binding fragment thereof of claim 8, wherein the VH comprises the amino acid sequence of SEQ ID NO:63, and the VL comprises the amino acid sequence of SEQ ID NO:65.

12. The antibody or antigen-binding fragment thereof of claim 1, wherein the CDRH1, CDRH2, CDRH3, CDRL1, CDRL2, and CDRL3, respectively, comprise the amino acid sequences of SEQ ID NO:68-73.

13. The antibody or antigen-binding fragment thereof of claim 12, wherein the VH comprises an amino acid sequence selected from the group consisting of SEQ ID NO:1 and 74-79, and the VL comprises an amino acid sequence selected from the group consisting of SEQ ID NO:2 and 80-86.

14. The antibody or antigen-binding fragment thereof of claim 12, wherein the VH comprises the amino acid sequence of SEQ ID NO:76, and the VL comprises the amino acid sequence of SEQ ID NO:82.

15. The antibody or antigen-binding fragment thereof of claim 12, wherein the VH comprises the amino acid sequence of SEQ ID NO:77, and the VL comprises the amino acid sequence of SEQ ID NO:82.

16. The antibody or antigen-binding fragment thereof of claim 1, which is ADCC-competent.

17. The antibody or antigen-binding fragment thereof of claim 1, further comprising a cytotoxic drug conjugated to the antibody or antigen-binding fragment thereof.

18. A bispecific antibody, comprising the antigen-binding fragment of claim 1, and a second antigen-binding fragment having specificity to a second target protein.

19. The bispecific antibody of claim 18, wherein the second target protein is selected from the group consisting of CD3, CD16, CD19, CD28, CD64 and 4-1BB.

20. One or more polynucleotide(s) encoding the antibody or antigen-binding fragment thereof of claim 1.

21. A method of treating cancer in a patient in need thereof, comprising administering to the patient the antibody or fragment thereof of claim 1.

22. The method of claim 21, wherein the cancer is a hematological cancer.

23. The method of claim 22, wherein the hematological cancer is a GPRC5D-expressing B cell cancer.

24. The method of claim 23, wherein the GPRC5D-expressing B cell cancer is multiple myeloma.

* * * * *

SEQUENCE LISTING

```
<160> NUMBER OF SEQ ID NOS: 86

<210> SEQ ID NO 1
<211> LENGTH: 118
<212> TYPE: PRT
<213> ORGANISM: Artificial Sequence
<220> FEATURE:
<223> OTHER INFORMATION: Synthetic

<400> SEQUENCE: 1

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Thr Tyr
                20                  25                  30

Thr Met His Trp Val Lys Gln Arg Pro Gly Gln Gly Leu Glu Trp Leu
            35                  40                  45

Gly Tyr Ile Asn Pro Ser Ser Gly Tyr Thr Asn Tyr Asn Gln Lys Phe
    50                  55                  60

Lys Asp Lys Ala Thr Leu Thr Ala Gly Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ser Leu Arg Ser Arg Gly Tyr Phe Asp Tyr Trp Gly Gln Gly Thr
            100                 105                 110

Thr Leu Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: Synthetic
```

<400> SEQUENCE: 2

Asp Ile Val Met Thr Gln Ser Gln Thr Phe Met Ser Thr Ser Val Gly
1               5                   10                  15

Asp Arg Val Arg Ile Thr Cys Lys Ala Ser Gln Asn Val Gly Thr Ala
            20                  25                  30

Val Val Trp Tyr Gln Gln Lys Thr Gly Gln Ser Pro Arg Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Phe Phe Cys Gln Gln Tyr Ser Ser Tyr Pro Tyr
                85                  90                  95

Thr Phe Gly Gly Gly Thr Lys Leu Glu Ile Lys
            100                 105

<210> SEQ ID NO 3
<211> LENGTH: 113
<212> TYPE: PRT
<213> ORGANISM: Artificial Sequence
<220> FEATURE:
<223> OTHER INFORMATION: Synthetic

<400> SEQUENCE: 3

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Ile Asn Tyr
            20                  25                  30

Leu Ile Glu Trp Ile Lys Gln Arg Pro Gly Gln Gly Leu Glu Trp Ile
        35                  40                  45

Gly Met Ile Asn Pro Gly Ser Gly Gly Thr Asn Tyr Asn Glu Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Asp Asp Ser Ala Val Tyr Phe Cys
                85                  90                  95

Ala Arg Asn Trp Asp Val Trp Gly Gln Gly Thr Thr Leu Thr Val Ser
            100                 105                 110

Ser

<210> SEQ ID NO 4
<211> LENGTH: 112
<212> TYPE: PRT
<213> ORGANISM: Artificial Sequence
<220> FEATURE:
<223> OTHER INFORMATION: Synthetic

<400> SEQUENCE: 4

Asp Val Val Met Thr Gln Ser Pro Leu Ser Leu Pro Val Ser Leu Gly
1               5                   10                  15

Asp Gln Ala Ser Val Ser Cys Arg Ser Ser Gln Ser Leu Val His Ser
            20                  25                  30

Thr Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 5
<211> LENGTH: 118
<212> TYPE: PRT
<213> ORGANISM: Artificial Sequence
<220> FEATURE:
<223> OTHER INFORMATION: Synthetic

<400> SEQUENCE: 5

Glu Val Gln Leu Gln Gln Ser Gly Pro Glu Leu Val Lys Pro Gly Ala
1               5                   10                  15

Ser Met Lys Leu Ser Cys Lys Ala Ser Gly Tyr Ser Phe Thr Gly Tyr
                20                  25                  30

Thr Met His Trp Val Lys Gln Ser His Gly Glu Asn Leu Glu Trp Ile
            35                  40                  45

Gly Leu Ile Asn Pro Tyr Asn Gly Gly Thr Asn Tyr Asn Gln Lys Phe
50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ser Arg Trp Gly Leu Arg Arg Ala Met Asp Tyr Trp Gly Gln Gly Thr
            100                 105                 110

Ser Val Thr Val Ser Ser
            115

<210> SEQ ID NO 6
<211> LENGTH: 107
<212> TYPE: PRT
<213> ORGANISM: Artificial Sequence
<220> FEATURE:
<223> OTHER INFORMATION: Synthetic

<400> SEQUENCE: 6

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Ser Asn
                20                  25                  30

Val Ala Trp Tyr Gln Gln Lys Pro Gly Gln Ser Pro Lys Ala Leu Ile
            35                  40                  45

Tyr Ser Ala Ser Tyr Arg Tyr Ser Gly Val Pro Asp Arg Phe Thr Gly
50                  55                  60

Asn Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Tyr Asn Ser Pro Trp
                85                  90                  95

Thr Phe Gly Gly Gly Thr Lys Leu Glu Ile Lys
            100                 105

<210> SEQ ID NO 7
<211> LENGTH: 117
<212> TYPE: PRT
<213> ORGANISM: Artificial Sequence -continued
<220> FEATURE:
<223> OTHER INFORMATION: Synthetic

<400> SEQUENCE: 7

Glu Val His Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Asn
65                  70                  75                  80

Leu Gln Met Ser Ser Leu Lys Ser Glu Asp Thr Ala Met Tyr Tyr Cys
                85                  90                  95

Ala Arg Gln Gly Gly Asp Ala Met Asp Tyr Trp Gly Gln Gly Thr Ser
            100                 105                 110

Val Thr Val Ser Ser
        115

<210> SEQ ID NO 8
<211> LENGTH: 106
<212> TYPE: PRT
<213> ORGANISM: Artificial Sequence
<220> FEATURE:
<223> OTHER INFORMATION: Synthetic

<400> SEQUENCE: 8

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Asn Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Arg Leu Thr
                85                  90                  95

Phe Gly Ala Gly Thr Lys Leu Glu Leu Lys
            100                 105

<210> SEQ ID NO 9
<211> LENGTH: 124
<212> TYPE: PRT
<213> ORGANISM: Artificial Sequence
<220> FEATURE:
<223> OTHER INFORMATION: Synthetic

<400> SEQUENCE: 9

Glu Val Asn Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

```
Ala Glu Ile Arg Leu Lys Ser Asn Asn Tyr Ala Thr His Tyr Ala Glu
 50                  55                  60

Ser Val Lys Gly Arg Phe Thr Ile Ser Arg Asp Asp Ser Lys Ser Ser
 65                  70                  75                  80

Val Tyr Leu Gln Met Asn Asn Leu Arg Ala Glu Asp Thr Gly Ile Tyr
                 85                  90                  95

Tyr Cys Thr Arg Pro Leu Leu Trp Phe Arg Arg Tyr Tyr Ala Met Asp
                100                 105                 110

Tyr Trp Gly Gln Gly Thr Ser Val Thr Val Ser Ser
            115                 120
```

<210> SEQ ID NO 10
<211> LENGTH: 107
<212> TYPE: PRT
<213> ORGANISM: Artificial Sequence
<220> FEATURE:
<223> OTHER INFORMATION: Synthetic

<400> SEQUENCE: 10

```
Asp Ile Gln Met Thr Gln Thr Thr Ser Ser Leu Ser Ala Ser Leu Gly
 1               5                  10                  15

Asp Arg Ile Thr Ile Ser Cys Ser Ala Ser Gln Gly Ile Ser Asn Tyr
                 20                  25                  30

Leu Asn Trp Tyr Gln Gln Lys Pro Asp Gly Thr Val Lys Leu Leu Ile
             35                  40                  45

Tyr Tyr Thr Ser Ser Leu His Ser Gly Val Pro Ser Arg Phe Ser Gly
 50                  55                  60

Ser Gly Ser Gly Thr Asp Tyr Ser Leu Thr Ile Ser Asn Leu Glu Pro
 65                  70                  75                  80

Ala Asp Ile Ala Thr Tyr Tyr Cys Gln Gln Tyr Ser Lys Leu Pro Phe
                 85                  90                  95

Thr Phe Gly Ser Gly Thr Lys Leu Glu Ile Lys
                100                 105
```

<210> SEQ ID NO 11
<211> LENGTH: 118
<212> TYPE: PRT
<213> ORGANISM: Artificial Sequence
<220> FEATURE:
<223> OTHER INFORMATION: Synthetic

<400> SEQUENCE: 11

```
Gln Val Gln Leu Gln Gln Ser Gly Ala Glu Leu Ala Arg Pro Gly Ala
 1               5                  10                  15

Ser Val Lys Met Ser Cys Lys Ala Ser Gly Tyr Thr Phe Thr Thr Tyr
                 20                  25                  30

Thr Met His Trp Val Lys Gln Arg Pro Gly Gln Gly Leu Glu Trp Ile
             35                  40                  45

Gly Tyr Ile Asn Pro Ser Ser Gly Tyr Thr Asn Tyr Asn Gln Lys Phe
             50                  55                  60

Lys Asp Lys Ala Thr Leu Thr Ala Gly Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Ser Leu Arg Ser Arg Gly Tyr Phe Asp Tyr Trp Gly Arg Gly Thr
                100                 105                 110

Thr Leu Thr Val Ser Ser
            115
```

<210> SEQ ID NO 12
<211> LENGTH: 107
<212> TYPE: PRT
<213> ORGANISM: Artificial Sequence
<220> FEATURE:
<223> OTHER INFORMATION: Synthetic

<400> SEQUENCE: 12

```
Asp Ile Val Met Thr Gln Ser Gln Lys Phe Leu Ser Thr Ser Val Gly
1               5                   10                  15

Asp Arg Val Ser Ile Thr Cys Lys Ala Ser Gln Asn Val Gly Thr Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
50                  55                  60

Ser Gly Ser Gly Thr Asp Phe Thr Leu Thr Ile Ser Asn Met Gln Ser
65                  70                  75                  80

Glu Asp Leu Ala Gly Tyr Phe Cys Gln Gln Tyr Ser Ser Tyr Pro Tyr
                85                  90                  95

Thr Phe Gly Gly Gly Thr Lys Leu Glu Ile Lys
            100                 105
```

<210> SEQ ID NO 13
<211> LENGTH: 122
<212> TYPE: PRT
<213> ORGANISM: Artificial Sequence
<220> FEATURE:
<223> OTHER INFORMATION: Synthetic

<400> SEQUENCE: 13

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Arg Asn
            20                  25                  30

Ile Met His Trp Val Lys Gln Lys Pro Gly Gln Gly Leu Glu Trp Ile
        35                  40                  45

Gly Tyr Ile Asn Pro Tyr Asn Ala Gly Ser Lys Tyr Asn Glu Lys Phe
50                  55                  60

Lys Gly Lys Ala Thr Leu Thr Ser Asp Ile Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Glu Glu Val Tyr Tyr Arg Tyr Gly Ala Trp Phe Ala Tyr Trp
            100                 105                 110

Gly His Gly Thr Leu Val Thr Val Ser Ala
        115                 120
```

<210> SEQ ID NO 14
<211> LENGTH: 111
<212> TYPE: PRT
<213> ORGANISM: Artificial Sequence
<220> FEATURE:
<223> OTHER INFORMATION: Synthetic

<400> SEQUENCE: 14

```
Asp Ile Val Leu Thr Gln Ser Pro Ala Ser Leu Ala Val Ser Leu Gly
1               5                   10                  15
```

Gln Arg Ala Thr Ile Ser Cys Arg Ala Ser Gln Ser Val Ser Thr Ser
                20                  25                  30

Ser Tyr Ser Tyr Met His Trp Tyr Gln Gln Lys Pro Gly Gln Pro Pro
            35                  40                  45

Lys Leu Leu Ile Lys Tyr Ala Ser Asn Leu Glu Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Thr Ala Thr Tyr Tyr Cys Gln His Ser Trp
                85                  90                  95

Glu Ile Pro Arg Thr Phe Gly Gly Gly Thr Lys Leu Glu Ile Lys
            100                 105                 110

<210> SEQ ID NO 15
<211> LENGTH: 119
<212> TYPE: PRT
<213> ORGANISM: Artificial Sequence
<220> FEATURE:
<223> OTHER INFORMATION: Synthetic

<400> SEQUENCE: 15

Glu Val Gln Leu Gln Gln Ser Gly Pro Glu Leu Val Lys Thr Gly Ala
 1               5                  10                  15

Ser Val Lys Ile Ser Cys Lys Ala Ser Gly Tyr Ser Phe Thr Gly Tyr
                20                  25                  30

Tyr Ile His Trp Val Lys Gln Ser His Gly Lys Ser Leu Glu Trp Ile
            35                  40                  45

Gly Tyr Ile Ser Cys Tyr Asn Gly Ala Thr Ser Phe Asn Gln Lys Phe
 50                  55                  60

Lys Gly Lys Ala Thr Phe Thr Val Asp Thr Ser Ser Ser Thr Ala Tyr
 65                  70                  75                  80

Met Gln Phe Asn Ser Leu Thr Ser Glu Asp Ser Ala Val Tyr Tyr Cys
                85                  90                  95

Ala Arg Thr Glu Leu Arg Gly Pro Trp Phe Ala Tyr Trp Gly Gln Gly
            100                 105                 110

Thr Leu Val Thr Val Ser Ala
        115

<210> SEQ ID NO 16
<211> LENGTH: 106
<212> TYPE: PRT
<213> ORGANISM: Artificial Sequence
<220> FEATURE:
<223> OTHER INFORMATION: Synthetic

<400> SEQUENCE: 16

Gln Thr Val Leu Thr Gln Ser Pro Ala Ile Met Ser Ala Ser Pro Gly
 1               5                  10                  15

Glu Lys Val Thr Met Thr Cys Ser Ala Ser Ser Val Ser Tyr Met
                20                  25                  30

Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Gly Ser
 50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Asn Asn Pro Leu Thr
                85                  90                  95

```
Phe Gly Ala Gly Thr Lys Leu Glu Leu Lys
            100                 105
```

<210> SEQ ID NO 17
<211> LENGTH: 113
<212> TYPE: PRT
<213> ORGANISM: Artificial Sequence
<220> FEATURE:
<223> OTHER INFORMATION: Synthetic

<400> SEQUENCE: 17

```
Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Ile Asn Tyr
                20                  25                  30

Leu Ile Glu Trp Ile Lys Gln Arg Pro Gly Gln Gly Leu Glu Trp Ile
            35                  40                  45

Gly Met Ile Asn Pro Gly Ser Gly Gly Thr Asn Tyr Asn Glu Lys Phe
        50                  55                  60

Lys Asp Lys Ala Thr Leu Thr Ala Asp Lys Ser Ser Thr Ala Tyr
65                  70                  75                  80

Met Gln Leu Ser Ser Leu Thr Ser Asp Asp Ser Ala Val Tyr Phe Cys
                85                  90                  95

Ala Arg Asn Trp Asp Val Trp Gly Gln Gly Thr Thr Leu Thr Val Ser
            100                 105                 110

Ser
```

<210> SEQ ID NO 18
<211> LENGTH: 112
<212> TYPE: PRT
<213> ORGANISM: Artificial Sequence
<220> FEATURE:
<223> OTHER INFORMATION: Synthetic

<400> SEQUENCE: 18

```
Asp Val Val Met Thr Gln Ser Pro Leu Ser Leu Pro Val Ser Leu Gly
1               5                   10                  15

Asp Gln Ala Ser Val Ser Cys Arg Ser Ser Gln Ser Leu Val His Ser
                20                  25                  30

Thr Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110
```

<210> SEQ ID NO 19
<211> LENGTH: 122
<212> TYPE: PRT
<213> ORGANISM: Artificial Sequence
<220> FEATURE:
<223> OTHER INFORMATION: Synthetic

<400> SEQUENCE: 19

```
Gln Val His Leu Gln Gln Ser Gly Ala Glu Leu Ala Arg Pro Gly Ala
```

```
                1               5                   10                  15
            Ser Val Lys Met Ser Cys Lys Ala Ser Gly Tyr Thr Phe Thr Thr Tyr
                            20                  25                  30

Thr Met His Trp Val Lys Gln Arg Pro Gly Gln Gly Leu Glu Trp Ile
                            35                  40                  45

Gly Tyr Ile Asn Pro Asn Ser Ala Tyr Thr Asn Tyr Asn Gln Lys Phe
                            50                  55                  60

Lys Asp Lys Ala Thr Leu Thr Ala Asp Lys Ser Ser Thr Ala Tyr
            65                  70                  75                  80

Met Gln Leu Ser Ser Leu Thr Ser Glu Asp Ser Ala Val Tyr Tyr Cys
                            85                  90                  95

Ala Arg Arg Val Leu Leu Leu Arg Val Leu Asp Phe Phe Asp Tyr Trp
                            100                 105                 110

Gly Gln Gly Thr Thr Leu Thr Val Ser Ser
                            115                 120
```

<210> SEQ ID NO 20
<211> LENGTH: 107
<212> TYPE: PRT
<213> ORGANISM: Artificial Sequence
<220> FEATURE:
<223> OTHER INFORMATION: Synthetic

<400> SEQUENCE: 20

```
            Asp Val Gln Ile Thr Gln Ser Pro Ser Tyr Leu Ala Ala Ser Pro Gly
            1               5                   10                  15

Glu Thr Ile Thr Ile Asn Cys Arg Ala Ser Lys Ser Ile Asn Lys Tyr
                            20                  25                  30

Leu Thr Trp Tyr Gln Glu Lys Pro Gly Lys Thr Asn Lys Leu Leu Ile
                            35                  40                  45

Tyr Ser Gly Ser Thr Leu Gln Ser Gly Ile Pro Ser Arg Phe Ser Gly
                            50                  55                  60

Ser Gly Ser Gly Ser Asp Phe Thr Leu Thr Ile Ser Ser Leu Glu Pro
            65                  70                  75                  80

Glu Asp Phe Ala Met Tyr Tyr Cys Gln Gln His Asn Glu Tyr Pro Leu
                            85                  90                  95

Thr Phe Gly Thr Gly Thr Lys Leu Glu Leu Lys
                            100                 105
```

<210> SEQ ID NO 21
<211> LENGTH: 118
<212> TYPE: PRT
<213> ORGANISM: Artificial Sequence
<220> FEATURE:
<223> OTHER INFORMATION: Synthetic

<400> SEQUENCE: 21

```
            Glu Val Gln Leu Gln Gln Ser Gly Pro Glu Leu Val Lys Pro Gly Ala
            1               5                   10                  15

Ser Met Lys Ile Ser Cys Lys Ala Ser Gly Tyr Ser Phe Thr Gly Tyr
                            20                  25                  30

Thr Met Asn Trp Val Lys Gln Ser His Gly Lys Asn Leu Glu Trp Ile
                            35                  40                  45

Gly Leu Ile Asn Pro Tyr Asn Gly Gly Ile Arg Tyr Asn Gln Lys Phe
                            50                  55                  60

Lys Gly Lys Ala Thr Leu Thr Val Asp Lys Ser Ser Thr Ala Tyr
            65                  70                  75                  80
```

Met Glu Leu Leu Ser Leu Thr Ser Glu Asp Ser Ala Val Tyr Tyr Cys
            85                  90                  95

Ala Arg Trp Gly Leu Arg Arg Ala Met Asp Tyr Trp Gly Gln Gly Thr
            100                 105                 110

Ser Val Thr Val Ser Ser
            115

<210> SEQ ID NO 22
<211> LENGTH: 107
<212> TYPE: PRT
<213> ORGANISM: Artificial Sequence
<220> FEATURE:
<223> OTHER INFORMATION: Synthetic

<400> SEQUENCE: 22

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
            35                  40                  45

Tyr Ser Ala Ser Tyr Arg Tyr Ser Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Ser Pro Trp
                85                  90                  95

Thr Phe Gly Gly Gly Thr Lys Leu Glu Ile Lys
            100                 105

<210> SEQ ID NO 23
<211> LENGTH: 118
<212> TYPE: PRT
<213> ORGANISM: Artificial Sequence
<220> FEATURE:
<223> OTHER INFORMATION: Synthetic

<400> SEQUENCE: 23

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
            35                  40                  45

Gly Leu Ile Asn Pro Tyr Asn Gly Gly Thr Asn Tyr Asn Gln Lys Phe
        50                  55                  60

Lys Gly Lys Ala Thr Leu Ala Val Asp Lys Ser Ser Thr Ala Tyr
65                  70                  75                  80

Met Asp Leu Leu Ser Leu Thr Ser Glu Asp Ser Ala Val Tyr Tyr Cys
                85                  90                  95

Ser Arg Trp Gly Leu Arg Arg Ala Met Asp Tyr Trp Gly Gln Gly Thr
            100                 105                 110

Ser Val Thr Val Ser Ser
            115

<210> SEQ ID NO 24
<211> LENGTH: 107
<212> TYPE: PRT
<213> ORGANISM: Artificial Sequence
<220> FEATURE:
<223> OTHER INFORMATION: Synthetic

<400> SEQUENCE: 24

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Ser Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Asn Ser Pro Trp
                85                  90                  95

Thr Phe Gly Gly Gly Thr Lys Leu Glu Ile Lys
            100                 105

<210> SEQ ID NO 25
<211> LENGTH: 118
<212> TYPE: PRT
<213> ORGANISM: Artificial Sequence
<220> FEATURE:
<223> OTHER INFORMATION: Synthetic

<400> SEQUENCE: 25

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met His Trp Val Lys Gln Ser His Gly Glu Asn Leu Glu Trp Ile
        35                  40                  45

Gly Leu Ile Asn Pro Tyr Asn Gly Gly Thr Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ser Arg Trp Gly Leu Arg Arg Ala Met Asp Tyr Trp Gly Gln Gly Thr
            100                 105                 110

Ser Val Thr Val Ser Ser
        115

<210> SEQ ID NO 26
<211> LENGTH: 107
<212> TYPE: PRT
<213> ORGANISM: Artificial Sequence
<220> FEATURE:
<223> OTHER INFORMATION: Synthetic

<400> SEQUENCE: 26

Asp Ile Val Met Thr Gln Ser Gln Lys Phe Met Ser Thr Ser Ile Gly
1               5                   10                  15

Asp Arg Val Ser Val Thr Cys Lys Ala Ser Gln Asn Val Gly Ser Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
                50                  55                  60

Asn Gly Ser Gly Thr Asp Phe Thr Leu Thr Ile Ser Asn Val Gln Ser
 65                  70                  75                  80

Glu Asp Leu Ala Glu Tyr Phe Cys Gln Gln Tyr Tyr Asn Ser Pro Trp
                 85                  90                  95

Thr Phe Gly Gly Gly Thr Lys Leu Glu Ile Lys
            100                 105

<210> SEQ ID NO 27
<211> LENGTH: 113
<212> TYPE: PRT
<213> ORGANISM: Artificial Sequence
<220> FEATURE:
<223> OTHER INFORMATION: Synthetic

<400> SEQUENCE: 27

Gln Val Gln Leu Gln Gln Ser Gly Ala Glu Leu Val Arg Pro Gly Thr
 1               5                  10                  15

Ser Val Lys Val Ser Cys Lys Ala Ser Gly Tyr Ala Phe Ile Ser Tyr
                20                  25                  30

Leu Ile Glu Trp Ile Lys Gln Arg Pro Gly Gln Gly Leu Glu Trp Ile
             35                  40                  45

Gly Met Ile Asn Pro Gly Ser Gly Gly Thr Asn Tyr Asn Glu Lys Phe
 50                  55                  60

Lys Asp Lys Ala Thr Leu Thr Ala Asp Lys Ser Ser Ser Thr Ala Tyr
 65                  70                  75                  80

Met Gln Leu Ser Ser Leu Thr Ser Asp Asp Ser Ala Val Tyr Phe Cys
                 85                  90                  95

Ala Arg Asn Trp Asp Val Trp Gly Gln Gly Thr Thr Leu Thr Val Ser
            100                 105                 110

Ser

<210> SEQ ID NO 28
<211> LENGTH: 112
<212> TYPE: PRT
<213> ORGANISM: Artificial Sequence
<220> FEATURE:
<223> OTHER INFORMATION: Synthetic

<400> SEQUENCE: 28

Asp Val Val Met Thr Gln Ser Pro Leu Ser Leu Pro Val Ser Leu Gly
 1               5                  10                  15

Asp Gln Ala Ser Val Ser Cys Arg Ser Ser Gln Ser Leu Val His Ser
                20                  25                  30

Thr Gly Asn Thr Tyr Leu His Trp Tyr Leu Gln Lys Pro Gly Gln Ser
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Trp Thr Phe Gly Gly Gly Thr Lys Leu Glu Ile Lys
            100                 105                 110

<210> SEQ ID NO 29
<211> LENGTH: 5

```
<212> TYPE: PRT
<213> ORGANISM: Artificial Sequence
<220> FEATURE:
<223> OTHER INFORMATION: Synthetic

<400> SEQUENCE: 29

Ser Tyr Gly Met Ser
1               5

<210> SEQ ID NO 30
<211> LENGTH: 17
<212> TYPE: PRT
<213> ORGANISM: Artificial Sequence
<220> FEATURE:
<223> OTHER INFORMATION: Synthetic

<400> SEQUENCE: 30

Thr Ile Ser Ser Gly Gly Ser Tyr Thr Tyr Tyr Pro Asp Ser Val Lys
1               5                   10                  15

Gly

<210> SEQ ID NO 31
<211> LENGTH: 8
<212> TYPE: PRT
<213> ORGANISM: Artificial Sequence
<220> FEATURE:
<223> OTHER INFORMATION: Synthetic

<400> SEQUENCE: 31

Gln Gly Gly Asp Ala Met Asp Tyr
1               5

<210> SEQ ID NO 32
<211> LENGTH: 11
<212> TYPE: PRT
<213> ORGANISM: Artificial Sequence
<220> FEATURE:
<223> OTHER INFORMATION: Synthetic

<400> SEQUENCE: 32

Arg Ala Ser Gln Ser Ile Asn Asn Asn Leu His
1               5                   10

<210> SEQ ID NO 33
<211> LENGTH: 7
<212> TYPE: PRT
<213> ORGANISM: Artificial Sequence
<220> FEATURE:
<223> OTHER INFORMATION: Synthetic

<400> SEQUENCE: 33

Tyr Ala Ser Gln Ser Ile Ser
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic

<400> SEQUENCE: 34

Gln Gln Ser Asn Ser Arg Leu Thr
1               5

<210> SEQ ID NO 35
```

```
<211> LENGTH: 117
<212> TYPE: PRT
<213> ORGANISM: Artificial Sequence
<220> FEATURE:
<223> OTHER INFORMATION: Synthetic

<400> SEQUENCE: 35

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Gln Gly Gly Asp Ala Met Asp Tyr Trp Gly Gln Gly Thr Leu
            100                 105                 110

Val Thr Val Ser Ser
        115

<210> SEQ ID NO 36
<211> LENGTH: 117
<212> TYPE: PRT
<213> ORGANISM: Artificial Sequence
<220> FEATURE:
<223> OTHER INFORMATION: Synthetic

<400> SEQUENCE: 36

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Gly Met Ser Trp Val Arg Gln Thr Pro Gly Lys Gly Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Ser Leu Tyr
 65                  70                  75                  80

Leu Gln Met Ser Ser Leu Arg Ala Glu Asp Thr Ala Val Tyr Tyr Cys
                85                  90                  95

Ala Arg Gln Gly Gly Asp Ala Met Asp Tyr Trp Gly Gln Gly Thr Leu
            100                 105                 110

Val Thr Val Ser Ser
        115

<210> SEQ ID NO 37
<211> LENGTH: 117
<212> TYPE: PRT
<213> ORGANISM: Artificial Sequence
<220> FEATURE:
<223> OTHER INFORMATION: Synthetic

<400> SEQUENCE: 37

Glu Val His Leu Val Glu Ser Gly Gly Gly Leu Val Lys Pro Gly Gly
 1               5                  10                  15
```

Ser Leu Arg Leu Ser Cys Ala Ala Ser Gly Phe Thr Phe Ser Ser Tyr
            20                  25                  30

Gly Met Ser Trp Val Arg Gln Thr Pro Gly Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Ser Leu Asn
65                  70                  75                  80

Leu Gln Met Ser Ser Leu Arg Ala Glu Asp Thr Ala Val Tyr Tyr Cys
                85                  90                  95

Ala Arg Gln Gly Gly Asp Ala Met Asp Tyr Trp Gly Gln Gly Thr Leu
            100                 105                 110

Val Thr Val Ser Ser
            115

<210> SEQ ID NO 38
<211> LENGTH: 106
<212> TYPE: PRT
<213> ORGANISM: Artificial Sequence
<220> FEATURE:
<223> OTHER INFORMATION: Synthetic

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Asn Asn
            20                  25                  30

Leu His Trp Tyr Gln Gln Lys Pro Gly Lys Ala Pro Lys Leu Leu Ile
        35                  40                  45

Tyr Tyr Ala Ser Gln Ser Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Arg Leu Thr
                85                  90                  95

Phe Gly Gly Gly Thr Lys Val Glu Ile Lys
            100                 105

<210> SEQ ID NO 39
<211> LENGTH: 106
<212> TYPE: PRT
<213> ORGANISM: Artificial Sequence
<220> FEATURE:
<223> OTHER INFORMATION: Synthetic

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Asn Asn
            20                  25                  30

Leu His Trp Tyr Gln Gln Lys Pro Gly Lys Ala Pro Lys Leu Leu Ile
        35                  40                  45

Tyr Tyr Ala Ser Gln Ser Ile Ser Gly Ile Pro Ser Arg Phe Ser Gly
    50                  55                  60

Ser Gly Ser Gly Thr Asp Phe Thr Leu Thr Ile Ser Ser Val Gln Pro
65                  70                  75                  80

Glu Asp Phe Ala Thr Tyr Phe Cys Gln Gln Ser Asn Ser Arg Leu Thr
                85                  90                  95

```
Phe Gly Gly Gly Thr Lys Val Glu Ile Lys
            100                 105

<210> SEQ ID NO 40
<211> LENGTH: 106
<212> TYPE: PRT
<213> ORGANISM: Artificial Sequence
<220> FEATURE:
<223> OTHER INFORMATION: Synthetic

<400> SEQUENCE: 40

Asp Ile Gln Leu Thr Gln Ser Pro Ser Leu Ser Ala Ser Val Gly
1               5                   10                  15

Asp Arg Val Thr Ile Thr Cys Arg Ala Ser Gln Ser Ile Asn Asn Asn
            20                  25                  30

Leu His Trp Tyr Gln Gln Lys Pro Gly Lys Ser Pro Lys Leu Leu Ile
        35                  40                  45

Tyr Tyr Ala Ser Gln Ser Ile Ser Gly Ile Pro Ser Arg Phe Ser Gly
    50                  55                  60

Ser Gly Ser Gly Thr Asp Phe Thr Leu Thr Ile Ser Ser Val Gln Pro
65                  70                  75                  80

Glu Asp Phe Ala Thr Tyr Phe Cys Gln Gln Ser Asn Ser Arg Leu Thr
                85                  90                  95

Phe Gly Gly Gly Thr Lys Leu Glu Ile Lys
            100                 105

<210> SEQ ID NO 41
<211> LENGTH: 106
<212> TYPE: PRT
<213> ORGANISM: Artificial Sequence
<220> FEATURE:
<223> OTHER INFORMATION: Synthetic

<400> SEQUENCE: 41

Asp Ile Val Leu Thr Gln Ser Pro Ser Ser Leu Ser Val Ser Val Gly
1               5                   10                  15

Asp Arg Val Thr Leu Thr Cys Arg Ala Ser Gln Ser Ile Asn Asn Asn
            20                  25                  30

Leu His Trp Tyr Gln Gln Lys Pro Gly Lys Ser Pro Lys Leu Leu Ile
        35                  40                  45

Tyr Tyr Ala Ser Gln Ser Ile Ser Gly Ile Pro Ser Arg Phe Ser Gly
    50                  55                  60

Ser Gly Ser Gly Thr Asp Phe Thr Leu Thr Ile Ser Ser Val Gln Pro
65                  70                  75                  80

Glu Asp Phe Ala Thr Tyr Phe Cys Gln Gln Ser Asn Ser Arg Leu Thr
                85                  90                  95

Phe Gly Gly Gly Thr Lys Leu Glu Ile Lys
            100                 105

<210> SEQ ID NO 42
<211> LENGTH: 5
<212> TYPE: PRT
<213> ORGANISM: Artificial Sequence
<220> FEATURE:
<223> OTHER INFORMATION: Synthetic

<400> SEQUENCE: 42

Asp Tyr Trp Met Asn
1               5
```

<210> SEQ ID NO 43
<211> LENGTH: 19
<212> TYPE: PRT
<213> ORGANISM: Artificial Sequence
<220> FEATURE:
<223> OTHER INFORMATION: Synthetic

<400> SEQUENCE: 43

Glu Ile Arg Leu Lys Ser Asn Asn Tyr Ala Thr His Tyr Ala Glu Ser
1               5                   10                  15

Val Lys Gly

<210> SEQ ID NO 44
<211> LENGTH: 13
<212> TYPE: PRT
<213> ORGANISM: Artificial Sequence
<220> FEATURE:
<223> OTHER INFORMATION: Synthetic

<400> SEQUENCE: 44

Pro Leu Leu Trp Phe Arg Arg Tyr Tyr Ala Met Asp Tyr
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Synthetic

<400> SEQUENCE: 45

Ser Ala Ser Gln Gly Ile Ser Asn Tyr Leu Asn
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Synthetic

<400> SEQUENCE: 46

Tyr Thr Ser Ser Leu His Ser
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic

<400> SEQUENCE: 47

Gln Gln Tyr Ser Lys Leu Pro Phe Thr
1               5

<210> SEQ ID NO 48
<211> LENGTH: 124
<212> TYPE: PRT
<213> ORGANISM: Artificial Sequence
<220> FEATURE:
<223> OTHER INFORMATION: Synthetic

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asn Trp Val Arg Gln Ala Pro Gly Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Pro Leu Leu Trp Phe Arg Arg Tyr Tyr Ala Met Asp
            100                 105                 110

Tyr Trp Gly Gln Gly Thr Leu Val Thr Val Ser Ser
            115                 120

<210> SEQ ID NO 49
<211> LENGTH: 124
<212> TYPE: PRT
<213> ORGANISM: Artificial Sequence
<220> FEATURE:
<223> OTHER INFORMATION: Synthetic

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asn Trp Val Arg Gln Ser Pro Gly Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asn Ala Lys Ser Ser
65                  70                  75                  80

Leu Tyr Leu Gln Met Asn Ser Leu Arg Ala Glu Asp Thr Ala Val Tyr
                85                  90                  95

Tyr Cys Thr Arg Pro Leu Leu Trp Phe Arg Arg Tyr Tyr Ala Met Asp
            100                 105                 110

Tyr Trp Gly Gln Gly Thr Leu Val Thr Val Ser Ser
            115                 120

<210> SEQ ID NO 50
<211> LENGTH: 124
<212> TYPE: PRT
<213> ORGANISM: Artificial Sequence
<220> FEATURE:
<223> OTHER INFORMATION: Synthetic

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asn Trp Val Arg Gln Ser Pro Gly Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Ser Ser

```
              65                  70                  75                  80
Val Tyr Leu Gln Met Asn Ser Leu Arg Ala Glu Asp Thr Ala Val Tyr
                 85                  90                  95
Tyr Cys Thr Arg Pro Leu Leu Trp Phe Arg Arg Tyr Tyr Ala Met Asp
                100                 105                 110
Tyr Trp Gly Gln Gly Thr Leu Val Thr Val Ser Ser
            115                 120

<210> SEQ ID NO 51
<211> LENGTH: 107
<212> TYPE: PRT
<213> ORGANISM: Artificial Sequence
<220> FEATURE:
<223> OTHER INFORMATION: Synthetic

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Lys Leu Pro Phe
                85                  90                  95

Thr Phe Gly Gln Gly Thr Lys Leu Glu Ile Lys
            100                 105

<210> SEQ ID NO 52
<211> LENGTH: 107
<212> TYPE: PRT
<213> ORGANISM: Artificial Sequence
<220> FEATURE:
<223> OTHER INFORMATION: Synthetic

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Asn Tyr
            20                  25                  30

Leu Asn Trp Tyr Gln Gln Lys Pro Gly Lys Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Lys Leu Pro Phe
                85                  90                  95

Thr Phe Gly Gln Gly Thr Lys Leu Glu Ile Lys
            100                 105

<210> SEQ ID NO 53
<211> LENGTH: 107
<212> TYPE: PRT
<213> ORGANISM: Artificial Sequence
<220> FEATURE:
```

<223> OTHER INFORMATION: Synthetic

<400> SEQUENCE: 53

```
Asp Ile Gln Met Thr Gln Ser Pro Ser Ser Leu Ser Ala Ser Val Gly
1               5                   10                  15
Asp Arg Ile Thr Ile Thr Cys Ser Ala Ser Gln Gly Ile Ser Asn Tyr
            20                  25                  30
Leu Asn Trp Tyr Gln Gln Lys Pro Gly Lys Thr Val Lys Leu Leu Ile
        35                  40                  45
Tyr Tyr Thr Ser Ser Leu His Ser Gly Val Pro Ser Arg Phe Ser Gly
50                  55                  60
Ser Gly Ser Gly Thr Asp Tyr Thr Leu Thr Ile Ser Ser Leu Gln Pro
65                  70                  75                  80
Glu Asp Phe Ala Thr Tyr Tyr Cys Gln Gln Tyr Ser Lys Leu Pro Phe
                85                  90                  95
Thr Phe Gly Ser Gly Thr Lys Leu Glu Ile Lys
            100                 105
```

<210> SEQ ID NO 54
<211> LENGTH: 5
<212> TYPE: PRT
<213> ORGANISM: Artificial Sequence
<220> FEATURE:
<223> OTHER INFORMATION: Synthetic

<400> SEQUENCE: 54

```
Gly Tyr Tyr Ile His
1               5
```

<210> SEQ ID NO 55
<211> LENGTH: 17
<212> TYPE: PRT
<213> ORGANISM: Artificial Sequence
<220> FEATURE:
<223> OTHER INFORMATION: Synthetic

<400> SEQUENCE: 55

```
Tyr Ile Ser Ser Tyr Asn Ala Ala Thr Ser Phe Asn Gln Lys Phe Lys
1               5                   10                  15
Gly
```

<210> SEQ ID NO 56
<211> LENGTH: 10
<212> TYPE: PRT
<213> ORGANISM: Artificial Sequence
<220> FEATURE:
<223> OTHER INFORMATION: Synthetic

<400> SEQUENCE: 56

```
Thr Glu Leu Arg Gly Pro Trp Phe Ala Tyr
1               5                   10
```

<210> SEQ ID NO 57
<211> LENGTH: 10
<212> TYPE: PRT
<213> ORGANISM: Artificial Sequence
<220> FEATURE:
<223> OTHER INFORMATION: Synthetic

<400> SEQUENCE: 57

```
Ser Ala Ser Ser Ser Val Ser Tyr Met Asn
1               5                   10
```

<210> SEQ ID NO 58
<211> LENGTH: 7
<212> TYPE: PRT
<213> ORGANISM: Artificial Sequence
<220> FEATURE:
<223> OTHER INFORMATION: Synthetic

<400> SEQUENCE: 58

```
Asp Thr Ser Lys Leu Ala Ser
1               5
```

<210> SEQ ID NO 59
<211> LENGTH: 9
<212> TYPE: PRT
<213> ORGANISM: Artificial Sequence
<220> FEATURE:
<223> OTHER INFORMATION: Synthetic

<400> SEQUENCE: 59

```
Gln Gln Trp Ser Asn Asn Pro Leu Thr
1               5
```

<210> SEQ ID NO 60
<211> LENGTH: 17
<212> TYPE: PRT
<213> ORGANISM: Artificial Sequence
<220> FEATURE:
<223> OTHER INFORMATION: Synthetic

<400> SEQUENCE: 60

```
Tyr Ile Ser Cys Tyr Asn Gly Ala Thr Ser Phe Asn Gln Lys Phe Lys
1               5                   10                  15

Gly
```

<210> SEQ ID NO 61
<211> LENGTH: 119
<212> TYPE: PRT
<213> ORGANISM: Artificial Sequence
<220> FEATURE:
<223> OTHER INFORMATION: Synthetic

<400> SEQUENCE: 61

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
                20                  25                  30

Tyr Ile His Trp Val Arg Gln Ala Pro Gly Gln Gly Leu Glu Trp Met
            35                  40                  45

Gly Tyr Ile Ser Ser Tyr Asn Ala Ala Thr Ser Phe Asn Gln Lys Phe
        50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Glu Leu Arg Gly Pro Trp Phe Ala Tyr Trp Gly Gln Gly
            100                 105                 110

Thr Leu Val Thr Val Ser Ser
        115
```

<210> SEQ ID NO 62
<211> LENGTH: 119
<212> TYPE: PRT

```
<213> ORGANISM: Artificial Sequence
<220> FEATURE:
<223> OTHER INFORMATION: Synthetic

<400> SEQUENCE: 62

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Ile His Trp Val Arg Gln Ala Pro Gly Gln Gly Leu Glu Trp Ile
        35                  40                  45

Gly Tyr Ile Ser Ser Tyr Asn Ala Ala Thr Ser Phe Asn Gln Lys Phe
    50                  55                  60

Lys Gly Arg Val Thr Phe Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Glu Leu Arg Gly Pro Trp Phe Ala Tyr Trp Gly Gln Gly
            100                 105                 110

Thr Leu Val Thr Val Ser Ser
        115

<210> SEQ ID NO 63
<211> LENGTH: 119
<212> TYPE: PRT
<213> ORGANISM: Artificial Sequence
<220> FEATURE:
<223> OTHER INFORMATION: Synthetic

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Ile His Trp Val Lys Gln Ala Pro Gly Gln Gly Leu Glu Trp Ile
        35                  40                  45

Gly Tyr Ile Ser Ser Tyr Asn Ala Ala Thr Ser Phe Asn Gln Lys Phe
    50                  55                  60

Lys Gly Arg Val Thr Phe Thr Val Asp Thr Ser Thr Ser Thr Val Tyr
65                  70                  75                  80

Met Glu Phe Ser Ser Leu Arg Ser Glu Asp Thr Ala Val Tyr Tyr Cys
                85                  90                  95

Ala Arg Thr Glu Leu Arg Gly Pro Trp Phe Ala Tyr Trp Gly Gln Gly
            100                 105                 110

Thr Leu Val Thr Val Ser Ser
        115

<210> SEQ ID NO 64
<211> LENGTH: 119
<212> TYPE: PRT
<213> ORGANISM: Artificial Sequence
<220> FEATURE:
<223> OTHER INFORMATION: Synthetic

<400> SEQUENCE: 64

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Gly Tyr
            20                  25                  30
```

```
Tyr Ile His Trp Val Lys Gln Ala Pro Gly Gln Gly Leu Glu Trp Ile
        35                  40                  45
Gly Tyr Ile Ser Ser Tyr Asn Ala Ala Thr Ser Phe Asn Gln Lys Phe
    50                  55                  60
Lys Gly Arg Ala Thr Phe Thr Val Asp Thr Ser Thr Ser Thr Ala Tyr
65                  70                  75                  80
Met Glu Phe Ser Ser Leu Arg Ser Glu Asp Ser Ala Val Tyr Tyr Cys
                85                  90                  95
Ala Arg Thr Glu Leu Arg Gly Pro Trp Phe Ala Tyr Trp Gly Gln Gly
            100                 105                 110
Thr Leu Val Thr Val Ser Ser
            115

<210> SEQ ID NO 65
<211> LENGTH: 106
<212> TYPE: PRT
<213> ORGANISM: Artificial Sequence
<220> FEATURE:
<223> OTHER INFORMATION: Synthetic

<400> SEQUENCE: 65

Asp Ile Gln Met Thr Gln Ser Pro Ser Ser Leu Ser Ala Ser Val Gly
1               5                   10                  15
Asp Arg Val Thr Ile Thr Cys Ser Ala Ser Ser Ser Val Ser Tyr Met
            20                  25                  30
Asn Trp Tyr Gln Gln Lys Pro Gly Lys Ala Pro Lys Leu Leu Ile Tyr
        35                  40                  45
Asp Thr Ser Lys Leu Ala Ser Gly Val Pro Ser Arg Phe Ser Gly Ser
    50                  55                  60
Gly Ser Gly Thr Asp Phe Thr Leu Thr Ile Ser Ser Leu Gln Pro Glu
65                  70                  75                  80
Asp Phe Ala Thr Tyr Tyr Cys Gln Gln Trp Ser Asn Asn Pro Leu Thr
                85                  90                  95
Phe Gly Gln Gly Thr Lys Leu Glu Ile Lys
            100                 105

<210> SEQ ID NO 66
<211> LENGTH: 106
<212> TYPE: PRT
<213> ORGANISM: Artificial Sequence
<220> FEATURE:
<223> OTHER INFORMATION: Synthetic

<400> SEQUENCE: 66

Asp Thr Gln Met Thr Gln Ser Pro Ser Ser Leu Ser Ala Ser Val Gly
1               5                   10                  15
Asp Arg Val Thr Ile Thr Cys Ser Ala Ser Ser Ser Val Ser Tyr Met
            20                  25                  30
Asn Trp Tyr Gln Gln Lys Pro Gly Lys Ala Pro Lys Arg Leu Ile Tyr
        35                  40                  45
Asp Thr Ser Lys Leu Ala Ser Gly Val Pro Ser Arg Phe Ser Gly Ser
    50                  55                  60
Gly Ser Gly Thr Asp Tyr Thr Leu Thr Ile Ser Ser Leu Gln Pro Glu
65                  70                  75                  80
Asp Phe Ala Thr Tyr Tyr Cys Gln Gln Trp Ser Asn Asn Pro Leu Thr
                85                  90                  95
Phe Gly Gln Gly Thr Lys Leu Glu Ile Lys
```

```
<210> SEQ ID NO 67
<211> LENGTH: 106
<212> TYPE: PRT
<213> ORGANISM: Artificial Sequence
<220> FEATURE:
<223> OTHER INFORMATION: Synthetic

<400> SEQUENCE: 67

Asp Thr Gln Leu Thr Gln Ser Pro Ser Ser Leu Ser Ala Ser Val Gly
1               5                   10                  15

Asp Arg Val Thr Met Thr Cys Ser Ala Ser Ser Ser Val Ser Tyr Met
            20                  25                  30

Asn Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Leu Thr Ile Ser Ser Met Gln Pro Glu
65                  70                  75                  80

Asp Phe Ala Thr Tyr Tyr Cys Gln Gln Trp Ser Asn Asn Pro Leu Thr
                85                  90                  95

Phe Gly Gln Gly Thr Lys Leu Glu Ile Lys
            100                 105

<210> SEQ ID NO 68
<211> LENGTH: 5
<212> TYPE: PRT
<213> ORGANISM: Artificial Sequence
<220> FEATURE:
<223> OTHER INFORMATION: Synthetic

<400> SEQUENCE: 68

Thr Tyr Thr Met His
1               5

<210> SEQ ID NO 69
<211> LENGTH: 17
<212> TYPE: PRT
<213> ORGANISM: Artificial Sequence
<220> FEATURE:
<223> OTHER INFORMATION: Synthetic

<400> SEQUENCE: 69

Tyr Ile Asn Pro Ser Ser Gly Tyr Thr Asn Tyr Asn Gln Lys Phe Lys
1               5                   10                  15

Asp

<210> SEQ ID NO 70
<211> LENGTH: 9
<212> TYPE: PRT
<213> ORGANISM: Artificial Sequence
<220> FEATURE:
<223> OTHER INFORMATION: Synthetic

<400> SEQUENCE: 70

Leu Arg Ser Arg Gly Tyr Phe Asp Tyr
1               5

<210> SEQ ID NO 71
<211> LENGTH: 11
<212> TYPE: PRT
<213> ORGANISM: Artificial Sequence
```

<220> FEATURE:
<223> OTHER INFORMATION: Synthetic

<400> SEQUENCE: 71

Lys Ala Ser Gln Asn Val Gly Thr Ala Val Val
1               5                   10

<210> SEQ ID NO 72
<211> LENGTH: 7
<212> TYPE: PRT
<213> ORGANISM: Artificial Sequence
<220> FEATURE:
<223> OTHER INFORMATION: Synthetic

<400> SEQUENCE: 72

Ser Ala Ser Asn Arg Tyr Thr
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic

<400> SEQUENCE: 73

Gln Gln Tyr Ser Ser Tyr Pro Tyr Thr
1               5

<210> SEQ ID NO 74
<211> LENGTH: 118
<212> TYPE: PRT
<213> ORGANISM: Artificial Sequence
<220> FEATURE:
<223> OTHER INFORMATION: Synthetic

<400> SEQUENCE: 74

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Thr Met His Trp Val Arg Gln Ala Pro Gly Gln Gly Leu Glu Trp Met
        35                  40                  45

Gly Tyr Ile Asn Pro Ser Ser Gly Tyr Thr Asn Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ser Arg Leu Arg Ser Arg Gly Tyr Phe Asp Tyr Trp Gly Gln Gly Thr
            100                 105                 110

Leu Val Thr Val Ser Ser
        115

<210> SEQ ID NO 75
<211> LENGTH: 118
<212> TYPE: PRT
<213> ORGANISM: Artificial Sequence
<220> FEATURE:
<223> OTHER INFORMATION: Synthetic

<400> SEQUENCE: 75

Gln Val Gln Leu Val Gln Ser Gly Ala Glu Val Lys Lys Pro Gly Ala

```
1               5                   10                  15
Ser Val Lys Val Ser Cys Lys Ala Ser Gly Tyr Thr Phe Thr Thr Tyr
                20                  25                  30

Thr Met His Trp Val Arg Gln Ala Pro Gly Gln Gly Leu Glu Trp Leu
            35                  40                  45

Gly Tyr Ile Asn Pro Ser Ser Gly Tyr Thr Asn Tyr Asn Gln Lys Phe
        50                  55                  60

Lys Asp Arg Val Thr Met Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Arg Ser Arg Gly Tyr Phe Asp Tyr Trp Gly Gln Gly Thr
                100                 105                 110

Leu Val Thr Val Ser Ser
            115
```

<210> SEQ ID NO 76
<211> LENGTH: 118
<212> TYPE: PRT
<213> ORGANISM: Artificial Sequence
<220> FEATURE:
<223> OTHER INFORMATION: Synthetic

<400> SEQUENCE: 76

```
Gln Val Gln Leu Val Gln Ser Gly Ala Glu Val Ala Lys Pro Gly Ala
1               5                   10                  15

Ser Val Lys Val Ser Cys Lys Ala Ser Gly Tyr Thr Phe Thr Thr Tyr
                20                  25                  30

Thr Met His Trp Val Lys Gln Ala Pro Gly Gln Gly Leu Glu Trp Leu
            35                  40                  45

Gly Tyr Ile Asn Pro Ser Ser Gly Tyr Thr Asn Tyr Asn Gln Lys Phe
        50                  55                  60

Lys Asp Arg Val Thr Met Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Leu Arg Ser Arg Gly Tyr Phe Asp Tyr Trp Gly Gln Gly Thr
                100                 105                 110

Leu Val Thr Val Ser Ser
            115
```

<210> SEQ ID NO 77
<211> LENGTH: 118
<212> TYPE: PRT
<213> ORGANISM: Artificial Sequence
<220> FEATURE:
<223> OTHER INFORMATION: Synthetic

<400> SEQUENCE: 77

```
Gln Val Gln Leu Val Gln Ser Gly Ala Glu Val Ala Lys Pro Gly Ala
1               5                   10                  15

Ser Val Lys Met Ser Cys Lys Ala Ser Gly Tyr Thr Phe Thr Thr Tyr
                20                  25                  30

Thr Met His Trp Val Lys Gln Ala Pro Gly Gln Gly Leu Glu Trp Leu
            35                  40                  45

Gly Tyr Ile Asn Pro Ser Ser Gly Tyr Thr Asn Tyr Asn Gln Lys Phe
        50                  55                  60
```

-continued

Lys Asp Arg Val Thr Leu Thr Ala Asp Thr Ser Ser Thr Val Tyr
65                  70                  75                  80

Met Glu Leu Ser Ser Leu Arg Ser Glu Asp Thr Ala Val Tyr Tyr Cys
            85                  90                  95

Ala Ser Leu Arg Ser Arg Gly Tyr Phe Asp Tyr Trp Gly Gln Gly Thr
            100                 105                 110

Leu Leu Thr Val Ser Ser
        115

<210> SEQ ID NO 78
<211> LENGTH: 118
<212> TYPE: PRT
<213> ORGANISM: Artificial Sequence
<220> FEATURE:
<223> OTHER INFORMATION: Synthetic

<400> SEQUENCE: 78

Gln Val Gln Leu Gln Gln Ser Gly Ala Glu Val Ala Lys Pro Gly Ala
1               5                   10                  15

Ser Val Lys Met Ser Cys Lys Ala Ser Gly Tyr Thr Phe Thr Thr Tyr
            20                  25                  30

Thr Met His Trp Val Lys Gln Arg Pro Gly Gln Gly Leu Glu Trp Leu
        35                  40                  45

Gly Tyr Ile Asn Pro Ser Ser Gly Tyr Thr Asn Tyr Asn Gln Lys Phe
    50                  55                  60

Lys Asp Arg Val Thr Leu Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Ser Leu Arg Ser Arg Gly Tyr Phe Asp Tyr Trp Gly Gln Gly Thr
            100                 105                 110

Leu Leu Thr Val Ser Ser
        115

<210> SEQ ID NO 79
<211> LENGTH: 118
<212> TYPE: PRT
<213> ORGANISM: Artificial Sequence
<220> FEATURE:
<223> OTHER INFORMATION: Synthetic

<400> SEQUENCE: 79

Gln Val Gln Leu Gln Gln Ser Gly Ala Glu Val Ala Lys Pro Gly Ala
1               5                   10                  15

Ser Val Lys Met Ser Cys Lys Ala Ser Gly Tyr Thr Phe Thr Thr Tyr
            20                  25                  30

Thr Met His Trp Val Lys Gln Arg Pro Gly Gln Gly Leu Glu Trp Leu
        35                  40                  45

Gly Tyr Ile Asn Pro Ser Ser Gly Tyr Thr Asn Tyr Asn Gln Lys Phe
    50                  55                  60

Lys Asp Arg Ala Thr Leu Thr Ala Gly Lys Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Ser Leu Arg Ser Arg Gly Tyr Phe Asp Tyr Trp Gly Gln Gly Thr
            100                 105                 110

Leu Leu Thr Val Ser Ser
        115

<210> SEQ ID NO 80
<211> LENGTH: 107
<212> TYPE: PRT
<213> ORGANISM: Artificial Sequence
<220> FEATURE:
<223> OTHER INFORMATION: Synthetic

<400> SEQUENCE: 80

```
Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Gly Thr Ala
            20                  25                  30

Val Val Trp Tyr Gln Gln Lys Pro Gly Lys Ala Pro Lys Leu Leu Ile
        35                  40                  45

Tyr Ser Ala Ser Asn Arg Tyr Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Tyr
                85                  90                  95

Thr Phe Gly Gln Gly Thr Lys Leu Glu Ile Lys
            100                 105
```

<210> SEQ ID NO 81
<211> LENGTH: 107
<212> TYPE: PRT
<213> ORGANISM: Artificial Sequence
<220> FEATURE:
<223> OTHER INFORMATION: Synthetic

<400> SEQUENCE: 81

```
Asp Ile Gln Leu Thr Gln Ser Pro Ser Phe Leu Ser Thr Ser Val Gly
1               5                   10                  15

Asp Arg Val Thr Ile Thr Cys Lys Ala Ser Gln Asn Val Gly Thr Ala
            20                  25                  30

Val Val Trp Tyr Gln Gln Lys Pro Gly Lys Ser Pro Lys Leu Leu Ile
        35                  40                  45

Tyr Ser Ala Ser Asn Arg Tyr Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Phe Tyr Cys Gln Gln Tyr Ser Ser Tyr Pro Tyr
                85                  90                  95

Thr Phe Gly Gln Gly Thr Lys Leu Glu Ile Lys
            100                 105
```

<210> SEQ ID NO 82
<211> LENGTH: 107
<212> TYPE: PRT
<213> ORGANISM: Artificial Sequence
<220> FEATURE:
<223> OTHER INFORMATION: Synthetic

<400> SEQUENCE: 82

```
Asp Ile Gln Met Thr Gln Ser Pro Ser Phe Leu Ser Thr Ser Val Gly
1               5                   10                  15

Asp Arg Val Thr Ile Thr Cys Lys Ala Ser Gln Asn Val Gly Thr Ala
            20                  25                  30
```

```
Val Val Trp Tyr Gln Gln Lys Pro Gly Lys Ser Pro Lys Leu Leu Ile
        35                  40                  45

Tyr Ser Ala Ser Asn Arg Tyr Thr Gly Val Pro Ser Arg Phe Ser Gly
 50                  55                  60

Ser Gly Ser Gly Thr Glu Phe Thr Leu Thr Ile Ser Ser Met Gln Pro
 65                  70                  75                  80

Glu Asp Phe Ala Thr Phe Phe Cys Gln Gln Tyr Ser Ser Tyr Pro Tyr
                 85                  90                  95

Thr Phe Gly Gln Gly Thr Lys Leu Glu Ile Lys
                100                 105
```

<210> SEQ ID NO 83
<211> LENGTH: 107
<212> TYPE: PRT
<213> ORGANISM: Artificial Sequence
<220> FEATURE:
<223> OTHER INFORMATION: Synthetic

<400> SEQUENCE: 83

```
Asp Ile Val Met Thr Gln Ser Pro Ser Phe Leu Ser Thr Ser Val Gly
 1               5                  10                  15

Asp Arg Val Thr Ile Thr Cys Lys Ala Ser Gln Asn Val Gly Thr Ala
                20                  25                  30

Val Val Trp Tyr Gln Gln Lys Pro Gly Lys Ser Pro Lys Leu Leu Ile
        35                  40                  45

Tyr Ser Ala Ser Asn Arg Tyr Thr Gly Val Pro Asp Arg Phe Ser Gly
 50                  55                  60

Ser Gly Ser Gly Thr Glu Phe Thr Leu Thr Ile Ser Ser Met Gln Pro
 65                  70                  75                  80

Glu Asp Phe Ala Thr Phe Phe Cys Gln Gln Tyr Ser Ser Tyr Pro Tyr
                 85                  90                  95

Thr Phe Gly Gly Gly Thr Lys Leu Glu Ile Lys
                100                 105
```

<210> SEQ ID NO 84
<211> LENGTH: 107
<212> TYPE: PRT
<213> ORGANISM: Artificial Sequence
<220> FEATURE:
<223> OTHER INFORMATION: Synthetic

<400> SEQUENCE: 84

```
Glu Ile Val Met Thr Gln Ser Pro Ala Thr Leu Ser Val Ser Pro Gly
 1               5                  10                  15

Glu Arg Ala Thr Leu Ser Cys Lys Ala Ser Gln Asn Val Gly Thr Ala
                20                  25                  30

Val Val Trp Tyr Gln Gln Lys Pro Gly Gln Ala Pro Arg Leu Leu Ile
        35                  40                  45

Tyr Ser Ala Ser Asn Arg Tyr Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Ser Ser Tyr Pro Tyr
                 85                  90                  95

Thr Phe Gly Gln Gly Thr Lys Leu Glu Ile Lys
                100                 105
```

<210> SEQ ID NO 85

```
<211> LENGTH: 107
<212> TYPE: PRT
<213> ORGANISM: Artificial Sequence
<220> FEATURE:
<223> OTHER INFORMATION: Synthetic

<400> SEQUENCE: 85

Glu Ile Val Met Thr Gln Ser Pro Ala Thr Leu Ser Thr Ser Pro Gly
1               5                   10                  15

Glu Arg Ala Thr Leu Ser Cys Lys Ala Ser Gln Asn Val Gly Thr Ala
            20                  25                  30

Val Val Trp Tyr Gln Gln Lys Pro Gly Gln Ser Pro Arg Leu Leu Ile
        35                  40                  45

Tyr Ser Ala Ser Asn Arg Tyr Thr Gly Ile Pro Asp Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Phe Phe Cys Gln Gln Tyr Ser Ser Tyr Pro Tyr
                85                  90                  95

Thr Phe Gly Gln Gly Thr Lys Leu Glu Ile Lys
            100                 105

<210> SEQ ID NO 86
<211> LENGTH: 107
<212> TYPE: PRT
<213> ORGANISM: Artificial Sequence
<220> FEATURE:
<223> OTHER INFORMATION: Synthetic

<400> SEQUENCE: 86

Glu Ile Val Met Thr Gln Ser Pro Ala Thr Leu Ser Thr Ser Pro Gly
1               5                   10                  15

Glu Arg Val Thr Ile Ser Cys Lys Ala Ser Gln Asn Val Gly Thr Ala
            20                  25                  30

Val Val Trp Tyr Gln Gln Lys Pro Gly Gln Ser Pro Arg Leu Leu Ile
        35                  40                  45

Tyr Ser Ala Ser Asn Arg Tyr Thr Gly Ile Pro Asp Arg Phe Thr Gly
    50                  55                  60

Ser Gly Ser Gly Thr Asp Phe Thr Leu Thr Ile Ser Ser Met Gln Ser
65                  70                  75                  80

Glu Asp Phe Ala Val Phe Phe Cys Gln Gln Tyr Ser Ser Tyr Pro Tyr
                85                  90                  95

Thr Phe Gly Gly Gly Thr Lys Leu Glu Ile Lys
            100                 105
```